US012721882B2

(12) United States Patent
Antipov

(10) Patent No.: US 12,721,882 B2
(45) Date of Patent: Sep. 1, 2026

(54) ENUMERATION OF GENETICALLY ENGINEERED MICROORGANISMS BY LIVE CELL COUNTING TECHNIQUES

(71) Applicant: SYNLOGIC OPERATING COMPANY, INC., Cambridge, MA (US)

(72) Inventor: Eugene Antipov, Watertown, MA (US)

(73) Assignee: Synlogic Operating Company, Inc., Winchester, MA (US)

( * ) Notice: Subject to any disclaimer, the term of this patent is extended or adjusted under 35 U.S.C. 154(b) by 1065 days.

(21) Appl. No.: 17/607,248

(22) PCT Filed: Apr. 29, 2020

(86) PCT No.: PCT/US2020/030468

§ 371 (c)(1),
(2) Date: Oct. 28, 2021

(87) PCT Pub. No.: WO2020/223345

PCT Pub. Date: Nov. 5, 2020

(65) Prior Publication Data

US 2022/0257732 A1 Aug. 18, 2022

Related U.S. Application Data

(60) Provisional application No. 62/946,785, filed on Dec. 11, 2019, provisional application No. 62/840,281, filed on Apr. 29, 2019.

(51) Int. Cl.

| | |
|---|---|
| ***A61K 35/74*** | (2015.01) |
| ***A61K 35/741*** | (2015.01) |
| ***A61K 35/742*** | (2015.01) |
| ***A61K 35/744*** | (2015.01) |
| ***A61K 35/745*** | (2015.01) |
| ***A61K 35/747*** | (2015.01) |
| ***A61K 38/50*** | (2006.01) |
| ***A61K 38/51*** | (2006.01) |
| ***A61K 47/26*** | (2006.01) |
| ***A61P 3/00*** | (2006.01) |
| ***A61P 35/00*** | (2006.01) |
| ***C12N 1/00*** | (2006.01) |
| ***C12N 1/20*** | (2006.01) |
| ***C12N 9/06*** | (2006.01) |
| ***C12N 9/88*** | (2006.01) |
| ***C12N 15/63*** | (2006.01) |
| ***C12N 15/70*** | (2006.01) |
| ***G01N 1/30*** | (2006.01) |
| ***G01N 15/06*** | (2006.01) |
| *G01N 15/01* | (2024.01) |
| *G01N 15/075* | (2024.01) |

(52) U.S. Cl.

CPC ............ *A61K 38/51* (2013.01); *A61K 35/741* (2013.01); *A61K 35/742* (2013.01); *A61K 35/744* (2013.01); *A61K 35/745* (2013.01); *A61K 35/747* (2013.01); *A61K 38/50* (2013.01); *A61K 47/26* (2013.01); *A61P 35/00* (2018.01); *C12N 1/20* (2013.01); *C12N 9/0022* (2013.01); *C12N 9/88* (2013.01); *C12N 15/635* (2013.01); *C12N 15/70* (2013.01); *C12Y 104/03002* (2013.01); *C12Y 403/01024* (2013.01); *G01N 1/30* (2013.01); *G01N 15/06* (2013.01); *C12N 2800/101* (2013.01); *C12N 2820/002* (2013.01); *C12N 2830/002* (2013.01); *G01N 2001/302* (2013.01); *G01N 15/01* (2024.01); *G01N 15/075* (2024.01)

(58) Field of Classification Search

CPC .... A61K 38/51; A61K 35/741; A61K 35/742; A61K 35/744; A61K 35/745; A61K 35/747; A61K 38/50; A61K 47/26; A61K 35/74; A61K 9/19; A61K 47/18; A61P 35/00; A61P 3/00; C12N 1/20; C12N 9/0022; C12N 9/88; C12N 15/635; C12N 15/70; C12N 2800/101; C12N 2820/002; C12N 2830/002; C12N 1/00; C12N 2510/00; C12Y 104/03002; C12Y 403/01024; G01N 1/30; G01N 15/06; G01N 15/01; G01N 15/075; G01N 2001/302

See application file for complete search history.

(56) References Cited

FOREIGN PATENT DOCUMENTS

| | | | | |
|---|---|---|---|---|
| WO | 2016/090243 | A1 | 6/2016 | |
| WO | WO 2016183531 | A1 * | 11/2016 | ........... C07K 14/195 |
| WO | 2018/129404 | A1 | 7/2018 | |

OTHER PUBLICATIONS

Isabella V.M et al., "Development of a synthetic live bacterial therapeutic for the human metabolic disease phenylketonuria", Nature Biotechnology, vol. 36 No. 9 Sep. 2018, pp. 857-866 (total pp. 17). (Year: 2018).*

Ou F. et al., "Absolute bacterial cell enumeration using flow cytometry", Journal of Applied Microbiology, 2017, vol. 123, pp. 464-477. (Year: 2017).*

Ben Amor et al., Multiparametric flow cytometry and cell sorting for the assessment of viable, injured, and dead bifidobacterium cells during bile salt stress. Appl Environ Microbiol. Nov. 2002;68(11):5209-16.

Davis et al., Enumeration of probiotic strains: Review of culture-dependent and alternative techniques to quantify viable bacteria. J Microbiol Methods. Aug. 2014;103:9-17.

(Continued)

*Primary Examiner* — Satyendra K Singh

(74) *Attorney, Agent, or Firm* — McCarter & English, LLP; Marcie B. Clarke

(57) ABSTRACT

Genetically engineered microorganisms, e.g., genetically engineered bacteria, compositions and formulations thereof, as well as methods for characterizing, dosing, and determining the activity of the bacteria, compositions, and formulations, e.g., using a live cell counting method are disclosed.

12 Claims, 19 Drawing Sheets

(56) References Cited

OTHER PUBLICATIONS

Majeed et al., Rapid assessment of viable but non-culturable Bacillus coagulans MTCC 5856 in commercial formulations using Flow cytometry. PLoS One. Feb. 23, 2018;13(2):e0192836, 14 pages.
International Search Report and Written Opinion for Application No. PCT/US2020/030468, dated Sep. 10, 2020, 13 pages.

* cited by examiner

| LOT | TOLL CELLS / mL | LIVE CELLS / mL | CFU / mL |
| --- | --- | --- | --- |
| FROZEN LIQUID | 2.36E11 | 2.13E11 | 8.27E10 |
| LYOPHILIZED | 1.65E11 | 1.33E11 | 1.09E10 |
| SPRAY DRIED | 1.75E11 | 1.51E11 | 7.81E6 |

CONCENTRATION OF SYNB1618 IN DIFFERENT BATCHES AS QUANTIFIED BY COLONY FORMING UNITS OR LIVE CELLS

| SYNB1618 | METHOD OF CONCENTRATION | CFU/mL | LIVE CELLS/mL | LIVE CELLS/CFU RATIOS |
|---|---|---|---|---|
| BATCH A | FROZEN LIQUID | $1.1 \times 10^{11}$ | $2.1 \times 10^{11}$ | 1.9 |
| BATCH B | SPRAY DRIED | $7.8 \times 10^{6}$ | $1.5 \times 10^{11}$ | 19,334 |
| BATCH C | LYOPHILIZED | $3.7 \times 10^{9}$ | $1.1 \times 10^{11}$ | 30.1 |
| BATCH D | SPRAY DRIED | $8.1 \times 10^{8}$ | $5.3 \times 10^{10}$ | 65.4 |
| BATCH E | SPRAY DRIED | $1.8 \times 10^{8}$ | $1.5 \times 10^{11}$ | 833 |

*FIG. 6A*

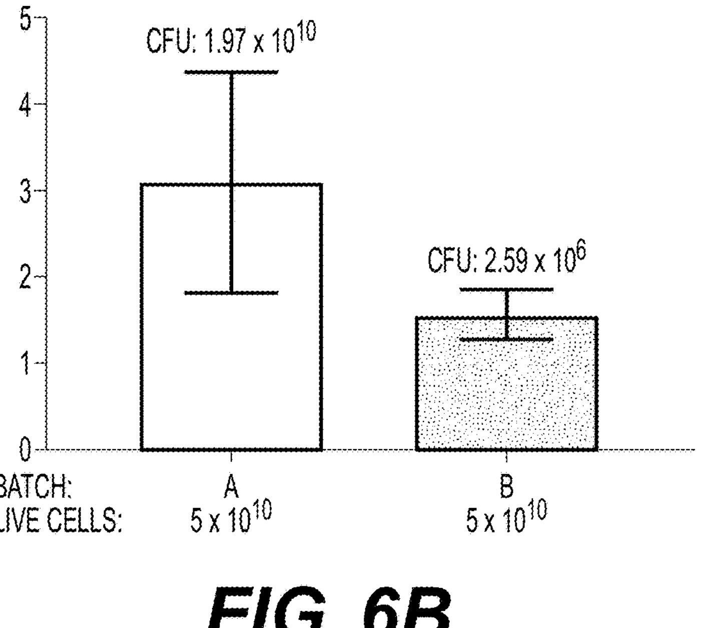

*FIG. 6B*

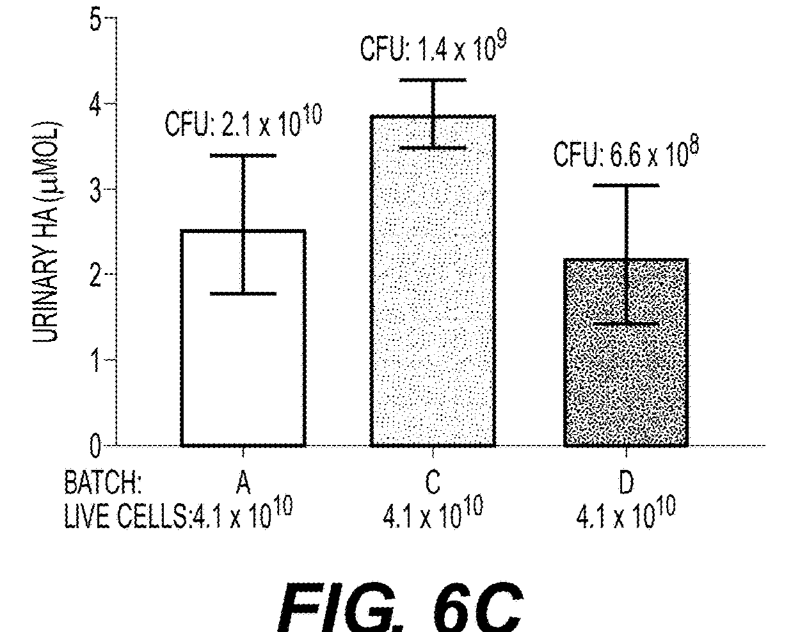

*FIG. 6C*

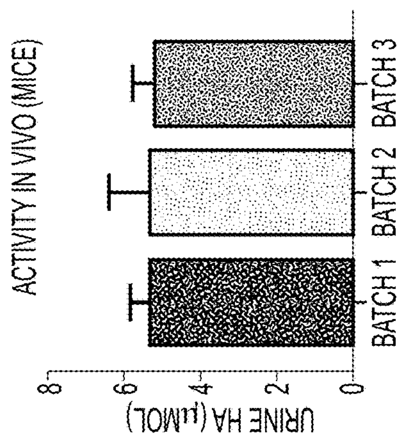
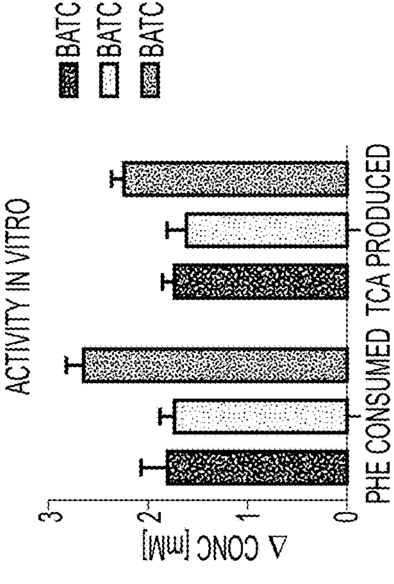
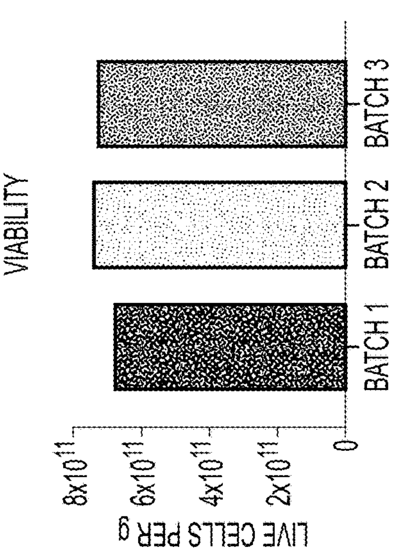
*FIG. 8*

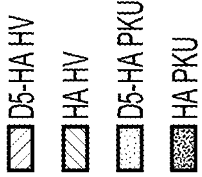
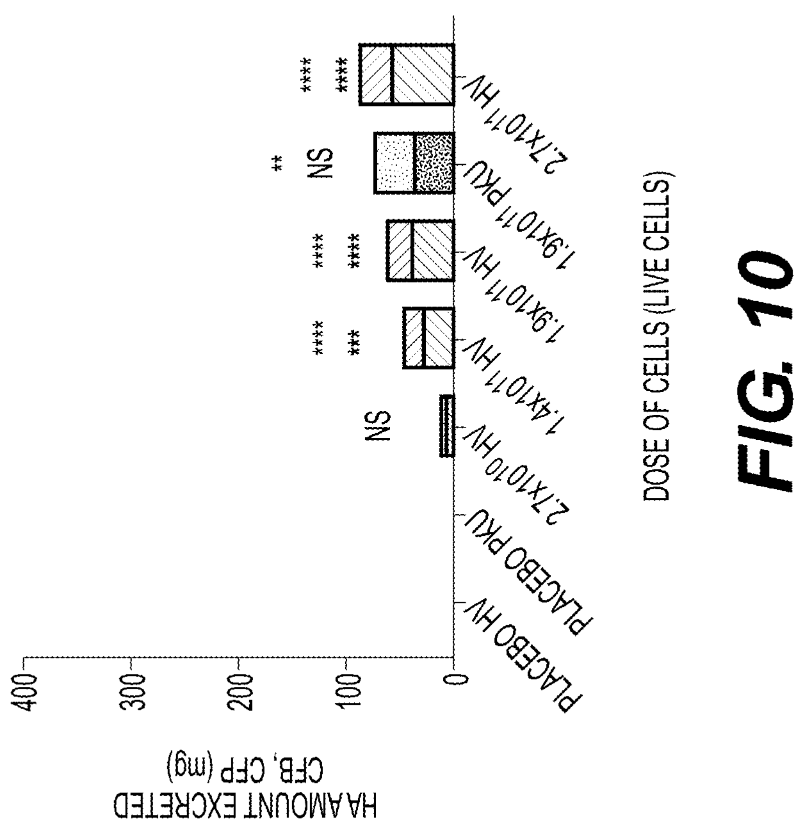
FIG. 10

#12
1.80E+11
1.60E+11
1.40E+11
1.20E+11
1.00E+11
8.00E+10
6.00E+10
4.00E+10
2.00E+10
0.00E+00
TOTAL CELLS/mL
DEAD CELLS/mL
LIVE CELLS/mL

| | TOTAL CELLS/mL | DEAD CELLS/mL | LIVE CELLS/mL | %VIABILITY |
|---|---|---|---|---|
| MEAN | 1.38E+11 | 1.11E+10 | 1.27E+11 | 91.9% |
| SD | 1.57E+10 | 2.90E+09 | 1.56E+10 | 2.3% |
| %CV | 11.3 | 26.1 | 12.3 | 2.5 |

ENUMERATION OF GENETICALLY ENGINEERED MICROORGANISMS BY LIVE CELL COUNTING TECHNIQUES

REFERENCE TO RELATED APPLICATIONS

This application claims the benefit of U.S. Provisional Application No. 62/840,281, filed on Apr. 29, 2019, and U.S. Provisional Application No. 62/946,785, filed on Dec. 11, 2019, the contents of which are incorporated by reference in their entirety.

BACKGROUND

To determine bacterial cell count, "[t]he widely used gold standard method is Colonies Forming Units (CFU)," which is based on the number of dividing bacterial cells. Hazan et al. (2012), A method for high throughput determination of viable bacteria cell counts in 96-well plates; see also Jung and Jung (2016), Real-time bacterial microcolony counting using on-chip microscopy. The CFU method has been described as advantageous, because "only viable bacteria are counted with this method." Id. For probiotic bacteria dosing, "the colony forming units per gram of product is an important parameter. Although the information about the minimum effective concentrations is still insufficient, it is generally accepted that probiotic products should have a minimum concentration of $10^6$ CFU/mL or gram." Kechagia et al. (2013), Health benefits of probiotics: a review. Recent guidance by the U.S. Food and Drug Administration (FDA) for live biotherapeutic products similarly advises that the "[p]otency of live microbial products is generally a measure of viable cells per unit or dose, i.e., colony-forming units (CFUs)" and "[d]uring early clinical development, the potency assay may be an assessment of CFU." FDA Early Clinical Trials with Live Biotherapeutic Products: Chemistry, Manufacturing, and Control Information: Guidance for Industry (June 2016). Yet the concentration of bacteria needed to obtain clinical effect can vary by "100-fold or more in terms of colony forming units (cfu)." Minelli and Benini (2008), Relationship between number of bacteria and their probiotic effects.

SUMMARY

In some embodiments, the disclosure provides engineered microorganisms, e.g., genetically engineered bacteria, comprising one or more gene(s) for producing a desired therapeutic molecule, and compositions and formulations thereof, as well as methods for characterizing, dosing, and determining the activity of the bacteria, compositions, and formulations, e.g., using a live cell counting method. In some embodiments, the disclosure provides methods of manufacturing engineered microorganisms, e.g., genetically engineered bacteria, compositions, and formulations, e.g., using the live cell counting methods disclosed herein. In some embodiments, the disclosure provides methods for treating a subject suffering from a disease or disorder by administering engineered microorganisms, e.g., genetically engineered bacteria, compositions, and formulations, as assayed, dosed, and/or manufactured using the methods for characterizing, dosing, and determining the activity disclosed herein, e.g., live cell counting method. In some embodiments, genetically engineered bacteria (e.g., comprising gene(s) for producing an anti-cancer molecule, e.g., a deadenylate cyclase gene or an enzyme capable of producing a stimulator of interferon gene agonist; or comprising gene(s) encoding a modified arginine biosynthesis pathway, e.g., deleted arginine repressor, modified arginine repressor binding sites, and/or arginine feedback resistant N-acetylglutamate synthase mutation; or comprising gene(s) for producing a phenylalanine metabolizing enzyme), compositions and formulations thereof, as assayed, dosed, and/or manufactured using the methods for characterizing, dosing, and determining the activity disclosed herein, e.g., live cell counting method, may be used to treat a subject suffering from a disease or disorder, e.g., a metabolic disease, a cancer, etc. In some embodiments, the microorganisms, compositions, or formulations are capable of reducing hyperphenylalaninemia in a subject and/or treating a disease or disorder associated with hyperphenylalaninemia, e.g., phenylketonuria (PKU). In some embodiments, the microorganisms, compositions, or formulations are capable of reducing excess ammonia in a subject and/or treating a disease or disorder associated with hyperammonemia, e.g., a urea cycle disorder (UCD) or a cancer. In some embodiments, the microorganisms, compositions, or formulations are capable of producing an anti-cancer molecule, e.g., a deadenylate cyclase or an enzyme capable of producing a stimulator of interferon gene (STING) agonist, and/or treating cancer.

The present disclosure describes methods for characterizing, dosing, and determining the activity of microorganisms, e.g., genetically engineered bacteria, e.g., by live cell counting. The live cell counting method disclosed herein encompasses determining the number of living dividing cells as well as living non-dividing cells. By contrast, colony-forming unit (CFU) methods generally capture living dividing cells but not living non-dividing (i.e., non-colony-forming) cells. The present disclosure demonstrates that living non-dividing engineered microorganisms, e.g., genetically engineered bacteria, are capable of producing a desired activity, e.g., one or more therapeutic molecule(s), and thus are viable and potent, despite not having the ability to divide. Thus, in some embodiments, the methods for characterizing, dosing, and determining the activity of microorganisms, e.g., live cell counting methods, disclosed herein provide an improved, e.g., more accurate, measure of desired activity, e.g., therapeutic molecule production or function, than CFU counting methods. In some embodiments, lyophilized compositions and formulations of the engineered microorganisms, e.g., genetically engineered bacteria, assayed by the methods for characterizing, dosing, and determining the activity of microorganisms, e.g., live cell counting methods, disclosed herein have a potency that is equal to or greater than that of the non-lyophilized bacteria. In some embodiments, the engineered microorganisms, e.g., genetically engineered bacteria, and compositions and formulations thereof assayed by the live cell counting method have stable shelf-life. In some embodiments, the live cell counting method provides an improved, e.g., more accurate, measure of bacterial activity, therapeutic dosing, and/or therapeutic efficacy than the CFU method. In some embodiments, live cell counting results in an improved method for manufacturing and/or dosing bacteria than the CFU method.

BRIEF DESCRIPTION OF THE FIGURES

FIG. 6A depicts a table showing CFU/mL, live cells/mL and live cell/CFU for frozen, spray dried, or lyophilized bacteria genetically engineered to metabolize phenylalanine (SYNB1618). FIG. 6B depicts a bar graph showing the amount of urinary HA excreted in mice administered phenylalanine metabolizing bacteria SYNB1618 (frozen or spray dried). All groups of mice were administered compositions of genetically engineered bacteria having approximately the same live cell count. FIG. 6C depicts a bar graph showing the amount of HA excreted in mice administered formulations comprising bacteria genetically engineered to degrade phenylalanine, where the formulations comprise bacteria that were frozen, lyophilized, or spray dried. Mice in all three groups were administered the same live cell count.

FIG. 8 shows the viability of three batches of phenylalanine metabolizing bacteria prepared using the same method (solid batch). Here, viability is measured by the number of live cells per gram of formulation. In vitro rates at which phenylalanine is consumed and TCA is produced, and urine HA levels in mice are also shown.

FIG. 10 shows urinary hippurate (HA) and labeled D5-HA using a liquid formulation. CFB=change from baseline. CFP=change from placebo. HV=healthy volunteer. PKU=phenylketonuria patient.

DETAILED DESCRIPTION

Figure 1:
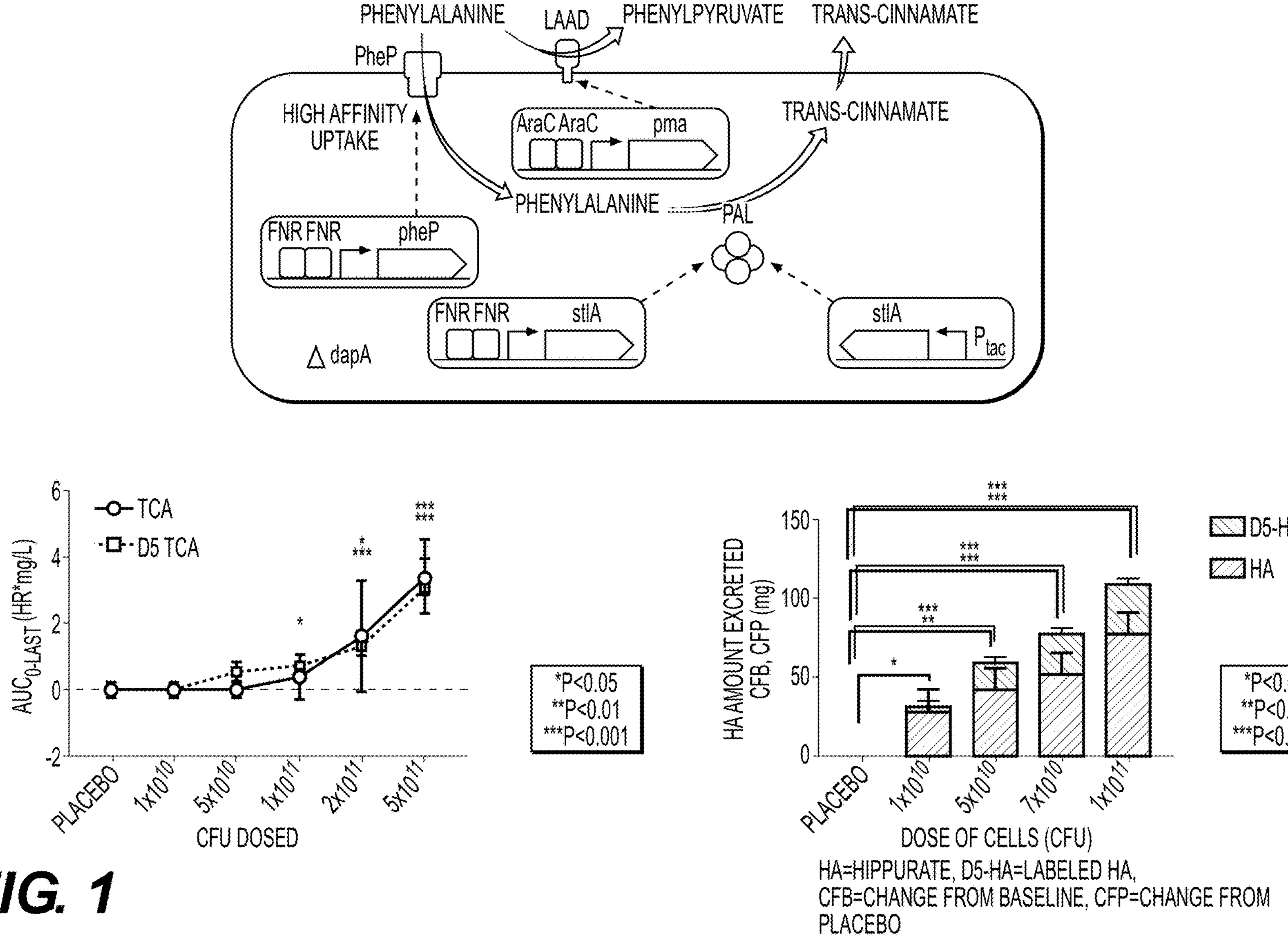
FIG. 1 depicts a schematic of a genetically engineered bacterium for the treatment of a disease associated with hyperphenylalaninemia, e.g., PKU. Also depicted in FIG. 1 is a graph showing the formation of transcinnamic acid (TCA) in subjects administered increasing amounts of the genetically engineered bacteria, and a graph showing the excretion of hippuric acid (HA) in subjects administered increasing amounts of the genetically engineered bacteria. See Isabella et al., (2018) "Development of a synthetic live bacterial therapeutic for the human metabolic disease phenylketonuria," the contents of which are hereby incorporated by reference in their entirety.
Figure 2:
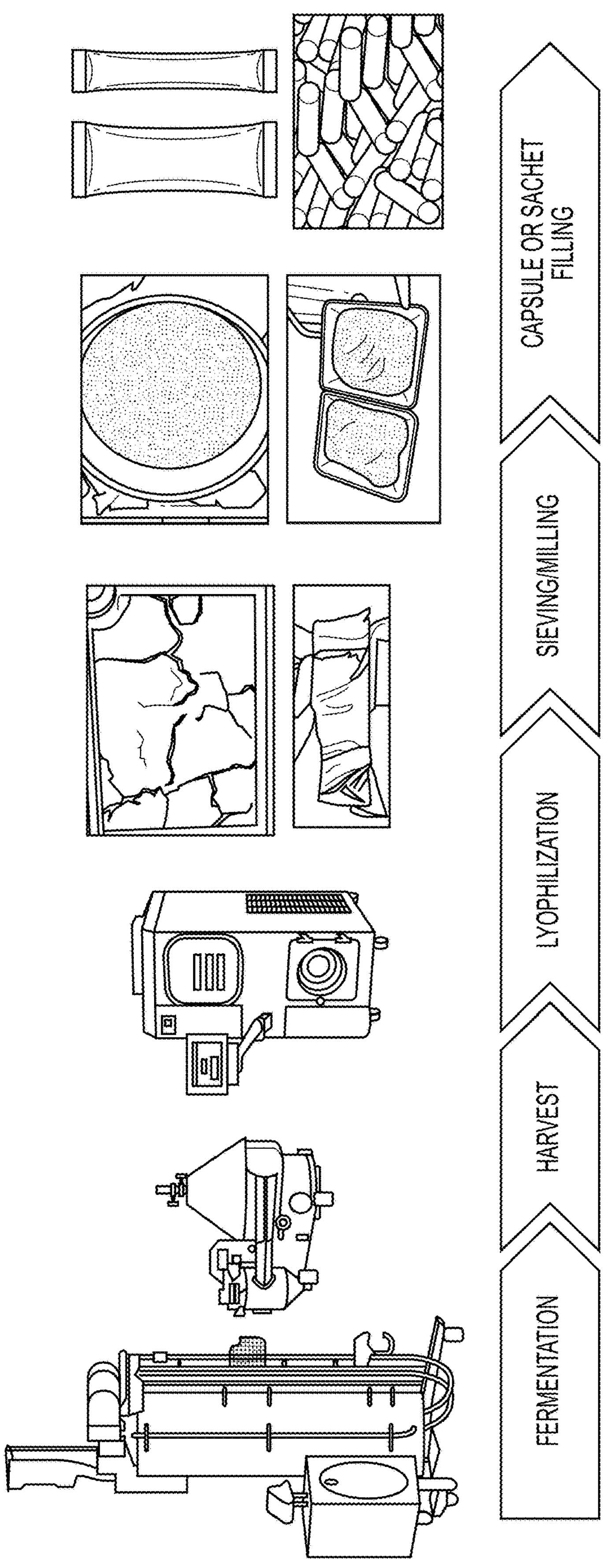
FIG. 2 depicts a schematic for a process of manufacturing pharmaceutical compositions comprising engineered microorganisms, e.g., genetically engineered bacteria.
Figure 3:
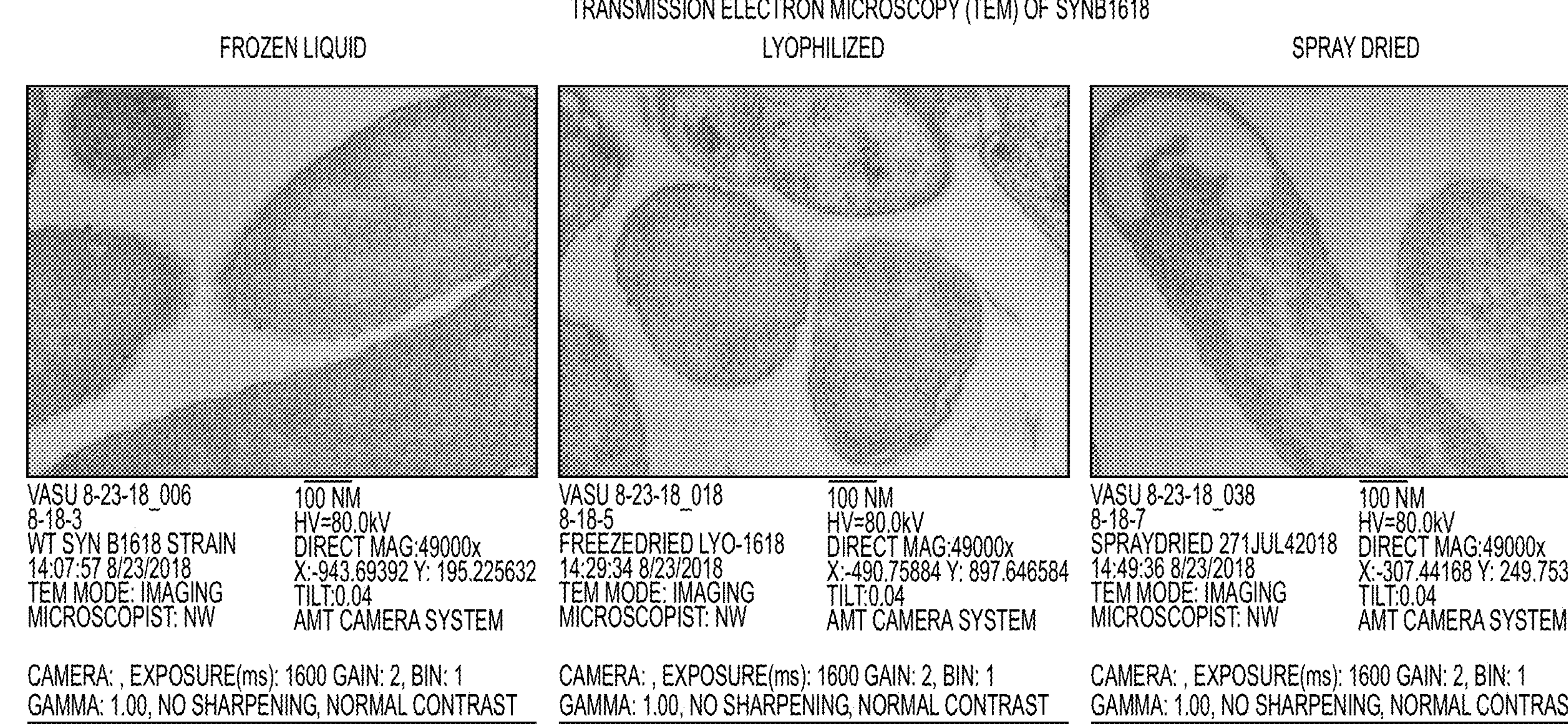
FIG. 3 depicts transmission electron microscopy (TEM) images of genetically engineered bacteria that have been frozen, lyophilized, or spray dried. The table shows the total cell count, live cell count, and CFU count for bacterial compositions that have been frozen, lyophilized or spray dried. Methods for characterizing the plasma membrane integrity of bacteria using TEM are known in the art. See, e.g., Tian et al., (2005) "Kinetic studies of polyhydroxybutyrate granule formation in *Wautersia eutropha* H16 by transmission electron microscopy," the contents of which are hereby incorporated by reference in their entirety.
Figures 4A, 4B:
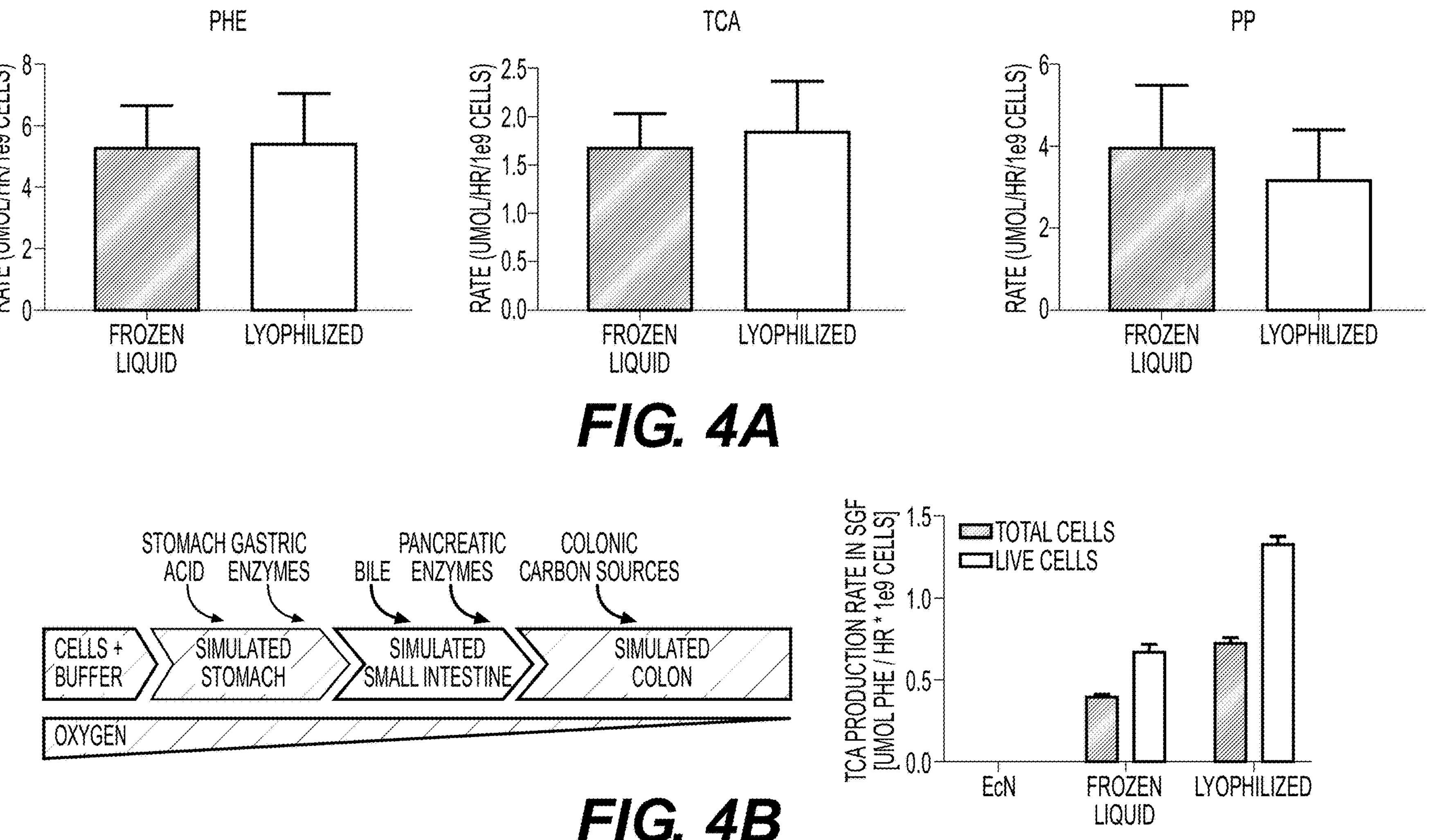
FIG. 4A depicts graphs illustrating the rate at which phenylalanine is consumed and TCA and phenylpyruvate (PP) are produced in vitro. Rates are normalized to the number of cells.
FIG. 4B includes a schematic depicting the In Vitro Simulated (IVS) gut model used for simulating the gastrointestinal tract as well as a graph showing TCA production by a wild-type *E. coli* Nissle strain (EcN) as compared to bacteria (frozen or lyophilized) genetically engineered to metabolize phenylalanine. Rates are shown normalized to the total number of cells and the number of live cells.
Figure 4C:
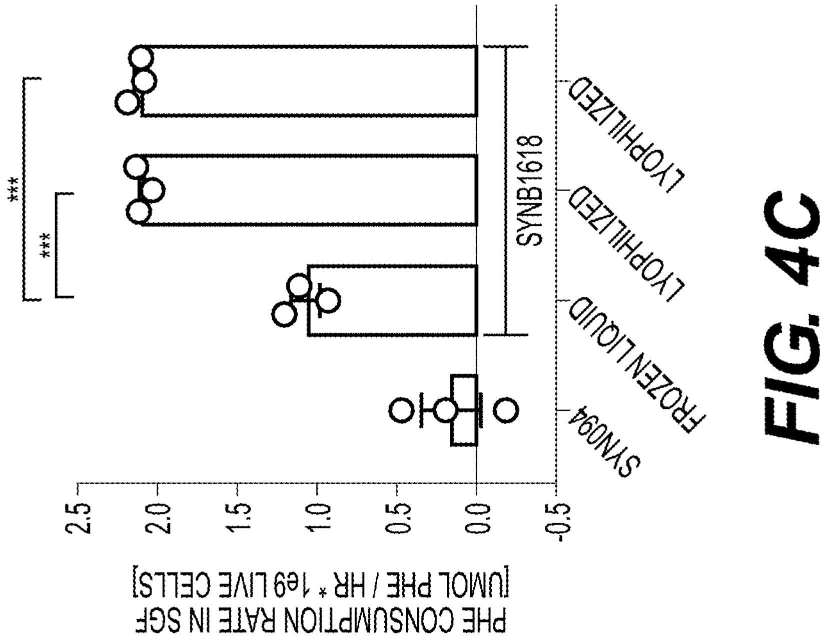
FIG. 4C depicts a bar graph showing the rate at which Phe is consumed in simulated gut fluid (SGF) by unmodified *E. coli* Nissle (SYN094) and bacteria genetically engineered to metabolize phenylalanine (SYNB1618) (frozen, lyophilized, or spray dried).

The present disclosure relates to, inter alia, engineered microorganisms, e.g., genetically engineered bacteria, comprising one or more gene(s) for producing a desired therapeutic molecule and compositions and formulations thereof; methods for characterizing, dosing, and/or assaying the activity of the bacteria, compositions, and formulations, e.g., using a live cell counting method; methods for manufacturing bacteria, compositions, and formulations that are measured using methods for characterizing, dosing, and/or assaying the activity, e.g., the live cell counting method; and methods for treating a disease or disorder by administering the bacteria, compositions, and formulations that are measured using methods for characterizing, dosing, and/or assaying the activity, e.g., using a live cell counting method. In one aspect, the live cell counting method captures both dividing cells as well as non-dividing cells, e.g., genetically engineered bacterial cells. Bacteria may be living and dividing, living and non-dividing, or non-living and non-dividing (e.g., dead). In some embodiments, the methods, e.g., live cell counting methods, provide a more accurate measure of bacterial activity, dosing, and/or therapeutic efficacy as compared to a CFU method. In some embodiments, the methods, e.g., live cell counting methods, provide a more efficient method for manufacturing and dosing bacteria as compared to the CFU method.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, a "live cell count method" or "live cell counting method" refers to a method, e.g., a microscopic method, for determining the number of living cells, e.g., bacterial cells, present in a sample. In some embodiments, the live cell counting method uses fluorescent dyes to distinguish living from non-living cells. "Live cell count" refers to the number of living cells present in a sample as determined by a live cell counting method. In some embodiments, the live cell count includes living dividing cells as well as and living non-dividing cells. In some embodiments, the live cell count, e.g., of a pharmaceutical composition, provides a more accurate measure of a desired cell activity than CFU count.

As used herein, a "living" or "live" cell refers to a cell that has (1) an intact membrane, e.g., exhibits a membrane permeability that is roughly similar to that of dividing cells, (2) a reducing intracellular environment relative to the extracellular environment (whereas a non-living cell may have an intracellular reducing environment that is indistinguishable from that of the extracellular space), (3) the ability to maintain a membrane potential, and/or (4) the ability to maintain a proton gradient. In some embodiments, a living cell has an intact membrane, e.g., exhibits a membrane permeability that is roughly similar to that a suitable control, e.g., dividing cells. In some embodiments, a living cell has an intact membrane, e.g., exhibits a membrane permeability that is roughly similar to that of a suitable control, and has the ability to maintain a membrane potential. A "non-living" cell refers to a cell that lacks one or more of the above characteristics, e.g., has compromised cell membrane integrity. In some embodiments, live cells include dividing cells as well as non-dividing cells, but exclude non-living, non-dividing cells (e.g., a non-live, non-dividing cell with compromised cell membrane integrity). In some embodiments, plasma membrane integrity may be characterized using transmission electron microscopy (TEM), methods for which are known in the art. See, e.g., Tian et al., (2005) "Kinetic studies of polyhydroxybutyrate granule formation in *Wautersia eutropha* H16 by transmission electron microscopy," the contents of which are hereby incorporated by reference in their entirety. In some embodiments, plasma membrane integrity may be characterized based on permeability to a fluorescent dye, where only cells having compromised cell membrane integrity will exhibit dye permeability.

As used herein, "percent living" or "percent viable" refers to the number of live cells divided by the total number of cells.

As used herein, "dividing cells" refer to cells that are capable of dividing, e.g., cells that form bacterial colonies when plated on solid media. "Non-dividing cells" refer to cells that are not capable of dividing, e.g., cells that do not form bacterial colonies when plated on solid media. In some embodiments, non-dividing cells may be living cells. In some embodiments, non-dividing cells, e.g., bacterial cells in a pharmaceutical composition, may be capable of producing a therapeutic molecule. Therefore, counting the number of living dividing cells as well as living non-dividing cells, e.g., in a therapeutic bacterial composition, may provide a more accurate measure of the activity than other methods, e.g., CFU. In some embodiments, living, non-dividing cells are active with respect to the ability to produce a desired molecule, e.g., phenylalanine ammonia lyase, despite the inability to divide. In some embodiments, living non-dividing cells may have a reducing environment, maintain plasma membrane potential, and/or have functional metabolism, etc.

As used herein, "total cells" refers to the sum of living and non-living cells in a sample.

In some embodiments, the engineered microorganisms, e.g., genetically engineered bacteria, of the disclosure comprise one or more gene(s), e.g., non-native gene(s), for the treatment of a disease or disorder. In some embodiments, the one or more gene(s) encode a desired molecule, e.g., a therapeutic molecule, e.g., a phenylalanine-metabolizing enzyme. In some embodiments, the genes encode a biosynthetic pathway for producing a desired molecule, e.g., a therapeutic molecule, e.g., butyrate, and may be referred to as a gene cassette.

As used herein, a "therapeutic" molecule, e.g., protein, refers to a molecule that is capable of producing a therapeutic effect in a subject. For example, a therapeutic molecule such as IL-10 may be capable of reducing inflammation in a subject. In some embodiments, the therapeutic molecule is capable of reducing one or more deleterious molecules in the subject, e.g., a phenylalanine-metabolizing enzyme is capable of metabolizing excess and deleterious phenylalanine in a subject with PKU. In some embodiments, the engineered microorganisms, e.g., genetically engineered bacteria, disclosed herein expresses one or more therapeutic molecule(s). In some embodiments, the engineered microorganisms disclosed herein, e.g., genetically engineered bacteria, express one or more therapeutic molecule(s) prior to administration to a subject. In some embodiments, the engineered microorganisms disclosed herein, e.g., genetically engineered bacteria, express one or more therapeutic molecule(s) after administration to a subject, e.g., the gene (s) for producing the therapeutic molecule are induced after administration to the subject.

As used herein, "activity" refers to a desired parameter, e.g., output of a molecule, of a cell or composition, e.g., a bacterium or a bacterial composition. In some embodiments, "therapeutic activity" refers to the production of a desired therapeutic molecule from the cell, e.g., as measured in vitro or in vivo in a cellular model, animal model, or human patient. In some embodiments, activity refers to the amount or function of a desired therapeutic molecule from the cell. In some embodiments, activity refers to the rate at which one or more desired therapeutic molecules is produced. In some embodiments, activity refers to the rate at which one or more deleterious compounds, e.g. a deleterious compound outside of the cell, is metabolized or reduced, e.g., as measured by levels of the deleterious compound or an intermediate.

In some embodiments, "potency" refers to the activity for a population or predetermined number of cells, e.g., as determined by CFU count, total cell count, or live cell count. In some embodiments, potency refers to the activity multiplied by the number of cells, e.g., in a composition. In some embodiments, potency refers to the activity observed for a predetermined mass of cells, e.g., weight. In some embodiments, potency refers to the activity observed for a predetermined volume of cells.

As used herein, "accuracy" refers to the degree to which a measurement, e.g., a cell count, is correlated to activity as described herein. In some embodiments, live cell count of the engineered microorganisms, e.g., genetically engineered bacteria, disclosed herein, provides a more accurate measure of activity, e.g., therapeutic molecule function, as compared to CFU count. In some embodiments, live cell counting better, e.g., more accurately, reflects the activity, the therapeutic activity, and/or the therapeutic efficacy in a subject than CFU counting. Thus, in some embodiments, dosing by live cell counting is improved, e.g., more accurate, than CFU counting As used herein, "CFU" refers to colony forming unit as determined by a CFU counting method. "CFU count" refers to the number of CFUs present in a sample. Without being bound by theory, a CFU is formed by roughly one dividing cell, and hence a CFU count is generally viewed as a measure of the number of dividing cells present in a composition. In general, CFU count includes living dividing cells but excludes living non-dividing cell.

As used herein, the "stability" of a bacterial composition refers to the relative degree to which the composition changes over a given period of time. In some embodiments, the stability of a composition is defined by the change in the number of living cells over a given period of time. In some embodiments, the stability of a composition refers to changes in activity over a given period of time.

"Phenylalanine" and "Phe" are used to refer to an amino acid with the formula $C_6H_5CH_2CH(NH_2)COOH$. Phenylalanine is a precursor for tyrosine, dopamine, norepinephrine, and epinephrine. L-phenylalanine is an essential amino acid and the form of phenylalanine primarily found in dietary protein; the stereoisomer D-phenylalanine is found is lower amounts in dietary protein; DL-phenylalanine is a combination of both forms. Phenylalanine may refer to one or more of L-phenylalanine, D-phenylalanine, and DL-phenylalanine.

"Phenylalanine metabolizing enzyme" or "PME" are used to refer to an enzyme which is able to degrade phenylalanine. Any phenylalanine metabolizing enzyme known in the art may be encoded by the engineered microorganisms, genetically engineered bacteria. PMEs include, but are not limited to, phenylalanine hydroxylase (PAH), phenylalanine ammonia lyase (PAL), aminotransferase, L-amino acid deaminase (LAAD), and phenylalanine dehydrogenases.

"Phenylalanine ammonia lyase" and "PAL" are used to refer to a phenylalanine metabolizing enzyme (PME) that converts or processes phenylalanine to trans-cinnamic acid and ammonia. Trans-cinnamic acid has low toxicity and is converted by liver enzymes in mammals to hippuric acid, which is secreted in the urine. PAL may be substituted for the enzyme PAH to metabolize excess phenylalanine. PAL enzyme activity does not require THB cofactor activity. In some embodiments, PAL is encoded by a PAL gene derived from a prokaryotic species. In alternate embodiments, PAL is encoded by a PAL gene derived from a eukaryotic species. In some embodiments, PAL is encoded by a PAL gene derived from a bacterial species, including but not limited to, *Achromobacter xylosoxidans, Pseudomonas aeruginosa, Photorhabdus luminescens, Anabaena variabilis*, and *Agrobacterium tumefaciens*. In some embodiments, PAL is encoded by a PAL gene derived from *Anabaena variabilis* and referred to as "PAL1" herein (Moffitt et al., 2007). In some embodiments, PAL is encoded by a PAL gene derived from *Photorhabdus luminescens* and referred to as "PAL3" herein (Williams et al., 2005). In some embodiments, PAL is encoded by a PAL gene derived from a yeast species, e.g., *Rhodosporidium toruloides* (Gilbert et al., 1985). In some embodiments, PAL is encoded by a PAL gene derived from a plant species, e.g., *Arabidopsis thaliana* (Wanner et al., 1995). Any suitable nucleotide and amino acid sequences of PAL, or functional fragments thereof, may be used.

"L-Aminoacid Deaminase" and "LAAD" are used to refer to an enzyme that catalyzes the stereospecific oxidative deamination of L-amino acids to generate their respective keto acids, ammonia, and hydrogen peroxide. For example, LAAD catalyzes the conversion of phenylalanine to phenylpyruvate. Multiple LAAD enzymes are known in the art, many of which are derived from bacteria, such as *Proteus, Providencia*, and *Morganella*, or venom. LAAD is characterized by fast reaction rate of phenylalanine degradation (Hou et al., Appl Microbiol Technol. 2015 October; 99(20): 8391-402; "Production of phenylpyruvic acid from L-phenylalanine using an L-amino acid deaminase from *Proteus mirabilis*: comparison of enzymatic and whole-cell biotransformation approaches"). Most eukaryotic and prokaryotic L-amino acid deaminases are extracellular; however, *Proteus* species LAAD are localized to the plasma membrane (inner membrane), facing outward into the periplasmic space, in which the enzymatic activity resides. As a consequence of this localization, phenylalanine transport through the inner membrane into the cytoplasm is not required for *Proteus* LAAD mediated phenylalanine degradation. Phenylalanine is readily taken up through the outer membrane into the periplasm without a transporter, eliminating the need for a transporter to improve substrate availability.

In some embodiments, the engineered microorganisms, e.g., genetically engineered bacteria, comprise a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the LAAD encoded by the engineered microorganisms, e.g., genetically engineered bacteria, is localized to the plasma membrane, facing into the periplasmic space and with the catalytic activity occurring in the periplasmic space.

As used herein, the term "transporter" is meant to refer to a mechanism, e.g., protein or proteins, for importing a molecule, e.g., amino acid, toxin, metabolite, substrate, etc. into the microorganism from the extracellular milieu. For example, a phenylalanine transporter such as PheP imports phenylalanine into the microorganism.

"Phenylalanine transporter" is used to refer to a membrane transport protein that is capable of transporting phenylalanine into bacterial cells (see, e.g., Pi et al., 1991). In *Escherichia coli*, the pheP gene encodes a high affinity phenylalanine-specific permease responsible for phenylalanine transport (Pi et al., 1998). In some embodiments, the phenylalanine transporter is encoded by a pheP gene derived from a bacterial species, including but not limited to, *Acinetobacter calcoaceticus, Salmonella enterica*, and *Escherichia coli*. Other phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by a aroP gene derived from a bacterial species. In some embodiments, the phenylalanine transporter is encoded by LIV-binding protein and LS-binding protein and LivHMGF genes derived from a bacterial species. In some embodiments, the engineered microorganisms, e.g., genetically engineered bacteria, comprise more than one type of phenylalanine transporter, selected from pheP, aroP, and the LIV-I/LS system.

"Phenylalanine metabolite" refers to a metabolite that is generated as a result of the degradation of phenylalanine. The metabolite may be generated directly from phenylalanine, by the enzyme using phenylalanine as a substrate, or indirectly by a different enzyme downstream in the metabolic pathway, which acts on a phenylalanine metabolite substrate. In some embodiments, phenylalanine metabolites are produced by the engineered microorganisms, e.g. genetically engineered bacteria, encoding a PME.

"Hyperammonemia," "hyperammonemic," or "excess ammonia" is used to refer to increased concentrations of ammonia in the body. Hyperammonemia is caused by decreased detoxification and/or increased production of ammonia. Decreased detoxification may result from urea cycle disorders (UCDs), such as argininosuccinic aciduria, arginase deficiency, carbamoylphosphate synthetase deficiency, citrullinemia, N-acetylglutamate synthetase deficiency, and ornithine transcarbamylase deficiency; or from bypass of the liver, e.g., open ductus *hepaticus*; and/or deficiencies in glutamine synthetase. See, e.g., Hoffman et al., 2013; Häberle et al., 2013. Increased production of ammonia may result from infections, drugs, neurogenic bladder, and intestinal bacterial overgrowth. See, e.g., Häberle et al., 2013. Increased production of ammonia may also be associated with a tumor microenvironment. See, e.g., Spinelli et al., 2017. Other disorders and conditions associated with hyperammonemia include, but are not limited to, liver disorders such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; and chemotherapy. See, e.g., Hoffman et al., 2013; Häberle et al., 2013; Pham et al., 2013; Lazier et al., 2014. In healthy subjects, plasma ammonia concentrations are typically less than about 50 μmol/L. See, e.g., Leonard, 2006. In some embodiments, a diagnostic signal of hyperammonemia is a plasma ammonia concentration of at least about 50 μmol/L, at least about 80 μmol/L, at least about 150 μmol/L, at least about 180 μmol/L, or at least about 200 μmol/L. See, e.g., Leonard, 2006; Hoffman et al., 2013; Häberle et al., 2013. Methods of modifying arginine biosynthesis, e.g., in engineered microorganisms, e.g., genetically engineered bacteria, to reduce hyperammonemia, e.g., by deleting the arginine repressor, modifying the arginine repressor binding sites, and/or using arginine feedback resistant N-acetylglutamate synthase, are known in the art. See, e.g., WO2016200614, the contents of which are hereby incorporated by reference.

An "anti-cancer molecule" refers to one or more therapeutic substances or drugs of interest to be produced by an engineered microorganism, e.g., engineered bacterium, which are capable of reducing and/or inhibiting cell growth or replication. In some embodiments, the anti-cancer molecule is a therapeutic molecule that is useful for modulating or treating a cancer. In some embodiments, the anti-cancer molecule is a therapeutic molecule encoded by a gene. In alternate embodiments, the anti-cancer molecule is a therapeutic molecule produced by a biochemical or biosynthetic pathway, wherein the biosynthetic or biochemical pathway may optionally be endogenous to the microorganism. In some embodiments, the genetically engineered microorganism is capable of producing two or more anti-cancer molecules. Non-limiting examples of anti-cancer molecules include immune checkpoint inhibitors (e.g., CTLA-4 antibodies, PD-1 antibodies, PDL-1 antibodies), cytotoxic agents (e.g., Cly A, FASL, TRAIL, TNF-alpha), immunostimulatory cytokines and co-stimulatory molecules (e.g., OX40, CD28, ICOS, CCL21, IL-2, IL-18, IL-15, IL-12, IFN-gamma, IL-21, TNFs, GM-CSF), antigens and antibodies (e.g., tumor antigens, neoantigens, CtxB-PSA fusion protein, CPV-OmpA fusion protein, NY-ESO-1 tumor antigen, RAF1, antibodies against immune suppressor molecules, anti-VEGF, Anti-CXR4/CXCL12, anti-GLP1, anti-GLP2, anti-galectin1, anti-galectin3, anti-Tie2, anti-CD47, antibodies against immune checkpoints, antibodies against immunosuppressive cytokines and chemokines), DNA transfer vectors (e.g., endostatin, thrombospondin-1, TRAIL, SMAC, Stat3, Bcl2, FLT3L, GM-CSF, IL-12, AFP, VEGFR2), and enzymes (e.g., *E. coli* CD, HSV-TK). In some embodiments, the anti-cancer molecule includes nucleic acid molecules that mediate RNA interference, microRNA response or inhibition, TLR response, antisense gene regulation, target protein binding (aptamer or decoy oligos), gene editing, such as CRISPR interference. In some embodiments, bacteria or virus can be used as vectors to transfer DNA into mammalian cells, e.g., by bactofection. See, e.g., Bernardes et al., 2013. Engineered microorganisms, e.g., genetically engineered bacteria, that are capable of producing an anti-cancer molecule, e.g., a deadenylate cyclase gene (e.g., dacA from *Listeria monocytogenes*) or an enzyme capable of producing a stimulator of interferon gene (STING) agonist, are known in the art. See, e.g., WO2018129404, the contents of which are hereby incorporated by reference.

"Operably linked" refers a nucleic acid sequence, e.g., a gene encoding PAL, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

An "inducible promoter" refers to a regulatory region that is operably linked to one or more genes, wherein expression of the gene(s) is increased in the presence of an inducer of said regulatory region.

In some embodiments, the engineered microorganisms, e.g., genetically engineered bacteria, comprise one or more gene(s) whose expression is controlled by a temperature sensitive mechanism. Thermoregulators are advantageous because of strong transcriptional control without the use of external chemicals or specialized media (see, e.g., Nemani et al., Magnetic nanoparticle hyperthermia induced cytosine deaminase expression in microencapsulated *E. coli* for enzyme-prodrug therapy; J Biotechnol. 2015 Jun. 10; 203:

32-40, and references therein). Thermoregulated protein expression using the mutant cI857 repressor and the pL and/or pR phage λ, promoters may be used to engineer recombinant bacterial strains. The gene of interest is cloned downstream of the λ, promoters and can be efficiently regulated by the mutant thermolabile cI857 repressor of bacteriophage λ. At temperatures below 37° C., cI857 binds to the oL or oR regions of the pR promoter and blocks transcription by RNA polymerase. At higher temperatures, the functional cI857 dimer is destabilized, binding to the oL or oR DNA sequences is abrogated, and mRNA transcription is initiated.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., WO2017087580; Castiglione et al., 2009; Eiglmeier et al., 1989; Galimand et al., 1991; Hasegawa et al., 1998; Hoeren et al., 1993; Salmon et al., 2003). In some embodiments, the FNR-responsive promoter is PfnrS derived from the *E. coli* Nissle fumarate and nitrate reductase gene S(fnrS) that is known to be highly expressed under conditions of low or no environmental oxygen (Durand and Storz, 2010; Boysen et al, 2010).

PMEs and phenylalanine transporters, as well as the nucleotide and amino acid sequences of representative examples of such enzymes and transporters, as well as exemplary promoters, are provided in WO2016183531A1 and WO2017087580A1, the contents of which are hereby incorporated by reference in their entirety. Any suitable enzymes and/or phenylalanine transporters may be used in the engineered microorganisms, e.g., genetically engineered bacteria, of the disclosure. In one embodiment, expression of one or more PME(s), e.g., PAL and/or LAAD, and/or Phe transporter(s), e.g., PheP, and/or transcriptional regulator(s), e.g., FNRS24Y, is driven by one or more thermoregulated promoter(s).

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence. See, e.g., Purcell et al., 2013, Towards a whole-cell modeling approach for synthetic biology. The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. In some embodiments, the engineered microorganisms, e.g., genetically engineered bacteria, are engineered to comprise multiple copies of the same regulatory region, promoter, gene, and/or gene cassette in order to enhance copy number or to comprise multiple different components of a gene cassette performing multiple different functions. In some embodiments, the engineered microorganisms, e.g., genetically engineered bacteria, of the invention comprise a gene encoding a phenylalanine-metabolizing enzyme that is operably linked to a inducible promoter that is not associated with said gene in nature, e.g., an FNR promoter operably linked to a gene encoding PAL or a ParaBAD promoter operably linked to LAAD.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines. In some embodiments, the engineered microorganisms, e.g., genetically engineered bacteria, are active (e.g., express one or more heterologous genes) in the gut. In some embodiments, the engineered microorganisms, e.g., genetically engineered bacteria, are active (e.g., express one or more heterologous genes) in the large intestine. In some embodiments, the engineered microorganisms, e.g., genetically engineered bacteria, are active (e.g., express one or more heterologous genes) in the small intestine. In some embodiments, the engineered microorganisms, e.g., genetically engineered bacteria, are active in the small intestine and in the large intestine.

As used herein, the term "gene" or "gene sequence" is meant to refer to a genetic sequence, e.g., a nucleic acid sequence. The gene, gene sequence or genetic sequence is meant to include a complete gene sequence or a partial gene sequence. The gene, gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, yeast, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

"Non-pathogenic" refers to microorganisms, for example bacteria, that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia,*

*Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, *Bifidobacteria, Escherichia, Lactobacillus*, and *Saccharomyces*, e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, the terms "treat" and "modulate" and their cognates refer to an amelioration of a disease, disorder, and/or condition, or at least one discernible symptom thereof. In another embodiment, "treat" and "modulate" refer to an amelioration of at least one measurable physical parameter, not necessarily discernible by the patient. In another embodiment, "treat" and "modulate" refer to inhibiting the progression of a disease, disorder, and/or condition, either physically (e.g., stabilization of a discernible symptom), physiologically (e.g., stabilization of a physical parameter), or both. In another embodiment, "treat" and "modulate" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. For example, primary hyperphenylalaninemia, e.g., PKU, is caused by inborn genetic mutations for which there are no known cures, and hyperphenylalaninemia can also be secondary to other conditions, e.g., liver diseases. Treatment may encompass reducing or eliminating one or more disease features, e.g., excess phenylalanine in primary hyperphenylalaninemia, and does not necessarily encompass the elimination of the underlying disease.

As used herein a "pharmaceutical composition" refers to a preparation of engineered microorganisms, e.g., genetically engineered bacteria, of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperphenylalaninemia. A therapeutically effective amount may, for example, be sufficient to treat, prevent, reduce the severity, delay the onset, and/or reduce the risk of occurrence of one or more symptoms of a disease or condition associated with excess phenylalanine levels. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the engineered microorganisms, e.g., genetically engineered bacteria or virus, of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Live Cell Counting

The disclosure relates to engineered microorganisms, e.g., genetically engineered bacteria, comprising one or more gene(s) for producing a desired therapeutic molecule and compositions and formulations thereof. In one aspect, methods for characterizing, dosing, and determining the activity of the bacteria, compositions, and formulations, e.g., using live cell counting methods, are provided. The live cell counting method may be used to determine the number of living cells present in a bacterial sample. Specifically, live cell counting methods may be used to determine the number of living engineered microorganisms, e.g., genetically engineered bacterial cells, and to dose and/or determine the activity of the engineered microorganisms, e.g., genetically engineered bacteria.

In some embodiments, live cell counting provides the number of living cells, e.g., bacterial cells, with (1) intact membranes, (2) reducing intracellular environment relative to the extracellular environment, (3) the ability to maintain membrane potential, and/or (4) the ability to maintain proton gradient. In some embodiments, the live cell counting method captures living dividing cells and living non-dividing cells. By contrast, the CFU method includes living dividing cells but excludes living non-dividing cells. In some embodiments, live cell counting provides the number of living cells, e.g., bacterial cells, with intact membranes, e.g., exhibits a membrane permeability that is roughly similar to that of a suitable control.

The engineered microorganisms, e.g., genetically engineered bacteria, disclosed herein, are capable of producing one or more desired therapeutic molecules, e.g., an IL-22 molecule capable of reducing inflammation in a subject or a phenylalanine-metabolizing enzyme capable of metabolizing deleterious phenylalanine in a subject with PKU. In some embodiments, the activity of the engineered microorganisms, e.g., genetically engineered bacteria, may be measured by a desired parameter, e.g., the production or the function of the desired therapeutic molecule. In some embodiments, activity refers to the production of a desired therapeutic molecule in the engineered microorganisms, e.g., genetically engineered bacteria. In some embodiments, activity refers to the amount or function of a desired therapeutic molecule in the engineered microorganisms, e.g., genetically engineered bacteria. In some embodiments, activity refers to the rate at which one or more desired therapeutic molecules is produced. In some embodiments, activity refers to the rate at which one or more deleterious compounds is metabolized or reduced, e.g., as measured by levels of the deleterious compound or an intermediate. The present disclosure demonstrates that living non-dividing cells—which are captured by the live cell counting method but not by the CFU method—remain capable of yielding such desired parameters. For example, a living non-dividing cell may be capable of producing a desired phenylalanine-metabolizing enzyme and/or reducing excess phenylalanine (in an in vitro model, in vivo model, or a human subject) despite not being able to divide and form colonies. Thus, in some embodiments, the live cell counting method provides a more accurate measure of the activity of bacteria than the CFU method. In some embodiments, the live cell counting method provides reduced CFU count as compared to the CFU method. In some embodiments, the live cell counting method allows for reducing the CFU count, e.g., for lyophilizing the bacteria or freezing the bacteria in liquid, as compared to the CFU method.

In some embodiments, live cell count is determined using microscopy (e.g., by intact membrane, e.g., by transmission electron microscopy), cellometer, and/or other methods known in the art. In some embodiments, live cell count is determined using a fluorescent dye that is capable of selectively identifying living or non-living cells. In some embodiments, the fluorescent dye selectively accumulates in living or non-living cells, thus allowing the identification of living or non-living cells. In some embodiments, the fluorescent dye becomes substantially more fluorescent only in living or non-living cells, thus allowing the identification of living or non-living cells. In some embodiments, non-living cells are distinguished from living cells using fluorescent dyes that are not permeable to the cell membrane. In some embodiments, living cells are distinguished from non-living cells using fluorescent dyes capable of selectively identifying cells with a proton gradient. In some embodiments, the live cell count of a composition can be determined by subtracting the number of non-living cells from the number of total cells. In some embodiments, the fluorescent dye is Sytox green stain.

In some embodiments, live cell count provides a more accurate measure of amount or the function of a desired therapeutic molecule in the engineered microorganisms, e.g., genetically engineered bacteria. In some embodiments, live cell count provides a more accurate measure of the enzymatic activity of a desired therapeutic molecule. In some embodiments, live cell count provides a more accurate measure of therapeutic efficacy of the engineered microorganisms, e.g., genetically engineered bacteria, in vitro. In some embodiments, live cell count provides a more accurate measure of therapeutic efficacy of the engineered microorganisms, e.g., genetically engineered bacteria in vivo, e.g., in an animal model or a human subject. Therapeutic efficacy may refer to the reduction of one or more deleterious compounds, e.g., the rate at which such compounds are reduced or metabolized, e.g., as measured by level of the deleterious compounds or intermediates from the metabolism of the deleterious compounds.

Exemplary microorganisms, e.g., bacteria, and compositions and formulations that may be assayed and/or dosed according to the present disclosure are provided in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety.

In some embodiments, the engineered microorganisms, e.g., genetically engineered bacteria, to be assayed, e.g., using the live cell counting method, are non-pathogenic bacteria, commensal bacteria, or probiotic bacteria. In some embodiments, the engineered microorganisms, e.g., genetically engineered bacteria, to be assayed, e.g., using the live cell counting method, comprise at least one gene for producing an anti-cancer molecule, e.g., a deadenylate cyclase gene or an enzyme capable of producing a STING agonist. In some embodiments, the engineered microorganisms, e.g., genetically engineered bacteria, to be assayed, e.g., using the live cell counting method, comprises gene(s) encoding a modified arginine biosynthesis pathway, e.g., deleted arginine repressor, modified arginine repressor binding sites, and/or arginine feedback resistant N-acetylglutamate synthase mutation. In some embodiments, the engineered microorganisms, e.g., genetically engineered bacteria, to be assayed, e.g., using the live cell counting method, comprise a gene encoding at least one PME, e.g., PAL and/or LAAD, optionally wherein the PME gene is operably linked to an inducible promoter. In some embodiments, the engineered microorganisms, e.g., genetically engineered bacteria, to be assayed, e.g., using the live cell counting method, comprise a non-native PME gene, e.g., additional copies of a native PME gene. In some embodiments, the promoter is not associated with the PME gene in nature. In some embodiments, the engineered microorganisms, e.g. genetically engineered bacteria, to be assayed using, e.g., the live cell counting method, further comprise a phenylalanine transporter, e.g., PheP. In some embodiments, the engineered microorganisms, e.g., genetically engineered bacteria, to be assayed using, e.g., the live cell counting method, comprise a non-native phenylalanine transporter gene, e.g., additional copies of a native phenylalanine transporter gene. In some embodiments, the promoter is not associated with the phenylalanine transporter gene in nature. In some embodiments, the promoter is a thermoregulated promoter or a promoter induced under low-oxygen or anaerobic conditions. In some embodiments, the engineered microorganisms, e.g., genetically engineered bacteria, to be assayed, e.g., using the live cell counting method, are auxotrophs for one or more essential genes, e.g., thyA or dapA. In some embodiments, the inducible promoters are induced prior to administration to the subject. In some embodiments, the inducible promoters are induced after administration to the subject.

In some embodiments, the disclosure provides methods for determining the activity of a composition or formulation comprising the engineered microorganisms, e.g., genetically engineered bacteria, disclosed herein and at least one pharmaceutically acceptable excipient. In some embodiments, the composition or formulation comprises 1-20% trehalose, 1-10% trehalose, 5-15% trehalose, 7-13% trehalose, 9-11% trehalose, or about 10% trehalose in a biological buffer covering a pH range of 6-8, where the biological buffer may be PIPES, MOPS, HEPES, and/or Tris buffer. In some embodiments, the composition or formulation comprises 1-400 mM Tris buffer. In some embodiments, the composition or formulation comprises 1-300 mM Tris buffer. In some embodiments, the composition or formulation comprises 1-200 mM Tris buffer. In some embodiments, the composition or formulation comprises 1-100 mM Tris buffer. In some embodiments, the composition or formulation comprises 1-50 mM Tris buffer. In some embodiments, the composition or formulation comprises 1-10 mM Tris buffer.

In some embodiments, the disclosure provides methods for measuring the activity of a composition comprising lyophilized bacteria. In some embodiments, the percent water content of the lyophilized bacteria is approximately 1-10%. In some embodiments, the percent water content is approximately 3-8%. In some embodiments, the percent water content is approximately 3-6%. In some embodiments, the percent water content is approximately 3-5%. In some embodiments, the percent water content is approximately 3%, approximately 4%, or approximately 5%.

Method of Manufacturing

In some embodiments, the engineered microorganisms, e.g., genetically engineered bacteria, comprising one or more therapeutic gene(s) and compositions and formulations thereof are manufactured using the methods for characterizing, dosing, and determining the activity disclosed herein, e.g., live cell counting. Exemplary microorganisms, e.g., bacteria, and compositions and formulations that may be manufactured according to the present disclosure are provided in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety.

In some embodiments, the disclosure provides a method for manufacturing engineered microorganisms, e.g., genetically engineered bacteria, that are non-pathogenic, commensal, or probiotic measured using, e.g., the live cell counting method. In some embodiments, the disclosure provides a method for manufacturing engineered microorganisms, e.g., genetically engineered bacteria, that comprise at least one gene for producing an anti-cancer molecule, e.g., a deadenylate cyclase gene (e.g., dacA) or an enzyme capable of producing a STING agonist. In some embodiments, the disclosure provides a method for manufacturing engineered microorganisms, e.g., genetically engineered bacteria, that comprise gene(s) encoding a modified arginine biosynthesis pathway, e.g., deleted arginine repressor, modified arginine repressor binding sites, and/or arginine feedback resistant N-acetylglutamate synthase mutation. In some embodiments, the disclosure provides a method for manufacturing engineered microorganisms, e.g., genetically engineered bacteria, that comprise a gene encoding at least one PME, e.g., PAL and/or LAAD, optionally wherein the PME gene is operably linked to an inducible promoter. In some embodiments, the bacteria manufactured by the methods disclosed herein comprise a non-native PME gene, e.g., additional copies of a native PME gene. In some embodiments, the promoter is not associated with the PME gene in nature. In some embodiments, the bacteria manufactured by the methods disclosed herein further comprises a phenylalanine transporter, e.g., PheP. In some embodiments, the bacteria manufactured by the methods disclosed herein comprise a non-native phenylalanine transporter gene, e.g., additional copies of a native phenylalanine transporter gene. In some embodiments, the promoter is not associated with the phenylalanine transporter gene in nature. In some embodiments, the promoter is a thermoregulated promoter or a promoter induced under low-oxygen or anaerobic conditions. In some embodiments, the inducible promoters are induced prior to administration to the subject. In some embodiments, the inducible promoters are induced after administration to the subject. In some embodiments, the bacteria manufactured by the methods disclosed herein are auxotrophs for one or more essential genes, e.g., thyA or dapA.

In some embodiments, the disclosure provides a method for manufacturing a pharmaceutical composition comprising 1-20% trehalose, 1-10% trehalose, 5-15% trehalose, 7-13% trehalose, 9-11% trehalose, or about 10% trehalose in a biological buffer covering a pH range of 6-8, where the biological buffer may be PIPES, MOPS, HEPES, and/or Tris buffer. In some embodiments, the composition or formulation comprises 1-400 mM Tris buffer. In some embodiments, the composition or formulation comprises 1-300 mM Tris buffer. In some embodiments, the composition or formulation comprises 1-200 mM Tris buffer. In some embodiments, the composition or formulation comprises 1-100 mM Tris buffer. In some embodiments, the composition or formulation comprises 1-50 mM Tris buffer. In some embodiments, the composition or formulation comprises 1-10 mM Tris buffer. In some embodiments, the disclosure provides a method for manufacturing a pharmaceutical composition comprising lyophilized bacteria. In some embodiments, the percent water content of the lyophilized bacteria is approximately 1-10%. In some embodiments, the percent water content is approximately 3-8%. In some embodiments, the percent water content is approximately 3-6%. In some embodiments, the percent water content is approximately 3-5%. In some embodiments, the percent water content is approximately 3%, approximately 4%, or approximately 5%.

Lyophilization

In some embodiments, the disclosure provides methods for manufacturing lyophilized engineered microorganisms, e.g., lyophilized genetically engineered bacteria. In some embodiments, methods for manufacturing engineered lyophilized microorganisms, e.g., lyophilized bacteria, result in percent viability and potency that is at least about equal to a frozen composition of the bacteria.

In some embodiments, the lyophilization process comprises suspending the cells in lyophilization buffer. In some embodiments, the lyophilization process comprises freezing the material at a temperature of −80° C. to −30° C., with primary drying at −25° C. to −5° C., and secondary drying at 5° C. to 25° C. In some embodiments, the lyophilization process comprises primary drying at −15° C. In some embodiments, the lyophilization process comprises secondary drying at 5° C. In some embodiments, after completion of the lyophilization cycle, the lyophilized cake is sieved through a 80-mesh screen into a free flowing powder.

Spray Drying

In some embodiments, the spray drying process comprises suspending the cells in spray drying buffer. In some embodiments, the spray drying process comprises spray drying the cells through a 2-fluid nozzle with an inlet temperature of 110 to 150° C., targeting an outlet temperature of 40-80° C., resulting in a free flowing powder. In some embodiments, the inlet temperature is 120-135° C. In some embodiments, the targeted outlet temperature is 60° C.

Frozen Liquid

In some embodiments, the frozen liquid process comprises suspending cells in cryoprotectant buffer, and freezing at −20° C. to 200° C. In some embodiments, the cell suspension is frozen at −80° C.

Genetically Engineered Bacteria

The disclosure provides methods to determine the live cell count of engineered microorganisms, e.g., genetically engineered bacteria, and compositions, formulations, dosing, methods of manufacturing engineered microorganisms, e.g., genetically engineered bacteria, using, e.g., the live cell counting method. Engineered microorganisms, e.g., genetically engineered bacteria, and compositions and formulations thereof that may be assayed, e.g., using the live cell counting method, are described in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety.

In some embodiments, the engineered microorganisms, e.g., genetically engineered bacteria, comprise one or more gene(s) for producing a desired therapeutic molecule. In some embodiments, the one or more gene(s) is operably linked to an inducible promoter. In some embodiments, the therapeutic molecule is capable of producing a therapeutic effect in a subject. For example, a therapeutic molecule such as IL-10 may be capable of reducing inflammation in a subject. In some embodiments, the therapeutic molecule is an anti-cancer molecule. In some embodiments, the therapeutic molecule is an enzyme capable of producing a STING agonist. In some embodiments, the therapeutic molecule is a deadenylate cyclase, e.g., dacA. In some embodiments, the therapeutic molecule is capable of reducing one or more deleterious molecules in the subject, e.g., a phenylalanine-metabolizing enzyme is capable of metabolizing excess and deleterious phenylalanine in a subject with PKU. In some embodiments, the engineered microorganisms, e.g., genetically engineered bacteria, comprise gene(s) encoding a modified arginine biosynthesis pathway (e.g., deleted arginine repressor, modified arginine repressor binding sites, and/or arginine feedback resistant N-acetylglutamate synthase mutation) and is capable of reducing deleterious ammonia, e.g., in a subject with UCD or in a subject with cancer. In some embodiments, the therapeutic molecule works in conjunction with another molecule to produce a therapeutic effect, e.g., a phenylalanine transporter works in conjunction with a phenylalanine-metabolizing enzyme to reduce deleterious phenylalanine in a subject with PKU. In some embodiments, the engineered microorganisms, e.g., genetically engineered bacteria, disclosed herein expresses one or more therapeutic molecule(s). In some embodiments, the engineered microorganisms, e.g., genetically engineered bacteria, disclosed herein expresses one or more therapeutic molecule(s) prior to administration to a subject. In some embodiments, the engineered microorganisms, e.g., genetically engineered bacteria, disclosed herein expresses one or more therapeutic molecule(s) after administration to a subject, e.g., the gene(s) for producing the therapeutic molecule are induced after administration to the subject.

In some embodiments disclosed herein are compositions comprising a predetermined number of engineered microorganisms, e.g., genetically engineered bacteria. In some embodiments, the composition comprises at least approximately $10^4$ live cells. In some embodiments, the composition comprises at least approximately $10^5$ live cells. In some embodiments, the composition comprises at least approximately $10^6$ live cells. In some embodiments, the composition comprises at least approximately $10^7$ live cells. In some embodiments, the composition comprises at least approximately $10^8$ live cells. In some embodiments, suitable dosage amounts for the engineered microorganisms, e.g., genetically engineered bacteria, may range from about $10^4$ to $10^{12}$ live bacteria, e.g., approximately $10^4$ live bacteria, approximately $10^5$ live bacteria, approximately $10^6$ live bacteria, approximately $10^7$ live bacteria, approximately $10^8$ live bacteria, approximately $10^9$ live bacteria, approximately $10^{10}$ live bacteria, approximately $10^{11}$ live bacteria, or approximately $10^{12}$ live bacteria. In some embodiments, the composition comprises approximately $10^8$ to $10^{13}$ live cells. In some embodiments, the composition comprises approximately $10^9$ to $10^{13}$ live cells. In some embodiments, the composition comprises approximately $10^{10}$ to $10^{12}$ live cells.

In some embodiments, the composition comprises approximately $1\times10^{11}$ live cells, approximately $1.1\times10^{11}$ live cells, approximately $1.2\times10^{11}$ live cells, approximately $1.3\times10^{11}$ live cells, approximately $1.4\times10^{11}$ live cells, approximately $1.5\times10^{11}$ live cells, approximately $1.6\times10^{11}$ live cells, approximately $1.7\times10^{11}$ live cells, approximately $1.8\times10^{11}$ live cells, approximately $1.9\times10^{11}$ live cells, approximately $2\times10^{11}$ live cells, approximately $2.1\times10^{11}$ live cells, approximately $2.2\times10^{11}$ live cells, approximately $2.3\times10^{11}$ live cells, approximately $2.4\times10^{11}$ live cells, approximately $2.5\times10^{11}$ live cells, approximately $2.6\times10^{11}$ live cells, approximately $2.7\times10^{11}$ live cells, approximately $2.8\times10^{11}$ live cells, approximately $2.9\times10^{11}$ live cells, approximately $3\times10^{11}$ live cells, approximately $3.1\times10^{11}$ live cells, approximately $3.2\times10^{11}$ live cells, approximately $3.3\times10^{11}$ live cells, approximately $3.4\times10^{11}$ live cells, approximately $3.5\times10^{11}$ live cells, approximately $3.6\times10^{11}$ live cells, approximately $3.7\times10^{11}$ live cells, approximately $3.8\times10^{11}$ live cells, approximately $3.9\times10^{11}$ live cells, or approximately $4\times10^{11}$ live cells. In some embodiments, the composition comprises approximately $5\times10^{11}$ live cells, approximately $6\times10^{11}$ live cells, approximately $7\times10^{11}$ live cells, approximately $8\times10^{11}$ live cells, or approximately $9\times10^{11}$ live cells.

In some embodiments, the composition comprises approximately $1\times10^{12}$ live cells, approximately $1.1\times10^{12}$ live cells, approximately $1.2\times10^{12}$ live cells, approximately $1.3\times10^{12}$ live cells, approximately $1.4\times10^{12}$ live cells, approximately $1.5\times10^{12}$ live cells, approximately $1.6\times10^{12}$ live cells, approximately $1.7\times10^{12}$ live cells, approximately $1.8\times10^{12}$ live cells, approximately $1.9\times10^{12}$ live cells, approximately $2\times10^{12}$ live cells, approximately $2.1\times10^{12}$ live cells, approximately $2.2\times10^{12}$ live cells, approximately $2.3\times10^{12}$ live cells, approximately $2.4\times10^{12}$ live cells, approximately $2.5\times10^{12}$ live cells, approximately $2.6\times10^{12}$ live cells, approximately $2.7\times10^{12}$ live cells, approximately $2.8\times10^{12}$ live cells, approximately $2.9\times10^{12}$ live cells, approximately $3\times10^{12}$ live cells, approximately $3.1\times10^{12}$ live cells, approximately $3.2\times10^{12}$ live cells, approximately $3.3\times10^{12}$ live cells, approximately $3.4\times10^{12}$ live cells, approximately $3.5\times10^{12}$ live cells, approximately $3.6\times10^{12}$ live cells, approximately $3.7\times10^{12}$ live cells, approximately $3.8\times10^{12}$ live cells, approximately $3.9\times10^{12}$ live cells, approximately $4\times10^{12}$ live cells, approximately $4.1\times10^{12}$ live cells, approximately $4.2\times10^{12}$ live cells, approximately $4.3\times10^{12}$ live cells, approximately $4.4\times10^{12}$ live cells, approximately $4.5\times10^{12}$ live cells, approximately $4.6\times10^{12}$ live cells, approximately $4.7\times10^{12}$ live cells, approximately $4.8\times10^{12}$ live cells, approximately $4.9\times10^{12}$ live cells, or approximately $5\times10^{12}$ live cells.

In some embodiments, the composition comprises $1\times10^{12}$ live cells, $2\times10^{12}$ live cells, $3\times10^{12}$ live cells, $4\times10^{12}$ live cells, or $5\times10^{12}$ live cells. In some embodiments, the composition comprises $2\times10^{12}$ live cells. In further embodiments, the composition comprises $2\times10^{12}$ live cells ($5.3\times10^{10}$ CFUs).

In some embodiments, the composition comprises approximately $1\times10^{11}$ live cells, approximately $1.1\times10^{11}$ live cells, approximately $1.2\times10^{11}$ live cells, approximately $1.3\times10^{11}$ live cells, approximately $1.4\times10^{11}$ live cells, approximately $1.5\times10^{11}$ live cells, approximately $1.6\times10^{11}$ live cells, approximately $1.7\times10^{11}$ live cells, approximately $1.8\times10^{11}$ live cells, approximately $1.9\times10^{11}$ live cells, approximately $2\times10^{11}$ live cells, approximately $2.1\times10^{11}$ live cells, approximately $2.2\times10^{11}$ live cells, approximately $2.3\times10^{11}$ live cells, approximately $2.4\times10^{11}$ live cells, approximately $2.5\times10^{11}$ live cells, approximately $2.6\times10^{11}$ live cells, approximately $2.7\times10^{11}$ live cells, approximately $2.8\times10^{11}$ live cells, approximately $2.9\times10^{11}$ live cells, approximately $3\times10^{11}$ live cells, approximately $3.1\times10^{11}$ live cells, approximately $3.2\times10^{11}$ live cells, approximately $3.3\times10^{11}$ live cells, approximately $3.4\times10^{11}$ live cells, approximately $3.5\times10^{11}$ live cells, approximately $3.6\times10^{11}$ live cells, approximately $3.7\times10^{11}$ live cells, approximately $3.8\times10^{11}$ live cells, approximately $3.9\times10^{11}$ live cells, or approximately $4\times10^{11}$ live cells of genetically engineered microorganisms, e.g., genetically engineered bacteria that express a dacA, or a modified arginine biosynthesis pathway, or a phenylalanine metabolizing enzyme, e.g., PAL and/or LAAD, optionally wherein the activity of the composition is determined by transcinnamic acid (TCA), hippurate (HA or labeled D5-HA), PPA, blood phenylalanine, ammonia, arginine, citrulline, cyclic dinucleotide, cyclic di-AMP, or other suitable measurement, e.g., relative to control.

In some embodiments, the composition comprises approximately $5\times10^{11}$ live cells, approximately $6\times10^{11}$ live cells, approximately $7\times10^{11}$ live cells, approximately $8\times10^{11}$ live cells, or approximately $9\times10^{11}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the composition is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the composition comprises approximately $1\times10^{12}$ live cells, approximately $1.1\times10^{12}$ live cells, approximately $1.2\times10^{12}$ live cells, approximately $1.3\times10^{12}$ live cells, approximately $1.4\times10^{12}$ live cells, approximately $1.5\times10^{12}$ live cells, approximately $1.6\times10^{12}$ live cells, approximately $1.7\times10^{12}$ live cells, approximately $1.8\times10^{12}$ live cells, approximately $1.9\times10^{12}$ live cells, approximately $2\times10^{12}$ live cells, approximately $2.1\times10^{12}$ live cells, approximately $2.2\times10^{12}$ live cells, approximately $2.3\times10^{12}$ live cells, approximately $2.4\times10^{12}$ live cells, approximately $2.5\times10^{12}$ live cells, approximately $2.6\times10^{12}$ live cells, approximately $2.7\times10^{12}$ live cells, approximately $2.8\times10^{12}$ live cells, approximately $2.9\times10^{12}$ live cells, approximately $3\times10^{12}$ live cells, approximately $3.1\times10^{12}$ live cells, approximately $3.2\times10^{12}$ live cells, approximately $3.3\times10^{12}$ live cells, approximately $3.4\times10^{12}$ live cells, approximately $3.5\times10^{12}$ live cells, approximately $3.6\times10^{12}$ live cells, approximately $3.7\times10^{12}$ live cells, approximately $3.8\times10^{12}$ live cells, approximately $3.9\times10^{12}$ live cells, approximately $4\times10^{12}$ live cells, approximately $4.1\times10^{12}$ live cells, approximately $4.2\times10^{12}$ live cells, approximately $4.3\times10^{12}$ live cells, approximately $4.4\times10^{12}$ live cells, approximately $4.5\times10^{12}$ live cells, approximately $4.6\times10^{12}$ live cells, approximately $4.7\times10^{12}$ live cells, approximately $4.8\times10^{12}$ live cells, approximately $4.9\times10^{12}$ live cells, or approximately $5\times10^{12}$ live cells of genetically engineered microorganisms, e.g., genetically engineered bacteria, that express dacA, or a modified arginine biosynthesis pathway, or a phenylalanine metabolizing enzyme, e.g., PAL and/or LAAD, optionally wherein the activity of the composition is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the composition comprises $1\times10^{12}$ live cells, $2\times10^{12}$ live cells, $3\times10^{12}$ live cells, $4\times10^{12}$ live cells, or $5\times10^{12}$ live cells of genetically engineered microorganisms, e.g., genetically engineered bacteria, that express phenylalanine metabolizing enzyme, e.g., PAL and/or LAAD, optionally wherein the activity of the composition is determined by TCA, HA or labeled D5-HA, PPA, blood phenylalanine, or other suitable measurement, e.g., relative to control. In some embodiments, the composition comprises $2\times10^{12}$ live cells of genetically engineered microorganisms, e.g., genetically engineered bacteria, that express phenylalanine metabolizing enzyme, e.g., PAL and/or LAAD, optionally wherein the activity of the composition is determined by TCA, HA or labeled D5-HA, PPA, blood phenylalanine, or other suitable measurement, e.g., relative to control. In further embodiments, the composition comprises $2\times10^{12}$ live cells ($5.3\times10^{10}$ CFUs) of genetically engineered microorganisms, e.g., genetically engineered bacteria, that express dacA, or a modified arginine biosynthesis pathway, or a phenylalanine metabolizing enzyme, e.g., PAL and/or LAAD, optionally wherein the activity of the composition is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the engineered microorganisms, e.g., genetically engineered bacteria, are non-pathogenic bacteria. In some embodiments, the engineered microorganisms, e.g., genetically engineered bacteria, are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to, *Bacteroides, Bifidobacterium, Clostridium, Escherichia, Lactobacillus*, and *Lactococcus*. In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added).

Unmodified *E. coli* Nissle or genetically engineered bacteria may be destroyed, e.g., by defense factors in the gut or blood serum (Sonnenborn et al., 2009) or by activation of a kill switch, several hours or days after administration. Thus, the composition may require continued administration. In some embodiments, the residence time is calculated for a human subject.

In some embodiments, the therapeutic molecule, e.g., PAL, may be expressed on a low-copy plasmid, a high-copy plasmid, or on the chromosome, e.g., at one or more of the following insertion sites in *E. coli* Nissle: malE/K, insB/I, araC/BAD, lacZ, agaI/rsmI, thyA, and malP/T. The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. In some embodiments, more than one copy, e.g., two, three, four, five, six, seven, eight, nine, ten or more copies of the therapeutic molecule, e.g., PAL, is integrated into the bacterial chromosome at one or more integration sites in the engineered microorganisms, e.g., genetically engineered bacteria.

In some embodiments, the engineered microorganisms, e.g., genetically engineered bacteria, comprise one or more gene(s) encoding a phenylalanine metabolizing enzyme (PME); one or more gene(s) for producing an anti-cancer molecule, e.g., a deadenylate cyclase gene (e.g., dacA) or an enzyme capable of producing a STING agonist; and one or more gene(s) encoding a modified arginine biosynthesis pathway, e.g., deleted arginine repressor, modified arginine repressor binding sites, and/or arginine feedback resistant N-acetylglutamate synthase mutation, for producing arginine. In some embodiments, the engineered microorganisms, e.g., genetically engineered bacteria, comprise a gene encoding PME, wherein the PME gene is operably linked to an inducible promoter. In some embodiments, the microorganisms, e.g., bacteria, comprise a non-native PME gene. In some embodiments, the microorganisms, e.g., bacteria, comprise additional copies of a native PME gene. In some embodiments, the promoter is not associated with the PME gene in nature.

In some embodiments, the engineered microorganisms, e.g., genetically engineered bacteria, comprise a gene encoding PAL. In some embodiments, the engineered microorganisms, e.g., genetically engineered bacteria, comprise a gene encoding PAL, wherein the PAL gene is operably linked to an inducible promoter. In some embodiments, the microorganisms, e.g., bacteria, comprise a non-native PAL gene. In some embodiments, the microorganisms, e.g., bacteria, comprise additional copies of a native PAL gene. In some embodiments, the promoter is not associated with the PAL gene in nature. In some embodiments, the promoter is any one or more of the promoters disclosed herein.

In some embodiments, the engineered microorganisms, e.g., genetically engineered bacteria, comprise a gene encoding LAAD. In some embodiments, the LAAD gene is operably linked to an inducible promoter. In some embodiments, the microorganisms, e.g., bacteria, comprise a non-native LAAD gene. In some embodiments, the microorganisms, e.g., bacteria, comprise additional copies of a native LAAD gene. In some embodiments, the promoter is not associated with the LAAD gene in nature.

In some embodiments, the engineered microorganisms, e.g., genetically engineered bacteria, further comprise a gene encoding a phenylalanine transporter, e.g., PheP. In some embodiments, the engineered microorganisms, e.g., genetically engineered bacteria, comprise a gene encoding a non-native phenylalanine transporter, e.g., additional copies of a native phenylalanine transporter. In some embodiments, the phenylalanine transporter gene is operably linked to an inducible promoter. In some embodiments, the promoter is not associated with the PheP gene in nature.

In some embodiments, the engineered microorganisms, e.g., genetically engineered bacteria, are auxotrophs for one or more essential genes. For example, a mutation of, modification of, or excision of an essential gene may result in the engineered microorganisms, e.g., genetically engineered bacteria, becoming an auxotroph. An auxotrophic modification is intended to cause bacteria to die in the absence of an exogenously added nutrient essential for survival or growth because they lack the gene(s) necessary to produce that essential nutrient. In some embodiments, any of the engineered microorganisms, e.g., genetically engineered bacteria, described herein also comprise a deletion or mutation in a gene required for cell survival and/or growth.

Exemplary auxotrophs are provided in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety. In one embodiment, the essential gene is a DNA synthesis gene, for example, thyA. Thymine is a nucleic acid that is required for bacterial cell growth; in its absence, bacteria undergo cell death. The thyA gene encodes thymidylate synthetase, an enzyme that catalyzes the first step in thymine synthesis by converting dUMP to dTMP (Sat et al., 2003). In some embodiments, the microorganism, e.g., bacterial cell, is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the microorganism, e.g., bacterial cell, is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

In another embodiment, the engineered microorganisms, e.g., genetically engineered bacteria, are auxotrophs in a cell wall synthesis gene, for example, dapA. Diaminopimelic acid (DAP) is an amino acid synthetized within the lysine biosynthetic pathway and is required for bacterial cell wall growth (Meadow et al., 1959; Clarkson et al., 1971). In some embodiments, any of the engineered microorganisms, e.g., genetically engineered bacteria, described herein is a dapD auxotroph in which dapD is deleted and/or replaced with an unrelated gene. A dapD auxotroph can grow only when sufficient amounts of DAP are present, e.g., by adding DAP to growth media in vitro, or in the presence of high DAP levels found naturally in the human gut in vivo. Without sufficient amounts of DAP, the dapD auxotroph dies. In some embodiments, the auxotrophic modification is used to ensure that the microorganism, e.g., bacterial cell, does not survive in the absence of the auxotrophic gene product (e.g., outside of the gut).

In some embodiments, a single promoter controls expression of the one or more gene(s) encoding the PME and the phenylalanine transporter. In some embodiments, separate copies of the same promoter controls expression of the expression of the PME and the phenylalanine transporter. In some embodiments, different promoters control expression of the PME and the phenylalanine transporter. In some embodiments, the promoter that controls expression of PME is different from the promoter(s) that controls expression of the phenylalanine transporter. In some embodiments, the promoter(s) operably linked to the gene(s) encoding the PME and the gene(s) encoding the phenylalanine transporter are induced by exogenous environmental conditions found in a mammalian gut. In some embodiments, the promoter(s) operably linked to the gene(s) encoding the PME and the gene(s) encoding the phenylalanine transporter are induced under low-oxygen or anaerobic conditions, e.g., an FNR-responsive promoter, an ANR-responsive promoter, and a DNR-responsive promoter. In some embodiments, the promoter(s) operably linked to the gene(s) encoding the PME and the gene(s) encoding the phenylalanine transporter is a thermoregulated promoter. In some embodiments, the promoter(s) operably linked to the gene(s) encoding the PME and the gene(s) encoding the phenylalanine transporter are induced by arabinose, IPTG, tetracycline, or rhamnose. In some embodiments, the gene(s) encoding the PME, e.g., PAL and/or LAAD, is operably linked to a promoter selected from a promoter that is induced under low-oxygen or anaerobic conditions, a thermoregulated promoter, and a promoter that is induced by arabinose, IPTG, tetracycline, or rhamnose. In some embodiments, the thermoregulated promoter is capable of being induced at a temperature between 37° C. and 42° C. In some embodiments, the thermoregulated promoter is a lambda CI inducible promoter. In some embodiments, the genetically engineered bacteria further comprise one or more gene(s) encoding a temperature sensitive CI repressor mutant, which, in some embodiments, is CI857.

Pharmaceutical Compositions

In some embodiments, the disclosure provides pharmaceutical compositions, which may be used to treat, manage, ameliorate, and/or prevent a diseases or disorder, e.g., a cancer; or a disease associated with hyperphenylalaninemia, e.g., PKU; or a disease associated with hyperammonemia, e.g., UCD or cancer. Pharmaceutical compositions of the invention comprising one or more engineered microorganisms, e.g., genetically engineered bacteria, alone or in combination with prophylactic agents, therapeutic agents, and/or and pharmaceutically acceptable carriers are provided. In certain embodiments, the pharmaceutical composition comprises one species, strain, or subtype of microorganism, e.g., bacteria, that are engineered to comprise the genetic modifications described herein. In alternate embodiments, the pharmaceutical composition comprises two or more species, strains, and/or subtypes of microorganisms, e.g., bacteria, that are each engineered to comprise the genetic modifications described herein.

In some embodiments, pharmaceutical compositions comprise a predetermined number of microorganisms, e.g., bacteria, as measured using the methods for characterizing, dosing, and determining the activity disclosed herein, e.g., live cell counting method. In some embodiments, the pharmaceutical composition comprises at least approximately $10^4$ live cells. In some embodiments, the pharmaceutical composition comprises at least approximately $10^5$ live cells. In some embodiments, the pharmaceutical composition comprises at least approximately $10^6$ live cells. In some embodiments, the pharmaceutical composition comprises at least approximately $10^7$ live cells. In some embodiments, the pharmaceutical composition comprises at least approximately $10^8$ live cells. In some embodiments, suitable dosage amounts for the genetically engineered bacteria may range from about $10^4$ to $10^{12}$ live bacteria, e.g., approximately $10^4$ live bacteria, approximately $10^5$ live bacteria, approximately $10^6$ live bacteria, approximately $10^7$ live bacteria, approximately $10^8$ live bacteria, approximately $10^9$ live bacteria, approximately $10^{10}$ live bacteria, approximately $10^{11}$ live bacteria, or approximately $10^{12}$ live bacteria. In some embodiments, the pharmaceutical composition comprises approximately $10^8$ to $10^{13}$ live cells. In some embodiments, the pharmaceutical composition comprises approximately $10^9$ to $10^{13}$ live cells. In some embodiments, the pharmaceutical composition comprises approximately $10^{10}$ to $10^{12}$ live cells.

In some embodiments, the pharmaceutical composition comprises approximately $1\times10^{11}$ live cells, approximately $1.1\times10^{11}$ live cells, approximately $1.2\times10^{11}$ live cells, approximately $1.3\times10^{11}$ live cells, approximately $1.4\times10^{11}$ live cells, approximately $1.5\times10^{11}$ live cells, approximately $1.6\times10^{11}$ live cells, approximately $1.7\times10^{11}$ live cells, approximately $1.8\times10^{11}$ live cells, approximately $1.9\times10^{11}$ live cells, approximately $2\times10^{11}$ live cells, approximately $2.1\times10^{11}$ live cells, approximately $2.2\times10^{11}$ live cells, approximately $2.3\times10^{11}$ live cells, approximately $2.4\times10^{11}$ live cells, approximately $2.5\times10^{11}$ live cells, approximately $2.6\times10^{11}$ live cells, approximately $2.7\times10^{11}$ live cells, approximately $2.8\times10^{11}$ live cells, approximately $2.9\times10^{11}$ live cells, approximately $3\times10^{11}$ live cells, approximately $3.1\times10^{11}$ live cells, approximately $3.2\times10^{11}$ live cells, approximately $3.3\times10^{11}$ live cells, approximately $3.4\times10^{11}$ live cells, approximately $3.5\times10^{11}$ live cells, approximately $3.6\times10^{11}$ live cells, approximately $3.7\times10^{11}$ live cells, approximately $3.8\times10^{11}$ live cells, approximately $3.9\times10^{11}$ live cells, or approximately $4\times10^{11}$ live cells. In some embodiments, the pharmaceutical composition comprises approximately $5\times10^{11}$ live cells, approximately $6\times10^{11}$ live cells, approximately $7\times10^{11}$ live cells, approximately $8\times10^{11}$ live cells, or approximately $9\times10^{11}$ live cells.

In some embodiments, the pharmaceutical composition comprises approximately $1\times10^{12}$ live cells, approximately $1.1\times10^{12}$ live cells, approximately $1.2\times10^{12}$ live cells, approximately $1.3\times10^{12}$ live cells, approximately $1.4\times10^{12}$ live cells, approximately $1.5\times10^{12}$ live cells, approximately $1.6\times10^{12}$ live cells, approximately $1.7\times10^{12}$ live cells, approximately $1.8\times10^{12}$ live cells, approximately $1.9\times10^{12}$ live cells, approximately $2\times10^{12}$ live cells, approximately $2.1\times10^{12}$ live cells, approximately $2.2\times10^{12}$ live cells, approximately $2.3\times10^{12}$ live cells, approximately $2.4\times10^{12}$ live cells, approximately $2.5\times10^{12}$ live cells, approximately $2.6\times10^{12}$ live cells, approximately $2.7\times10^{12}$ live cells, approximately $2.8\times10^{12}$ live cells, approximately $2.9\times10^{12}$ live cells, approximately $3\times10^{12}$ live cells, approximately $3.1\times10^{12}$ live cells, approximately $3.2\times10^{12}$ live cells, approximately $3.3\times10^{12}$ live cells, approximately $3.4\times10^{12}$ live cells, approximately $3.5\times10^{12}$ live cells, approximately $3.6\times10^{12}$ live cells, approximately $3.7\times10^{12}$ live cells, approximately $3.8\times10^{12}$ live cells, approximately $3.9\times10^{12}$ live cells, approximately $4\times10^{12}$ live cells, approximately $4.1\times10^{12}$ live cells, approximately $4.2\times10^{12}$ live cells, approximately $4.3\times10^{12}$ live cells, approximately $4.4\times10^{12}$ live cells, approximately $4.5\times10^{12}$ live cells, approximately $4.6\times10^{12}$ live cells, approximately $4.7\times10^{12}$ live cells, approximately $4.8\times10^{12}$ live cells, approximately $4.9\times10^{12}$ live cells, or approximately $5\times10^{12}$ live cells.

In some embodiments, the pharmaceutical composition comprises $1\times10^{12}$ live cells, $2\times10^{12}$ live cells, $3\times10^{12}$ live cells, $4\times10^{12}$ live cells, or $5\times10^{12}$ live cells. In some embodiments, the pharmaceutical composition comprises $2\times10^{12}$ live cells. In further embodiments, the pharmaceutical composition comprises $2\times10^{12}$ live cells ($5.3\times10^{10}$ CFUs). In some embodiments, the pharmaceutical composition is a liquid formulation. In some embodiments, the pharmaceutical composition is a solid formulation, e.g., a solid oral formulation.

In some embodiments, the disclosure provides pharmaceutical compositions with a live cell count concentration of $1\times10^6$-$1\times10^{15}$ live cells/mL, or for the case of dried, or lyophilized cells a cell count concentration after reconstitution of $1\times10^6$-$1\times10^{15}$ live cells/mL. In some embodiments, the disclosure provides pharmaceutical compositions with a live cell count concentration, or reconstituted live cell count concentration, of $1\times10^8$-$1\times10^{13}$ live cells/mL. In some embodiments, the disclosure provides pharmaceutical compositions with a live cell count concentration, or reconstituted live cell count concentration, of $1\times10^8$-$1\times10^{12}$ live cells/mL. In some embodiments, the disclosure provides pharmaceutical compositions with a live cell count concentration, or reconstituted live cell count concentration, of $1\times10^9$-$1\times10^{11}$ live cells/mL. In some embodiments, the disclosure provides pharmaceutical compositions with a live cell count concentration, or reconstituted live cell count concentration, of $1\times10^{10}$-$1\times10^{12}$ live cells/mL.

In some embodiments, the pharmaceutical composition is a solid formulation, e.g., solid oral formulation, comprising approximately $1\times10^{11}$ live cells, approximately $1.1\times10^{11}$ live cells, approximately $1.2\times10^{11}$ live cells, approximately $1.3\times10^{11}$ live cells, approximately $1.4\times10^{11}$ live cells, approximately $1.5\times10^{11}$ live cells, approximately $1.6\times10^{11}$ live cells, approximately $1.7\times10^{11}$ live cells, approximately $1.8\times10^{11}$ live cells, approximately $1.9\times10^{11}$ live cells, approximately $2\times10^{11}$ live cells, approximately $2.1\times10^{11}$ live cells, approximately $2.2\times10^{11}$ live cells, approximately $2.3\times10^{11}$ live cells, approximately $2.4\times10^{11}$ live cells, approximately $2.5\times10^{11}$ live cells, approximately $2.6\times10^{11}$ live cells, approximately $2.7\times10^{11}$ live cells, approximately $2.8\times10^{11}$ live cells, approximately $2.9\times10^{11}$ live cells, approximately $3\times10^{11}$ live cells, approximately $3.1\times10^{11}$ live cells, approximately $3.2\times10^{11}$ live cells, approximately $3.3\times10^{11}$ live cells, approximately $3.4\times10^{11}$ live cells, approximately $3.5\times10^{11}$ live cells, approximately $3.6\times10^{11}$ live cells, approximately $3.7\times10^{11}$ live cells, approximately $3.8\times10^{11}$ live cells, approximately $3.9\times10^{11}$ live cells, or approximately $4\times10^{11}$ live cells. In some embodiments, the pharmaceutical composition is a solid formulation, e.g., solid oral formulation, comprising approximately $5\times10^{11}$ live cells, approximately $6\times10^{11}$ live cells, approximately $7\times10^{11}$ live cells, approximately $8\times10^{11}$ live cells, or approximately $9\times10^{11}$ live cells.

In some embodiments, the pharmaceutical composition is a solid formulation, e.g., solid oral formulation, comprising approximately $1\times10^{12}$ live cells, approximately $1.1\times10^{12}$ live cells, approximately $1.2\times10^{12}$ live cells, approximately $1.3\times10^{12}$ live cells, approximately $1.4\times10^{12}$ live cells, approximately $1.5\times10^{12}$ live cells, approximately $1.6\times10^{12}$ live cells, approximately $1.7\times10^{12}$ live cells, approximately $1.8\times10^{12}$ live cells, approximately $1.9\times10^{12}$ live cells, approximately $2\times10^{12}$ live cells, approximately $2.1\times10^{12}$ live cells, approximately $2.2\times10^{12}$ live cells, approximately $2.3\times10^{12}$ live cells, approximately $2.4\times10^{12}$ live cells, approximately $2.5\times10^{12}$ live cells, approximately $2.6\times10^{12}$ live cells, approximately $2.7\times10^{12}$ live cells, approximately $2.8\times10^{12}$ live cells, approximately $2.9\times10^{12}$ live cells, approximately $3\times10^{12}$ live cells, approximately $3.1\times10^{12}$ live cells, approximately $3.2\times10^{12}$ live cells, approximately $3.3\times10^{12}$ live cells, approximately $3.4\times10^{12}$ live cells, approximately $3.5\times10^{12}$ live cells, approximately $3.6\times10^{12}$ live cells, approximately $3.7\times10^{12}$ live cells, approximately $3.8\times10^{12}$ live cells, approximately $3.9\times10^{12}$ live cells, approximately $4\times10^{12}$ live cells, approximately $4.1\times10^{12}$ live cells, approximately $4.2\times10^{12}$ live cells, approximately $4.3\times10^{12}$ live cells, approximately $4.4\times10^{12}$ live cells, approximately $4.5\times10^{12}$ live cells, approximately $4.6\times10^{12}$ live cells, approximately $4.7\times10^{12}$ live cells, approximately $4.8\times10^{12}$ live cells, approximately $4.9\times10^{12}$ live cells, or approximately $5\times10^{12}$ live cells.

In some embodiments, the pharmaceutical composition is a solid formulation, e.g., solid oral formulation, comprising $1\times10^{12}$ live cells, $2\times10^{12}$ live cells, $3\times10^{12}$ live cells, $4\times10^{12}$ live cells, or $5\times10^{12}$ live cells. In some embodiments, the pharmaceutical composition is a solid formulation, e.g., solid oral formulation, comprising $2\times10^{12}$ live cells. In further embodiments, the pharmaceutical composition is a solid formulation, e.g., solid oral formulation, comprising $2\times10^{12}$ live cells ($5.3\times10^{10}$ CFUs).

In some embodiments, the solid formulation, e.g., solid oral formulation, comprises approximately $1\times10^{11}$ live cells, approximately $1.1\times10^{11}$ live cells, approximately $1.2\times10^{11}$ live cells, approximately $1.3\times10^{11}$ live cells, approximately $1.4\times10^{11}$ live cells, approximately $1.5\times10^{11}$ live cells, approximately $1.6\times10^{11}$ live cells, approximately $1.7\times10^{11}$ live cells, approximately $1.8\times10^{11}$ live cells, approximately $1.9\times10^{11}$ live cells, approximately $2\times10^{11}$ live cells, approximately $2.1\times10^{11}$ live cells, approximately $2.2\times10^{11}$ live cells, approximately $2.3\times10^{11}$ live cells, approximately $2.4\times10^{11}$ live cells, approximately $2.5\times10^{11}$ live cells, approximately $2.6\times10^{11}$ live cells, approximately $2.7\times10^{11}$ live cells, approximately $2.8\times10^{11}$ live cells, approximately $2.9\times10^{11}$ live cells, approximately $3\times10^{11}$ live cells, approximately $3.1\times10^{11}$ live cells, approximately $3.2\times10^{11}$ live cells, approximately $3.3\times10^{11}$ live cells, approximately $3.4\times10^{11}$ live cells, approximately $3.5\times10^{11}$ live cells, approximately $3.6\times10^{11}$ live cells, approximately $3.7\times10^{11}$ live cells, approximately $3.8\times10^{11}$ live cells, approximately $3.9\times10^{11}$ live cells, or approximately $4\times10^{11}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the solid formulation, e.g., solid oral formulation, is determined by transcinnamic acid (TCA), hippurate (HA or labeled D5-HA), blood phenylalanine, or other suitable measurement, e.g., relative to control.

In some embodiments, the solid formulation, e.g., solid oral formulation, comprises approximately $5\times10^{11}$ live cells, approximately $6\times10^{11}$ live cells, approximately $7\times10^{11}$ live cells, approximately $8\times10^{11}$ live cells, or approximately $9\times10^{11}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the solid formulation, e.g., solid oral formulation, is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the solid formulation, e.g., solid oral formulation, comprises approximately $1\times10^{12}$ live cells, approximately $1.1\times10^{12}$ live cells, approximately $1.2\times10^{12}$ live cells, approximately $1.3\times10^{12}$ live cells, approximately $1.4\times10^{12}$ live cells, approximately $1.5\times10^{12}$ live cells, approximately $1.6\times10^{12}$ live cells, approximately $1.7\times10^{12}$ live cells, approximately $1.8\times10^{12}$ live cells, approximately $1.9\times10^{12}$ live cells, approximately $2\times10^{12}$ live cells, approximately $2.1\times10^{12}$ live cells, approximately $2.2\times10^{12}$ live cells, approximately $2.3\times10^{12}$ live cells, approximately $2.4\times10^{12}$ live cells, approximately $2.5\times10^{12}$ live cells, approximately $2.6\times10^{12}$ live cells, approximately $2.7\times10^{12}$ live cells, approximately $2.8\times10^{12}$ live cells, approximately $2.9\times10^{12}$ live cells, approximately $3\times10^{12}$ live cells, approximately $3.1\times10^{12}$ live cells, approximately $3.2\times10^{12}$ live cells, approximately $3.3\times10^{12}$ live cells, approximately $3.4\times10^{12}$ live cells, approximately $3.5\times10^{12}$ live cells, approximately $3.6\times10^{12}$ live cells, approximately $3.7\times10^{12}$ live cells, approximately $3.8\times10^{12}$ live cells, approximately $3.9\times10^{12}$ live cells, approximately $4\times10^{12}$ live cells, approximately $4.1\times10^{12}$ live cells, approximately $4.2\times10^{12}$ live cells, approximately $4.3\times10^{12}$ live cells, approximately $4.4\times10^{12}$ live cells, approximately $4.5\times10^{12}$ live cells, approximately $4.6\times10^{12}$ live cells, approximately $4.7\times10^{12}$ live cells, approximately $4.8\times10^{12}$ live cells, approximately $4.9\times10^{12}$ live cells, or approximately $5\times10^{12}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the solid formulation, e.g., solid oral formulation, is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the solid formulation, e.g., solid oral formulation, comprises $1\times10^{12}$ live cells, $2\times10^{12}$ live cells, $3\times10^{12}$ live cells, $4\times10^{12}$ live cells, or $5\times10^{12}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the solid formulation, e.g., solid oral formulation, is determined by TCA, HA or labeled D5-HA, PPA, blood phenylalanine, ammonia, arginine, citrulline, cyclic dinucleotide, cyclic di-AMP, or other suitable measurement, e.g., relative to control. In some embodiments, the solid formulation, e.g., solid oral formulation, comprises $2\times10^{12}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the solid formulation, e.g., solid oral formulation, is determined by TCA, HA or labeled D5-HA, PPA, blood phenylalanine, ammonia, arginine, citrulline, cyclic dinucleotide, cyclic di-AMP, or other suitable measurement, e.g., relative to control. In further embodiments, the solid formulation, e.g., solid oral formulation, comprises $2\times10^{12}$ live cells ($5.3\times10^{10}$ CFUs) of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the solid formulation, e.g., solid oral formulation, is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the pharmaceutical composition is a liquid formulation comprising approximately $1\times10^{11}$ live cells, approximately $1.1\times10^{11}$ live cells, approximately $1.2\times10^{11}$ live cells, approximately $1.3\times10^{11}$ live cells, approximately $1.4\times10^{11}$ live cells, approximately $1.5\times10^{11}$ live cells, approximately $1.6\times10^{11}$ live cells, approximately $1.7\times10^{11}$ live cells, approximately $1.8\times10^{11}$ live cells, approximately $1.9\times10^{11}$ live cells, approximately $2\times10^{11}$ live cells, approximately $2.1\times10^{11}$ live cells, approximately $2.2\times10^{11}$ live cells, approximately $2.3\times10^{11}$ live cells, approximately $2.4\times10^{11}$ live cells, approximately $2.5\times10^{11}$ live cells, approximately $2.6\times10^{11}$ live cells, approximately $2.7\times10^{11}$ live cells, approximately $2.8\times10^{11}$ live cells, approximately $2.9\times10^{11}$ live cells, approximately $3\times10^{11}$ live cells, approximately $3.1\times10^{11}$ live cells, approximately $3.2\times10^{11}$ live cells, approximately $3.3\times10^{11}$ live cells, approximately $3.4\times10^{11}$ live cells, approximately $3.5\times10^{11}$ live cells, approximately $3.6\times10^{11}$ live cells, approximately $3.7\times10^{11}$ live cells, approximately $3.8\times10^{11}$ live cells, approximately $3.9\times10^{11}$ live cells, or approximately $4\times10^{11}$ live cells. In some embodiments, the pharmaceutical composition is a liquid formulation comprising approximately $5\times10^{11}$ live cells, approximately $6\times10^{11}$ live cells, approximately $7\times10^{11}$ live cells, approximately $8\times10^{11}$ live cells, or approximately $9\times10^{11}$ live cells.

In some embodiments, the pharmaceutical composition is a liquid formulation comprising approximately $1\times10^{12}$ live cells, approximately $1.1\times10^{12}$ live cells, approximately $1.2\times10^{12}$ live cells, approximately $1.3\times10^{12}$ live cells, approximately $1.4\times10^{12}$ live cells, approximately $1.5\times10^{12}$ live cells, approximately $1.6\times10^{12}$ live cells, approximately $1.7\times10^{12}$ live cells, approximately $1.8\times10^{12}$ live cells, approximately $1.9\times10^{12}$ live cells, approximately $2\times10^{12}$ live cells, approximately $2.1\times10^{12}$ live cells, approximately $2.2\times10^{12}$ live cells, approximately $2.3\times10^{12}$ live cells, approximately $2.4\times10^{12}$ live cells, approximately $2.5\times10^{12}$ live cells, approximately $2.6\times10^{12}$ live cells, approximately $2.7\times10^{12}$ live cells, approximately $2.8\times10^{12}$ live cells, approximately $2.9\times10^{12}$ live cells, approximately $3\times10^{12}$ live cells, approximately $3.1\times10^{12}$ live cells, approximately $3.2\times10^{12}$ live cells, approximately $3.3\times10^{12}$ live cells, approximately $3.4\times10^{12}$ live cells, approximately $3.5\times10^{12}$ live cells, approximately $3.6\times10^{12}$ live cells, approximately $3.7\times10^{12}$ live cells, approximately $3.8\times10^{12}$ live cells, approximately $3.9\times10^{12}$ live cells, approximately $4\times10^{12}$ live cells, approximately $4.1\times10^{12}$ live cells, approximately $4.2\times10^{12}$ live cells, approximately $4.3\times10^{12}$ live cells, approximately $4.4\times10^{12}$ live cells, approximately $4.5\times10^{12}$ live cells, approximately $4.6\times10^{12}$ live cells, approximately $4.7\times10^{12}$ live cells, approximately $4.8\times10^{12}$ live cells, approximately $4.9\times10^{12}$ live cells, or approximately $5\times10^{12}$ live cells.

In some embodiments, the pharmaceutical composition is a liquid formulation comprising $1\times10^{12}$ live cells, $2\times10^{12}$ live cells, $3\times10^{12}$ live cells, $4\times10^{12}$ live cells, or $5\times10^{12}$ live cells. In some embodiments, the pharmaceutical composition is a liquid formulation comprising $2\times10^{12}$ live cells. In further embodiments, the pharmaceutical composition is a liquid formulation comprising $2\times10^{12}$ live cells ($5.3\times10^{10}$ CFUs).

In some embodiments, the liquid formulation comprises approximately $1\times10^{11}$ live cells, approximately $1.1\times10^{11}$ live cells, approximately $1.2\times10^{11}$ live cells, approximately $1.3\times10^{11}$ live cells, approximately $1.4\times10^{11}$ live cells, approximately $1.5\times10^{11}$ live cells, approximately $1.6\times10^{11}$ live cells, approximately $1.7\times10^{11}$ live cells, approximately $1.8\times10^{11}$ live cells, approximately $1.9\times10^{11}$ live cells, approximately $2\times10^{11}$ live cells, approximately $2.1\times10^{11}$ live cells, approximately $2.2\times10^{11}$ live cells, approximately $2.3\times10^{11}$ live cells, approximately $2.4\times10^{11}$ live cells, approximately $2.5\times10^{11}$ live cells, approximately $2.6\times10^{11}$ live cells, approximately $2.7\times10^{11}$ live cells, approximately $2.8\times10^{11}$ live cells, approximately $2.9\times10^{11}$ live cells, approximately $3\times10^{11}$ live cells, approximately $3.1\times10^{11}$ live cells, approximately $3.2\times10^{11}$ live cells, approximately $3.3\times10^{11}$ live cells, approximately $3.4\times10^{11}$ live cells, approximately $3.5\times10^{11}$ live cells, approximately $3.6\times10^{11}$ live cells, approximately $3.7\times10^{11}$ live cells, approximately $3.8\times10^{11}$ live cells, approximately $3.9\times10^{11}$ live cells, or approximately $4\times10^{11}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the liquid formulation is determined by TCA, HA or labeled D5-HA, blood phenylalanine, ammonia, arginine, citrulline, cyclic dinucleotide, cyclic di-AMP, or other suitable measurement, e.g., relative to control.

In some embodiments, the liquid formulation comprises approximately $5\times10^{11}$ live cells, approximately $6\times10^{11}$ live cells, approximately $7\times10^{11}$ live cells, approximately $8\times10^{11}$ live cells, or approximately $9\times10^{11}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the liquid formulation is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the liquid formulation comprises approximately $1\times10^{12}$ live cells, approximately $1.1\times10^{12}$ live cells, approximately $1.2\times10^{12}$ live cells, approximately $1.3\times10^{12}$ live cells, approximately $1.4\times10^{12}$ live cells, approximately $1.5\times10^{12}$ live cells, approximately $1.6\times10^{12}$ live cells, approximately $1.7\times10^{12}$ live cells, approximately $1.8\times10^{12}$ live cells, approximately $1.9\times10^{12}$ live cells, approximately $2\times10^{12}$ live cells, approximately $2.1\times10^{12}$ live cells, approximately $2.2\times10^{12}$ live cells, approximately $2.3\times10^{12}$ live cells, approximately $2.4\times10^{12}$ live cells, approximately $2.5\times10^{12}$ live cells, approximately $2.6\times10^{12}$ live cells, approximately $2.7\times10^{12}$ live cells, approximately $2.8\times10^{12}$ live cells, approximately $2.9\times10^{12}$ live cells, approximately $3\times10^{12}$ live cells, approximately $3.1\times10^{12}$ live cells, approximately $3.2\times10^{12}$ live cells, approximately $3.3\times10^{12}$ live cells, approximately $3.4\times10^{12}$ live cells, approximately $3.5\times10^{12}$ live cells, approximately $3.6\times10^{12}$ live cells, approximately $3.7\times10^{12}$ live cells, approximately $3.8\times10^{12}$ live cells, approximately $3.9\times10^{12}$ live cells, approximately $4\times10^{12}$ live cells, approximately $4.1\times10^{12}$ live cells, approximately $4.2\times10^{12}$ live cells, approximately $4.3\times10^{12}$ live cells, approximately $4.4\times10^{12}$ live cells, approximately $4.5\times10^{12}$ live cells, approximately $4.6\times10^{12}$ live cells, approximately $4.7\times10^{12}$ live cells, approximately $4.8\times10^{12}$ live cells, approximately $4.9\times10^{12}$ live cells, or approximately $5\times10^{12}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the liquid formulation is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the liquid formulation comprises $1\times10^{12}$ live cells, $2\times10^{12}$ live cells, $3\times10^{12}$ live cells, $4\times10^{12}$ live cells, or $5\times10^{12}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the liquid formulation is determined by TCA, HA or labeled D5-HA, PPA, blood phenylalanine, ammonia, arginine, citrulline, cyclic dinucleotide, cyclic di-AMP, or other suitable measurement, e.g., relative to control. In some embodiments, the liquid formulation comprises $2\times10^{12}$ live cells of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the liquid formulation is determined by TCA, HA or labeled D5-HA, PPA, blood phenylalanine, ammonia, arginine, citrulline, cyclic dinucleotide, cyclic di-AMP, or other suitable measurement, e.g., relative to control. In further embodiments, the liquid formulation comprises $2\times10^{12}$ live cells ($5.3\times10^{10}$ CFUs) of genetically engineered microorganisms, e.g., genetically engineered bacteria, that express a dacA, or a modified arginine biosynthesis pathway, or a phenylalanine metabolizing enzyme, e.g., PAL and/or LAAD, optionally wherein the activity of the liquid formulation is determined by TCA, HA or labeled D5-HA, PPA, blood phenylalanine, ammonia, arginine, citrulline, cyclic dinucleotide, cyclic di-AMP, or other suitable measurement, e.g., relative to control.

In some embodiments, the number of cells present in a pharmaceutical composition is determined using a live cell counting method. In some embodiments, determining the live cell count of the composition provides a more accurate measurement of the activity of the pharmaceutical composition than CFU count. In some embodiments, live cell counting provides reduced CFU count in a pharmaceutical composition as compared to the CFU method. In some embodiments, live cell counting allows for reducing the CFU count in a pharmaceutical composition, e.g., lyophilized or frozen liquid pharmaceutical composition, as compared to the CFU method. In some embodiments, determining the number of cells present in a pharmaceutical composition by live cell counting improves tolerability of the pharmaceutical composition. For example, a pharmaceutical composition comprises lowered CFU count using the live cell counting method as compared to the CFU method, and corresponds with lowered levels of cell lysate, endotoxin, etc. In some embodiments, the pharmaceutical composition determined using live cell counting comprises at least about 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, live cells, e.g., the number of living cells divided by the total number of cells. In some embodiments, the pharmaceutical composition determined using live cell counting comprises at least about 50-60% live cells, e.g., the number of living cells divided by the total number of cells. In some embodiments, the pharmaceutical composition determined using live cell counting comprises at least about 60-70% live cells, e.g., the number of living cells divided by the total number of cells. In some embodiments, the pharmaceutical composition determined using live cell counting comprises at least about 70-80% live cells, e.g., the number of living cells divided by the total number of cells. In some embodiments, the pharmaceutical composition determined using live cell counting comprises at least about 80-90% live cells, e.g., the number of living cells divided by the total number of cells. In some embodiments, the pharmaceutical composition determined using live cell counting comprises at least about 90-10% live cells, e.g., the number of living cells divided by the total number of cells. In some embodiments, the pharmaceutical composition determined using live cell counting comprises at least about 60% live cells, e.g., the number of living cells divided by the total number of cells. In some embodiments, the pharmaceutical composition determined using live cell counting comprises at least about 70% live cells, e.g., the number of living cells divided by the total number of cells. In some embodiments, the pharmaceutical composition determined using live cell counting comprises at least about 80% live cells, e.g., the number of living cells divided by the total number of cells. In some embodiments, the CFU method results in a microorganism cell count, e.g., bacterial cell count, that is too high for conventional formulation and/or manufacturing, and the more accurate live cell counting method provides a bacterial cell count that both therapeutically effective and is suitable for conventional formulation and/or manufacturing.

In some embodiments, the pharmaceutical composition determined using live cell counting comprises no more than approximately $1.9\times10^{8}\pm1.8\times10^{8}$ EU/gram of endotoxin, no more than approximately $4.0\times10^{8}$ EU/gram of endotoxin, no more than approximately $3.0\times10^{8}$ EU/gram of endotoxin, no more than approximately $2.0\times10^{8}$ EU/gram of endotoxin, no more than approximately $1.0\times10^{8}$ EU/gram of endotoxin, or no more than approximately $5\times10^{7}$ EU/gram of endotoxin.

In some embodiments, the pharmaceutical composition determined using the methods for characterizing, dosing, and determining the activity disclosed herein, e.g., live cell counting method. In some embodiments (e.g., wherein the microorganism, e.g., bacterium, is genetically engineered to comprise a PME) activity may be measured by conversion of phenylalanine to TCA, e.g., in vitro or in vivo, e.g., urinary HA. In some embodiments (e.g., wherein the microorganism, e.g., bacterium, is genetically engineered to comprise a PME), activity may be measured by conversion of phenylalanine to PPA, e.g., in vitro or in vivo. In some embodiments (e.g., wherein the microorganism, e.g., bacterium, is genetically engineered to comprise a modified arginine biosynthesis pathway, e.g., deleted arginine repressor, modified arginine repressor binding sites, and/or arginine feedback resistant N-acetylglutamate synthase mutation), the activity may be measured by assaying the levels of ammonia, arginine or citrulline, e.g., in vitro or in vivo. In some embodiments (e.g., wherein the microorganism, e.g., bacterium, is genetically engineered to comprise an anticancer molecule, e.g., dacA), the activity may be measured by assaying the levels of cyclic dinucleotide, e.g. cyclic di-AMP, e.g., in vitro or in vivo.

In some embodiments, the pharmaceutical composition is capable of producing TCA at a rate of at least approximately 0.5 μmol/hour/$10^{9}$ cells. In some embodiments, the pharmaceutical composition is capable of producing TCA at a rate of at least approximately 1.0 μmol/hour/$10^{9}$ cells. In some embodiments, the pharmaceutical composition is capable of producing TCA at a rate of at least approximately $1.9\pm1.2$ μmol/hour/$10^{9}$ cells. In some embodiments, the pharmaceutical composition is capable of producing TCA at a rate of approximately 1.5-10.0 μmol/hour/$10^{9}$ cells. In some embodiments, the pharmaceutical composition is capable of producing TCA at a rate of approximately 1.5-5.0 μmol/hour/$10^{9}$ cells In some embodiments, the pharmaceutical composition is capable of producing PPA at a rate of at least approximately 1.0 μmol/hour/$10^9$ cells. In some embodiments, the pharmaceutical composition is capable of producing PPA at a rate of is at least approximately 1.5 μmol/hour/$10^9$ cells, at least approximately 2.9±0.7 μmol/hour/$10^9$ cells. In some embodiments, the pharmaceutical composition is capable of producing PPA at a rate of approximately 2.0-10.0 μmol/hour/$10^9$ cells. In some embodiments, the pharmaceutical composition is capable of producing PPA at a rate of approximately 2.0-5.0 μmol/hour/$10^9$ cells.

In some embodiments, live cell count is determined using a fluorescent dye that is capable of selectively identifying living or non-living cells. In some embodiments, the fluorescent dye selectively accumulates in living or non-living cells, thus allowing the identification of living or non-living cells. In some embodiments, the fluorescent dye becomes substantially more fluorescent only in living or non-living cells, thus allowing the identification of living or non-living cells. In some embodiments, non-living cells are distinguished from living cells using fluorescent dyes that are not permeable to the cell membrane. In some embodiments, living cells are distinguished from non-living cells using fluorescent dyes capable of selectively identifying cells with a proton gradient. In some embodiments, the live cell count of a composition can be determined by subtracting the number of non-living cells from the number of total cells. In some embodiments, the fluorescent dye is Sytox green stain.

In some embodiments, the live cell counting method provides reduced CFU count in a pharmaceutical composition as compared to the CFU method. In some embodiments, the live cell counting method allows for reducing the CFU count in a pharmaceutical composition, e.g., lyophilized or frozen liquid, as compared to the CFU method.

In some embodiments, the number of live cells to include in a pharmaceutical composition can be determined using activity of a composition comprising a predetermined number of dividing cells, for example, a composition comprising a predetermined number of CFUs. In some embodiments, the number of living cells to include in a pharmaceutical composition can be determined by 1) obtaining activity of the composition comprising the predetermined number of dividing cells, 2) determining the live cell count of the composition, 3) calculating the potency of the composition, e.g., in terms of activity/live cell, and 4) using the potency to determine the number of live cells for the composition. In some embodiments, the activity may reflect therapeutic effect, toxicity data, levels of therapeutic protein, and/or any other metric that is indicative of a pharmaceutical composition's efficacy and/or toxicity. An example of how the number of live cells to include in a pharmaceutical composition can be determined using a composition comprising a predetermined number of dividing cells is shown in Table 1 below.

TABLE 1

Determining the number of living cells administered to a subject

| Strain | CFU Dose | Volume of Cell Suspension (mL) | # Live Cells/ mL (Cellometer) | # Live Cells Dosed | # Total Cells/ mL (Cellometer) | # Total Cells Dosed |
|---|---|---|---|---|---|---|
| SYNB1618 | 1.00e+10 | 0.1 | 2.37e+11 | 2.37e+10 | 2.46e+11 | 2.46e+10 |
| | 5.00e+10 | 0.55 | | 1.31e+11 | | 1.35e+11 |
| | 7.00e+10 | 0.77 | | 1.83e+11 | | 1.89e+11 |
| | 1.00e+11 | 1.1 | | 2.61e+11 | | 2.70e+11 |
| | 5.00e+11 | 5.5 | | 1.31e+12 | | 1.35e+12 |

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The engineered microorganisms, e.g., genetically engineered bacteria, described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release).

The engineered microorganisms, e.g., genetically engineered bacteria, may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the engineered microorganisms, e.g., genetically engineered bacteria, of the invention may be formulated in a solution of sodium bicarbonate, e.g., 1 molar solution of sodium bicarbonate (to buffer an acidic cellular environment, such as the stomach, for example). In some embodiments, the engineered microorganism comprises a phenylalanine metabolizing enzyme such as phenylalanine ammonia lyase and is formulated in a solution of sodium bicarbonate or calcium bicarbonate optionally with PPI to buffer an acidic environment (e.g., less than a pH of 1, less than a pH of 2, less than a pH of 3, less than a pH of 4, less than a pH of 5, less than a pH of 6, or less than a pH of 7) and/or to reduce the acidity of the environment (e.g., resulting in a pH of greater than 5, a pH of greater than 6, a pH of greater than 7, a pH of greater than 8, a pH of greater than 9, or a pH of greater than 10), e.g., to modulate the acidity or acidic environment of the gut in a subject. In some embodiments, the engineered microorganism comprises a phenylalanine metabolizing enzyme such as phenylalanine ammonia lyase, is formulated in a solution of sodium bicarbonate or calcium bicarbonate, and further administered with (e.g., before, concurrently with, after) an antiemetict. Examples of antiemetics include but are not limited to promethazine, meclizine, hydroxyzine, droperidol, metoclopramide, ondansetron, dolasetron, maropitant, phenotyhiazines, famotidine, ranitidine, omeprazole, pantoprazole, misoprostol proton pump inhibitors, histamine-2 receptor antagonists, serotonin (5-HT3) antagonists, antihistamines, butyrophenones, or gastrokinetic agents. The engineered microorganisms, e.g., genetically engineered bacteria, may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The pharmaceutical compositions disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The pharmaceutical compositions disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the engineered microorganisms, e.g., genetically engineered bacteria, are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the engineered microorganisms, e.g., genetically engineered bacteria, described herein.

In one embodiment, the engineered microorganisms, e.g., genetically engineered bacteria, may be formulated in a composition suitable for administration to pediatric subjects. As is well known in the art, children differ from adults in many aspects, including different rates of gastric emptying, pH, gastrointestinal permeability, etc. (Ivanovska et al., 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the engineered microorganisms, e.g., genetically engineered bacteria, may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. See, e.g., US 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The pharmaceutical composition may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The engineered microorganisms, e.g., genetically engineered bacteria, may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, LD50, ED50, EC50, and IC50 may be determined, and the dose ratio between toxic and therapeutic effects (LD50/ED50) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally trehalose. Other suitable cryoprotectants include other disaccharides (e.g., sucrose or lactose), amino acids, and polymers.

In some embodiments, lyophilization may be performed in 1-20% trehalose, 1-10% trehalose, 5-15% trehalose, 7-13% trehalose, 9-11% trehalose, or about 10% trehalose in a biological buffer covering a pH range of 6-8, where the biological buffer may be PIPES, MOPS, HEPES, and/or Tris buffer. In some embodiments, the composition or formulation comprises 1-400 mM Tris buffer. In some embodiments, the composition or formulation comprises 1-300 mM Tris buffer. In some embodiments, the composition or formulation comprises 1-200 mM Tris buffer. In some embodiments, the composition or formulation comprises 1-100 mM Tris buffer. In some embodiments, the composition or formulation comprises 1-50 mM Tris buffer. In some embodiments, the composition or formulation comprises 1-10 mM Tris buffer. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

In some embodiments, the percent water content of the lyophilized cells is approximately 1-10%. In some embodiments, the percent water content is approximately 3-8%. In some embodiments, the percent water content is approximately 3-6%. In some embodiments, the percent water content is approximately 3-5%. In some embodiments, the percent water content is approximately 3%, approximately 4%, or approximately 5%.

In some embodiments, the disclosure provides pharmaceutical compositions that are stable when stored at 2-8° C. In some embodiments, the disclosure provides pharmaceutical compositions that are stable for at least approximately 3 months when stored at 2-8° C. In some embodiments, the disclosure provides pharmaceutical compositions that are stable for at least approximately 6 months when stored at 2-8° C. In some embodiments, the disclosure provides pharmaceutical compositions that are stable for at least approximately 9 months when stored at 2-8° C. In some embodiments, the disclosure provides pharmaceutical compositions that are stable for at least approximately 12 months when stored at 2-8° C. In some embodiments, the disclosure provides pharmaceutical compositions that are stable when stored at room temperature and 60% relative humidity. In some embodiments, the disclosure provides pharmaceutical compositions that are stable for at least 1 month when stored at room temperature and 60% relative humidity.

Methods of Treatment

In some embodiments, the disclosure provides methods for treating a subject suffering from a disease or disorder, where the methods comprise administering engineered microorganisms, e.g., genetically engineered bacteria, as measured, dosed, and/or manufactured using the methods for characterizing, dosing, and determining the activity disclosed herein, e.g., live cell counting method.

In some embodiments, the genetically engineered bacteria disclosed herein (e.g., comprising gene(s) for producing an anti-cancer molecule, e.g., a deadenylate cyclase gene or an enzyme capable of producing a stimulator of interferon gene agonist; or comprising gene(s) encoding a modified arginine biosynthesis pathway, e.g., deleted arginine repressor, modified arginine repressor binding sites, and/or arginine feedback resistant N-acetylglutamate synthase mutation; or comprising gene(s) for producing a phenylalanine metabolizing enzyme), compositions and formulations thereof, as assayed, dosed, and/or manufactured using the methods for characterizing, dosing, and determining the activity disclosed herein, e.g., live cell counting method, are used to treat a disease or disorder, e.g., a metabolic disease, a cancer, etc.

In some embodiments, the disclosure provides methods for reducing hyperphenylalaninemia or treating a disease associated with hyperphenylalaninemia by administering engineered microorganisms, e.g., genetically engineered bacteria, measured, dosed, and/or manufactured using the methods for characterizing, dosing, and determining the activity disclosed herein, e.g., live cell counting method. In some embodiments the methods for reducing hyperphenylalaninemia or treating a disease associated with hyperphenylalaninemia comprises administering any one of the pharmaceutical compositions disclosed herein. In some embodiments, the disease associated with hyperphenylalaninemia is selected from phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, Segawa's disease, and liver disease.

In some embodiments, the disclosure provides methods for treating inflammatory bowel disease (IBD), autoimmune disorders, diarrheal diseases, related diseases, and other diseases that benefit from reduced gut inflammation and/or enhanced gut barrier function by administering engineered microorganisms, e.g., genetically engineered bacteria, measured, dosed, and/or manufactured using the methods for characterizing, dosing, and determining the activity disclosed herein, e.g., live cell counting method. In some embodiments, the diarrheal disease is selected from the group consisting of acute watery diarrhea, e.g., cholera, acute bloody diarrhea, e.g., dysentery, and persistent diarrhea. In some embodiments, the IBD or related disease is selected from the group consisting of Crohn's disease, ulcerative colitis, collagenous colitis, lymphocytic colitis, diversion colitis, Behcet's disease, intermediate colitis, short bowel syndrome, ulcerative proctitis, proctosigmoiditis, left-sided colitis, pancolitis, and fulminant colitis. In some embodiments, the disease or condition is an autoimmune disorder selected from the group consisting of acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, asthma, ulcerative colitis, undifferentiated connective tissue disease (UCTD), uveitis, vasculitis, vesiculobullous dermatosis, vitiligo, and Wegener's granulomatosis. In some embodiments, the invention provides methods for reducing, ameliorating, or eliminating one or more symptom(s) associated with these diseases, including but not limited to diarrhea, bloody stool, mouth sores, perianal disease, abdominal pain, abdominal cramping, fever, fatigue, weight loss, iron deficiency, anemia, appetite loss, weight loss, anorexia, delayed growth, delayed pubertal development, and inflammation of the skin, eyes, joints, liver, and bile ducts. In some embodiments, the invention provides methods for reducing gut inflammation and/or enhancing gut barrier function, thereby ameliorating or preventing a systemic autoimmune disorder, e.g., asthma (Arrieta et al., 2015).

In some embodiments, the disclosure provides methods for treating a disease or disorder associated with hyperammonemia by administering engineered microorganisms, e.g., genetically engineered bacteria (e.g., comprising a modified arginine biosynthesis pathway, e.g., deleted arginine repressor, modified arginine repressor binding sites, and/or arginine feedback resistant N-acetylglutamate synthase mutation), as measured, dosed, and/or manufactured using, e.g., the live cell counting methods disclosed herein. In some embodiments, the disorder is a urea cycle disorder such as argininosuccinic aciduria, arginase deficiency, carbamoylphosphate synthetase deficiency, citrullinemia, N-acetylglutamate synthetase deficiency, and ornithine, transcarbamylase deficiency. In alternate embodiments, the disorder is a liver disorder such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth. In some embodiments, the hyperammonemia is associated with Huntington's disease. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia. In some embodiments, the disorder is a cancer, e.g., wherein the cancer's tumor microenvironment is associated with increased ammonia.

In some embodiments, the disclosure provides methods for treating cancer by administering engineered microorganisms, e.g., genetically engineered bacteria (e.g., comprising at least one gene for producing an anti-cancer molecule, e.g., dacA or an enzyme capable of producing a STING agonist), as measured, dosed, and/or manufactured using the methods for characterizing, dosing, and determining the activity disclosed herein, e.g., live cell counting method. In some embodiments, the cancer is selected from adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, gestational trophoblastic disease, heart cancer, Kaposi sarcoma, kidney cancer, largyngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer, lymphoma (e.g., AIDS-related lymphoma, Burkitt lymphoma, cutaneous T cell lymphoma, Hogkin lymphoma, Non-Hogkin lymphoma, primary central nervous system lymphoma), malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), small intestine cancer, stomach cancer, teratoid tumor, testicular cancer, throat cancer, thymus cancer, thyroid cancer, unusual childhood cancers, urethral cancer, uterine cancer, uterine sarcoma, vaginal cancer, vulvar cancer, Waldenström macroglobulinemia, and Wilms tumor.

In some embodiments, the method of treatment comprises administering engineered microorganisms, e.g., genetically engineered bacteria, or compositions or formulations thereof that are non-pathogenic, commensal, or probiotic measured using the methods for characterizing, dosing, and determining the activity disclosed herein, e.g., live cell counting method. In some embodiments, the method of treatment comprises administering genetically engineered bacteria comprise a gene encoding at least one PME, e.g., PAL and/or LAAD, wherein the PME gene is operably linked to an inducible promoter. In some embodiments, the method of treatment comprises administering genetically engineered bacteria that comprise a non-native PME gene, e.g., additional copies of a native PME gene. In some embodiments, the promoter is not associated with the PME gene in nature. In some embodiments, the method of treatment comprises administering genetically engineered bacteria that further comprise a phenylalanine transporter, e.g., PheP. In some embodiments, the method of treatment comprises administering genetically engineered bacteria that comprise a non-native phenylalanine transporter gene, e.g., additional copies of a native phenylalanine transporter gene. In some embodiments, the promoter is not associated with the phenylalanine transporter gene in nature. In some embodiments, the promoter is a thermoregulated promoter or a promoter induced under low-oxygen or anaerobic conditions. In some embodiments, the inducible promoters are induced prior to administration to the subject. In some embodiments, the inducible promoters are induced after administration to the subject. In some embodiments, the bacteria manufactured by the methods disclosed herein are auxotrophs for one or more essential genes, e.g., thyA or dapA.

In some embodiments, the method of treatment comprises administering engineered microorganismal, e.g., genetically engineered bacterial, compositions or formulations as determined using live cell counting, wherein the composition or formulation comprises at least about 40%, 45%, 50%, 55%, 60%, 65%, 70%, 75%, 80%, 81%, 82%, 83%, 84% 85%, 86%, 87%, 88%, 89%, 90%, 91%, 92%, 93%, 94% 95%, 96%, 97%, 98%, or 99% live cells, e.g., the number of living cells divided by the total number of cells.

In some embodiments, the method of treatment comprises administering genetically engineered bacterial compositions or formulations as determined using live cell counting, wherein the composition or formulation comprises no more than approximately $1.9\times10^8\pm1.8\times10^8$ EU/gram of endotoxin, no more than approximately $4.0\times10^8$ EU/gram of endotoxin, no more than approximately $3.0\times10^8$ EU/gram of endotoxin, no more than approximately $2.0\times10^8$ EU/gram of endotoxin, no more than approximately $1.0\times10^8$ EU/gram of endotoxin, or no more than approximately $5\times10^7$ EU/gram of endotoxin.

In some embodiments, the method of treatment comprises administering engineered microorganisms, e.g., genetically engineered bacteria, compositions or formulations as determined using the methods for characterizing, dosing, and determining the activity disclosed herein, e.g., live cell counting method, wherein the composition or formulation is capable of producing TCA at a rate of at least approximately 0.5 μmol/hour/$10^9$ cells, at least approximately 1.0 μmol/hour/$10^9$ cells, at least approximately 1.9±1.2 μmol/hour/$10^9$ cells, approximately 1.5-10.0 μmol/hour/$10^9$ cells, or approximately 1.5-5.0 μmol/hour/$10^9$ cells.

In some embodiments, the method of treatment comprises administering engineered microorganisms, e.g., genetically engineered bacteria, compositions or formulations as determined using the methods for characterizing, dosing, and determining the activity disclosed herein, e.g., live cell counting method, wherein the composition or formulation is capable of producing PPA at a rate of at least approximately 1.0 μmol/hour/$10^9$ cells, at least approximately 1.5 μmol/hour/$10^9$ cells, at least approximately 2.9±0.7 μmol/hour/$10^9$ cells, approximately 2.0-10.0 μmol/hour/$10^9$ cells, or approximately 2.0-5.0 μmol/hour/$10^9$ cells.

In some embodiments, the method of treatment comprises administering engineered microorganisms, e.g., genetically engineered bacteria, compositions or formulations as determined using the methods for characterizing, dosing, and determining the activity disclosed herein, e.g., live cell counting method, wherein the composition or formulation comprises 1-20% trehalose, 1-10% trehalose, 5-15% trehalose, 7-13% trehalose, 9-11% trehalose, or about 10% trehalose in a biological buffer covering a pH range of 6-8, where the biological buffer may be PIPES, MOPS, HEPES, and/or Tris buffer. In some embodiments, the composition or formulation comprises 1-400 mM Tris buffer. In some embodiments, the composition or formulation comprises 1-300 mM Tris buffer. In some embodiments, the composition or formulation comprises 1-200 mM Tris buffer. In some embodiments, the composition or formulation comprises 1-100 mM Tris buffer. In some embodiments, the composition or formulation comprises 1-50 mM Tris buffer. In some embodiments, the composition or formulation comprises 1-10 mM Tris buffer. In some embodiments, the disclosure provides a method for manufacturing a pharmaceutical composition comprising lyophilized bacteria. In some embodiments, the percent water content of the lyophilized bacteria is approximately 1-10%. In some embodiments, the percent water content is approximately 3-8%. In some embodiments, the percent water content is approximately 3-6%. In some embodiments, the percent water content is approximately 3-5%. In some embodiments, the percent water content is approximately 3%, approximately 4%, or approximately 5%.

Exemplary diseases, disorders, and methods of treatment are provided in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety.

EXAMPLES

Example 1: Construction of Bacteria

To facilitate inducible production of PAL in *Escherichia coli* Nissle, the PAL gene of *Anabaena variabilis* ("PAL1") or *Photorhabdus luminescens* ("PAL3"), as well as transcriptional and translational elements, were synthesized (Gen9, Cambridge, MA) and cloned into vector pBR322. The PAL gene was placed under the control of an inducible promoter. Low-copy and high-copy plasmids were generated for each of PAL 1 and PAL3 under the control of an inducible FNR promoter or a Tet promoter. Each of the plasmids described herein was transformed into *E. coli*, e.g., *E. coli* Nissle, for the studies described herein according to the following steps. All tubes, solutions, and cuvettes were pre-chilled to 4° C. An overnight culture of *E. coli* Nissle was diluted 1:100 in 5 mL of lysogeny broth (LB) containing ampicillin and grown until it reached an OD600 of 0.4-0.6. The *E. coli* cells were then centrifuged at 2,000 rpm for 5 min at 4° C., the supernatant was removed, and the cells were resuspended in 1 mL of 4° C. water. The *E. coli* were again centrifuged at 2,000 rpm for 5 min at 4° C., the supernatant was removed, and the cells were resuspended in 0.5 mL of 4° C. water. The *E. coli* were again centrifuged at 2,000 rpm for 5 min at 4° C., the supernatant was removed, and the cells were finally resuspended in 0.1 mL of 4° C. water. The electroporator was set to 2.5 kV. Plasmid (0.5 μg) was added to the cells, mixed by pipetting, and pipetted into a sterile, chilled cuvette. The dry cuvette was placed into the sample chamber, and the electric pulse was applied. One mL of room-temperature SOC media was added immediately, and the mixture was transferred to a culture tube and incubated at 37° C. for 1 hr. The cells were spread out on an LB plate containing ampicillin and incubated overnight.

In some embodiments, the PAL was inserted into the Nissle genome. Gibson assembly was used to add 1000 bp sequences of DNA homologous to the Nissle malP and malT loci and to clone this sequence between the homology arms. Successful insertion of the fragment into a KIKO plasmid was validated by sequencing. PCR was used to amplify the entire region. This knock-in PCR fragment was used to transform an electrocompetent Nissle strain expressing the lambda red recombinase genes. After transformation, cells were grown for 2 hrs at 37° C. Transformants with successful integration at the malPT intergenic region were selected on kanamycin at 50 μg/mL.

In some embodiments, a non-native copy (e.g., a second copy of native) high affinity of the phenylalanine transporter, PheP, driven by an inducible promoter, was inserted into the Nissle genome through homologous recombination. Gibson assembly was first used to add 1000 bp sequences of DNA homologous to the Nissle lacZ locus into the R6K origin plasmid pKD3. This targets DNA cloned between these homology arms to be integrated into the lacZ locus in the Nissle genome. PCR was used to amplify the region from this plasmid containing the entire sequence of the homology arms, as well as the pheP sequence between them. This PCR fragment was used to transform electrocompetent Nissle-pKD46, a strain that contains a temperature-sensitive plasmid encoding the lambda red recombinase genes. After transformation, cells were grown for 2 hrs before plating on chloramphenicol at 20 μg/mL at 37° C. Growth at 37° C. cures the pKD46 plasmid. Transformants containing anhydrous tetracycline (ATC)-inducible pheP were lac-minus (lac-) and chloramphenicol resistant. In some embodiments, the phenylalanine transporter may be on a plasmid transformed into Nissle.

In some embodiments, LAAD driven by an inducible promoter was inserted into the Nissle genome as described herein. Overnight cultures were diluted 1:100 and grown to early log phase before induction with ATC (100 ng/ml) for 2 hours. Cells were spun down and incubated as follows. Cells (1 ml) were incubated aerobically in a 14 ml culture tube, shaking at 250 rpm. For microaerobic conditions, cells (1 ml) were incubated in a 1.7 ml conical tube without shaking. Cells were incubated anaerobically in a Coy anaerobic chamber supplying 90% N2, 5% CO2, and 5%

H2. In some embodiments, the LAAD may be on a plasmid transformed into Nissle.

Exemplary phenylalanine-metabolizing enzymes, PAL, LAAD, promoters (e.g., FNR promoters), phenylalanine transporters (e.g., PheP), organization and nucleotide sequences of these constructs, and methods of generating these constructs are shown in WO2017087580. Other promoters may be used to drive expression of the genes and other genes, e.g., phenylalanine-metabolizing genes, may be used.

An exemplary bacterium is phenylalanine metabolizing bacterium SYNB1618. See Isabella et al., 2018 Development of a synthetic live bacterial therapeutic for the human metabolic disease phenylketonuria. SYNB1618 was engineered with two chromosomally integrated copies of pheP and three copies of stlA under the regulatory control of the anaerobic-inducible promoter PfnrS. The PfnrS promoter was inactive in the presence of oxygen and was activated under anaerobic or microaerobic conditions by the anoxic-sensing transcriptional activator FNR. A PfnrS-GFP transcriptional fusion in *E. coli* Nissle was used to confirm the activation of this promoter following oral administration in C57BL/6 mice and recovery from the gastrointestinal tract. Two additional copies of stlA were placed under the control of the Ptac promoter, which allowed induction by isopropyl β-d-1-thiogalactopyranoside (IPTG) in vitro. SYNB1618 contains a copy of pma under the control of the arabinose-inducible PBAD promoter.

Example 2: Processes

Lyophilization

After fermentation and downstream processing to get the cells into the lyophilization buffer, load cell suspension material into lyophilization trays at a fill depth of 15 mm. Use the lyophilizer to perform the following cycle: freeze material at a temperature of −40° C., with primary drying at −15° C., and secondary drying at 5° C. After completion of the lyophilization cycle, the lyophilized cake is sieved through a 80-mesh screen into a free flowing powder Spray Drying After fermentation and downstream processing to get the cells into the spray drying buffer, the cell suspension is spray dried through a 2-fluid nozzle with an inlet temperature of 120-135° C. targeting an outlet temperature of 60° C. resulting in a free flowing powder Frozen Liquid After fermentation and downstream processing to get the cells into the cryoprotectant buffer, the cell suspension is frozen at −80° C.

Example 3: Live Cell Counting

Live cell counts and viability were obtained using a Nexcelom Cellometer. For the formulations comprising bacteria in frozen liquid, a sample was thawed in a 37° C. water bath. For the formulations comprising lyophilized and spray dried bacteria, 1 g was weighed into a vial and rehydrated with 6 mL of PBS. All cell samples were then diluted 1:1000 in PBS, with a further 1:1 dilution with Sytox green stain in PBS or HBSS (total of 1:2000 dilution). 4 μL of this dilution was then transferred to a Cellometer slide. The slide was placed in the Cellometer and the brightfield and fluorescence images were obtained. Live cell counts were calculated from the difference in the number of cells detected by brightfield (total cells) and the number of cells detected with fluorescence (non-living cells). Viability was calculated as the number of live cells/the number of total cells.

Example 4: In Vitro Activity of Formulations Comprising Frozen Liquid, Lyophilized, or Spray Dried Bacteria Compositions of bacterial comprising lyophilized, frozen liquid, and spray dried bacteria prepared according to the methods disclosed in Example 2 were characterized for activity in vitro. Table 2 shows exemplary characteristics of phenylalanine metabolizing bacteria that have been prepared by Process 1 (frozen liquid) or Process 2 (solid batch, lyophilized).

TABLE 2

| | Process 1 | Process 2 | | |
|---|---|---|---|---|
| Characteristics (Unit) | Frozen Liquid | Solid Batch 1 | Solid Batch 2 | Solid Batch 3 |
| CFU (mL) | $8.07 \times 10^{10}$ | $5.65 \times 10^{10}$ | $1.49 \times 10^{10}$ | $2.15 \times 10^{10}$ |
| Total Cell (mL) | $2.59 \times 10^{11}$ | $1.29 \times 10^{11}$ | $1.38 \times 10^{11}$ | $1.34 \times 10^{11}$ |
| Live Cell (mL) | $2.2 \times 10^{11}$ | $1.08 \times 10^{11}$ | $1.19 \times 10^{11}$ | $1.16 \times 10^{11}$ |
| Viability (%) | 89% | 84% | 86% | 87% |
| Activity (TCA) μmol/hr/1e9 cells | 4.34 | 2.14 | 2.36 | 1.81 |
| Activity (PPA) μmol/hr/1e9 cells | 4.07 | 2.82 | 2.61 | 3.05 |
| Free DNA (μg/mL) | 207 | 195 | 111 | 85 |
| Free Protein (μg/mL) | 11,808 | 5,804 | 3,328 | 3,677 |
| Free Endotoxin (EU/mL) | $4.6 \times 10^{7}$ | $1.78 \times 10^{7}$ | $3.91 \times 10^{7}$ | $3.66 \times 10^{7}$ |
| Viscosity (cP) | 445 | 34 | 36 | 31 |

Example 5: In Vitro Simulation (IVS) Gut Model

Figure 9:
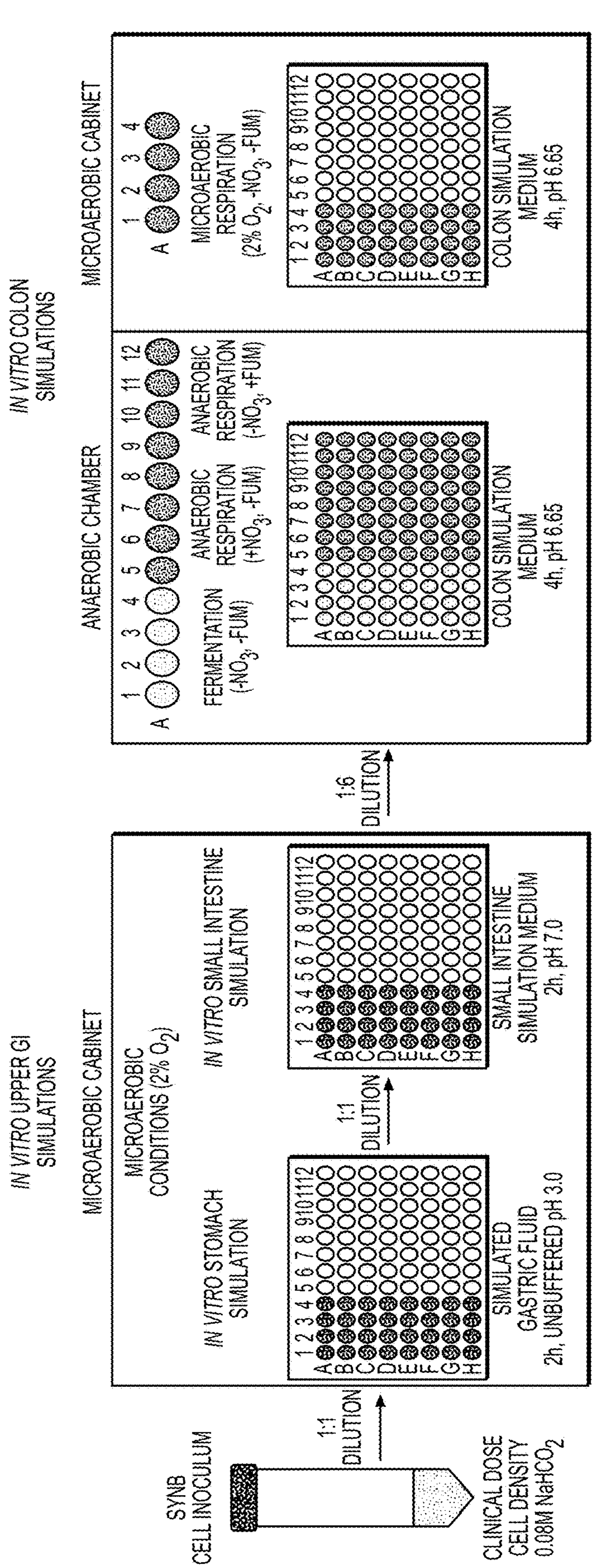
FIG. 9 depicts a schematic of the In Vitro Simulated (IVS) gut model.
Figure 11:
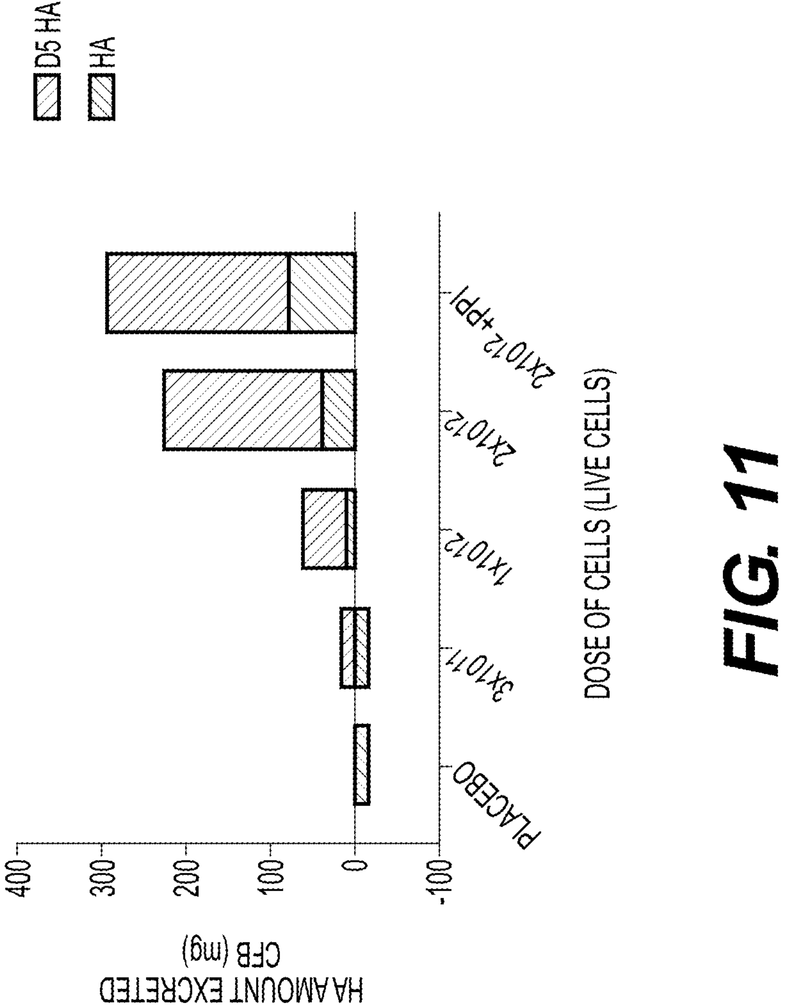
FIG. 11 shows urinary hippurate (HA) and labeled D5-HA using a solid oral (lyophilized) formulation. CFB=change from baseline. CFP=change from placebo.

To characterize the viability and metabolic activity of engineered bacterial strains, and to predict their function in vivo, the in vitro simulation (IVS) gut model was designed to simulate key aspects of the human gastrointestinal transit, including oxygen concentration, gastric and pancreatic enzymes, and bile. The IVS model comprises a series of incubations in 96-well microplate format designed to simulate stomach, small intestine, and colonic conditions (FIG. 9). To study engineered strains designed for the treatment of phenylketonuria, simulated stomach and small intestine were considered. The stomach and small intestinal portions of the IVS model were adapted from Minekus et al. (2014) A standardised static in vitro digestion method suitable for food—an international consensus.

To simulate gut transit, frozen aliquots of bacterial cells were first thawed at room temperature. Lyophilized bacterial cell material were stored at 4° C. and did not require thawing. Bacterial cell concentration was measured by CFU plating or by counts of live and/or total cells by cellometer. Aliquots of bacterial cells were resuspended in 0.077M sodium bicarbonate buffer at $5.0\times10^9$ cells per mL. This solution was then mixed with equal parts of simulated gastric fluid (SGF; see Tables 1 and 2) and incubated for 2 hours at 37° C. with shaking in a Coy microaerobic chamber calibrated to 2% oxygen. The cell density in SGF was $2.5\times10^9$ cells/mL. For the study of engineered strains designed to consumed phenylalanine (Phe), SGF was amended with 20 mM Phe. After two hours of SGF incubation, an equal volume of simulated intestinal fluid (SIF; see Tables 3 and 4) was added to the SGF-sodium bicarbonate mix and incubated for an additional 2 hours at 37° C. with shaking in a Coy microaerobic chamber calibrated to 2% oxygen. The cell density when mixed with SIF was $1.25\times10^9$ cells/mL.

To determine bacterial viability over time in IVS studies, SGF and SIF aliquots were collected and subjected to serial dilution and plating on LB agar plates, followed by overnight incubation at 37° C. and subsequent CFU counting. In the case of strains harboring an auxotrophy for diaminopimelic acid (DAP), LB agar plates were supplemented with 100 μg/mL DAP. Alternatively, bacterial viability over time was determined by counting live and/or total cells by cellometer. To determine the consumption of Phe, SGF and SIF aliquots were collected periodically and centrifuged at 4000 rpm for 5 mins using a table top centrifuge. Cell-free supernatant was then collected for LC-MS/MS quantification of metabolites, including Phe, trans-cinnamate (TCA), and phenylpyruvate (PP). Cell free supernatants were optionally stored at −20° C. until LC-MS/MS analysis.

TABLE 3

Composition of 1.25× Simulated Gastric Fluid (1.25× SGF)

| Component | Formula Weight [g/mol] | Stock Concentration [M] | Concentration in 1× SGF [mM] | Amount for 400 mL 1.25× SGF [g] | Amount for 400 mL 1.25× SGF (mL) |
|---|---|---|---|---|---|
| KCl | 74.5513 | 0.5 | 6.9 | 0.2572 | N/A |
| KH2PO4 | 136.086 | 0.5 | 0.9 | 0.0612 | N/A |
| NaHCO3 | 84.007 | 1 | 25 | 1.0501 | N/A |
| NaCl | 58.4 | 2 | 47.2 | 1.3782 | N/A |
| MgCl2(H2O)6 | 203.3 | 0.15 | 0.1 | 0.0102 | N/A |
| (NH4)2CO3 | 96.09 | 0.5 | 0.5 | 0.0240 | N/A |
| HCl | 36.46 | 6 | 15.6 | N/A | 1.3 |

TABLE 4

Composition of Simulated Gastric Fluid (SGF)

| Component | Concentration | Volume for One Sample [uL] |
|---|---|---|
| SYNB Cell Inoculum (prepared in Sodium Bicarbonate) | 1× | 250 |
| 1.25× Simulated Gastric Fluid | 1.25× | 187.5 |
| HCl Stock Solution | 1 M | 4 |
| Porcine Pepsin Stock Solution | 25,000 U/mL in SGF | 40 |
| CaCl2 Stock Solution | 0.3 M | 0.125 |
| Water (Sterile) | N/A | 18.375 |

TABLE 5

Composition of 1.25× Simulated Intestinal Fluid (1.25× SIF)

| Component | Formula Weight [g/mol] | Stock Concentration [M] | Concentration in 1× SIF [mM] | Amount for 400 mL 1.25× SIF [g] | Amount for 400 mL 1.25× SGF (mL) |
|---|---|---|---|---|---|
| KCl | 74.5513 | 0.5 | 6.8 | 0.2535 | N/A |
| KH2PO4 | 136.086 | 0.5 | 0.8 | 0.0544 | N/A |
| NaHCO3 | 84.007 | 1 | 85 | 3.5703 | N/A |
| NaCl | 58.4 | 2 | 38.4 | 1.1213 | N/A |
| MgCl2(H2O)6 | 203.3 | 0.15 | 0.33 | 0.0335 | N/A |
| (NH4)2CO3 | 96.09 | 0.5 | 0 | 0.0000 | N/A |
| HCl | 36.46 | 6 | 8.4 | N/A | 0.70 |

TABLE 6

| Composition of Simulated Intestinal Fluid (SIF) | | |
|---|---|---|
| Component | Concentration | Volume for One Sample [uL] |
| Simulated Gastric Chyme | 1× | 500 |
| Simulated Intestinal Fluid | 1.25× | 275 |
| Pancreatin Solution | 800 Trypsin U/mL in SIF | 125 |
| Bile Salts | 160 mM in SIF | 62.5 |
| CaCl2 Stock Solution | 0.3 M | 1 |
| HCl Stock Solution | 1 M | 7.5 |
| Water | N/A | 29 |

Example 6: Live Cell Count and CFU Methods

Beginning at least 4 days prior to the study, non-naïve homozygous female BTBR-Pah$^{enu2/enu2}$ mice (approx. 15-25 weeks of age) were placed on phenylalanine-free chow and water that was supplemented with 0.5 grams/L phenylalanine. On Day 1, mice were weighed and randomized into groups based on body weight. Mice were then administered bacteria orally and immediately transferred to metabolic cages. Two additional doses were administered one and two hours post first bacteria dose, respectively. Three hours post first bacteria dose, total urine samples were collected and the volume was recorded. Animals were returned to home cages once the study was completed.

To prepare the cells, SYN094 and frozen liquid SYNB1618 (SYNB1618 Batch A) were thawed at 37 degrees Celsius. Lyophilized (Batch C) and spray dried (Batch D) SYNB1618 were prepared by the formulation group. Cells were diluted with PBS to 5.03e10 live cells/mL and mixed 9:1 in 1M sodium bicarbonate. Each mouse was gavaged 900 uL in total, which amounted to 4.08e10 live cells/mouse.

Figure 5B:
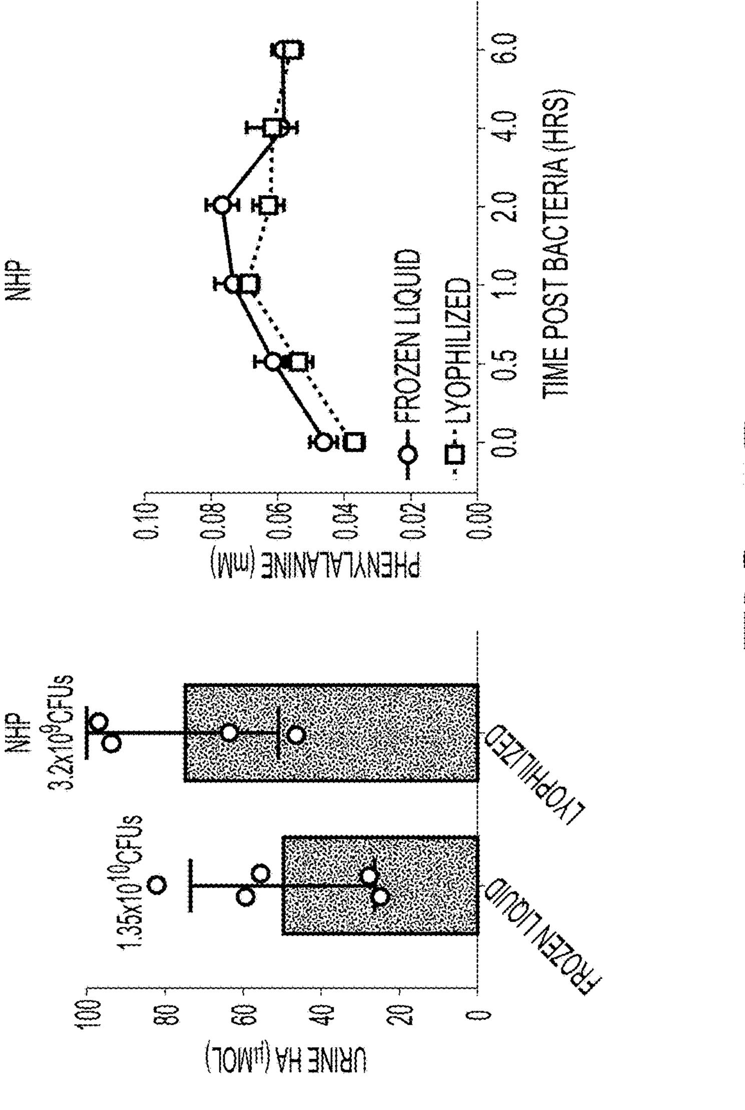
FIG. 5B depicts in vivo activity in non-human primate (NHP) of phenylalanine metabolizing bacteria (frozen or lyophilized). All groups of NHPs were administered bacterial compositions having approximately the same live cell count. The bar graph illustrates urine HA levels measured at a single time point. The scatter plot illustrates phenylalanine levels measured at multiple time points.
Figure 5A:
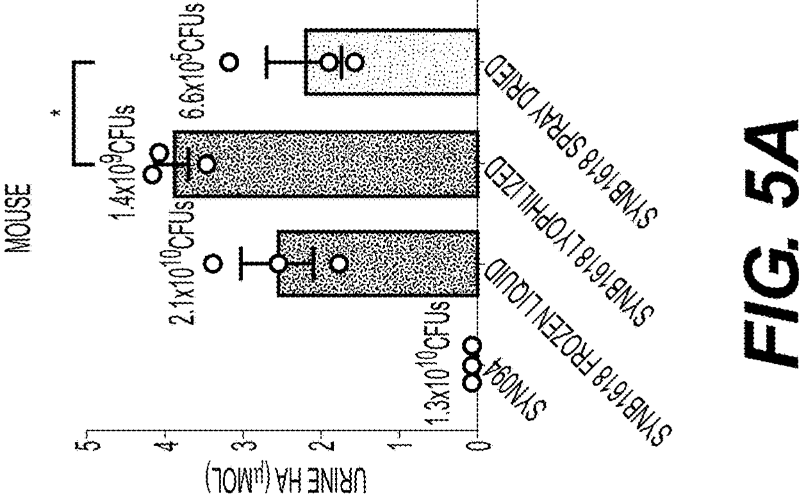
FIG. 5A depicts a graph showing the in vivo activity in mice of phenylalanine metabolizing bacteria SYNB1618 (frozen, lyophilized, or spray dried). All groups of mice were administered bacterial compositions having approximately the same live cell count.
Figure 7B:
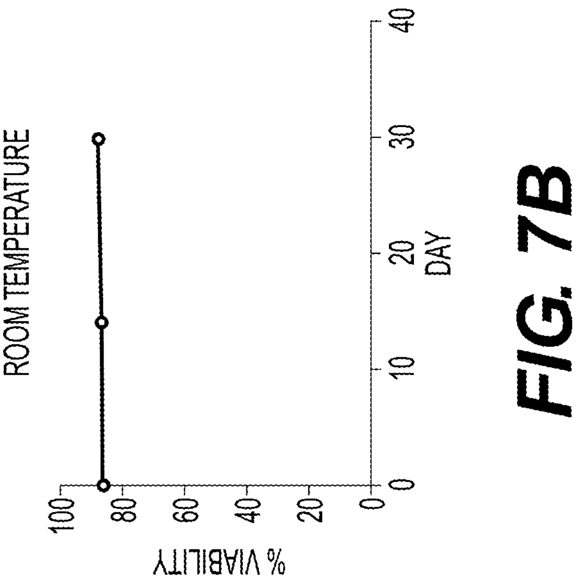
FIG. 7B depicts the stability of lyophilized bacteria stored at room temperature.
Figure 7A:
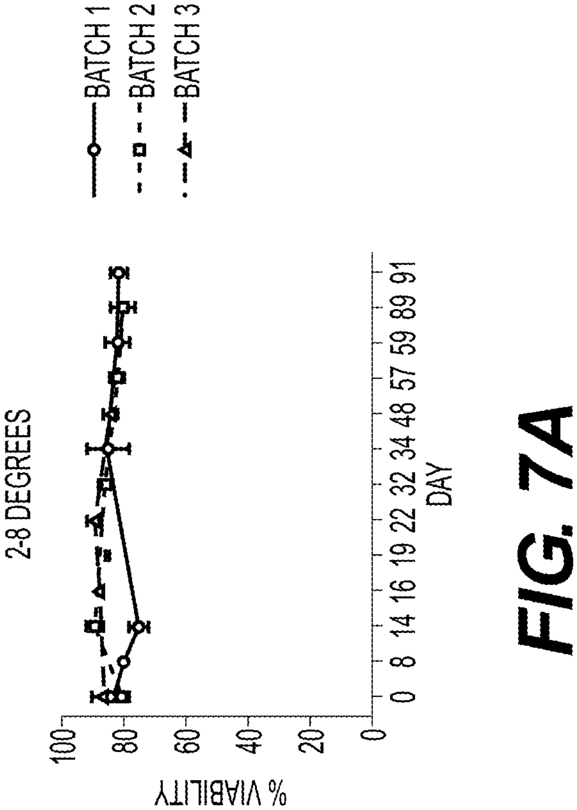
FIG. 7A depicts a graph illustrating the stability of three batches of phenylalanine metabolizing bacteria prepared using the same method (solid batch). Here, % viability is calculated as the number of live cells divided by the total number of cells. Bacteria were stored between 2-8° C.

Urine samples were collected at 3 hours post first bacteria dose. Urinary hippuric acid (HA) levels were measured using mass spectrometry. See, e.g., WO2017087580. The total amount of hippuric acid measured is depicted in FIG. 5A, and for SYN094 was 0.031 μmol±0.006, 2.569 μmol±0.468 for frozen liquid SYNB1618, 3.926 μmol±0.222 for lyophilized SYNB1618, and 2.217 μmol±0.495 for spray dried SYNB1618. HA levels measured in lyophilized and spray dried SYNB1618 were not different from frozen liquid SYNB1618, but lyophilized SYNB1618 resulted in significantly higher HA recovery than spray dried SYNB1618.

Example 7: Live Cell Count and CFU Methods

Beginning at least 4 days prior to the study, non-naïve homozygous female BTBR-Pah$^{enu2/enu2}$ mice (approx. 12-22 weeks of age) were placed on phenylalanine-free chow and water that was supplemented with 0.5 grams/L phenylalanine. On Day 1, mice were weighed and randomized into groups based on body weight. Mice were then administered bacteria orally and immediately transferred to metabolic cages. Two additional doses were administered one and two hours post first bacteria dose, respectively. Three hours post first bacteria dose, total urine samples were collected and the volume was recorded. Animals were returned to home cages once study was completed.

To prepare the cells, frozen liquid SYNB1618 (SYNB1618 Batch A) was thawed at 37 degrees Celsius. Lyophilized and spray dried (Batch B) SYNB1618 were prepared by the formulation group. Cells were diluted with PBS to 6.17e10 live cells/mL and mixed 9:1 in 1M sodium bicarbonate. Each mouse was gavaged 900 uL in total, which amounted to 5e10 live cells/mouse.

Urine samples were collected at 3 hours post first bacteria dose. Urinary hippuric acid (HA) levels were measured using mass spectrometry. See, e.g., WO2017087580. The total amount of hippuric acid measured is depicted in FIG. 6B, and was 3.107 μmol 0.743 and 1.563 μmol±0.146 for frozen liquid and spray dried SYNB1618, and were not significantly different.

Example 8: Non-Human Primate (NHP) Studies

Ten male, non-naive cynomolgus monkeys of approximately 2 to 5 years old were randomized into 2 groups (n=5) and fasted overnight. Prior to dosing, plasma was collected for baseline phenylalanine levels. Animals were separated with clean collection pans for urine collection. Each animal was then administered 11 mL of 500 g/L peptone, 5 mL of 0.36M sodium bicarbonate, and either frozen liquid SYNB1618 (SYNB1618 Batch A) or lyophilized SYNB1618 ($1.3\times10^{11}$ live cells per dose). Plasma samples were collected at 0.5, 1, 2, 4, and 6 hours post dose. At conclusion of 6 hours post dose, the total amount of urine was measured, recorded, and collected.

Frozen liquid SYNB1618 (SYNB1618 Batch A) was thawed at 37° C. Lyophilized SYNB1618 was resuspended in PBS. Frozen liquid and lyophilized bacteria were both diluted with formulation buffer to $2.6\times10^{10}$ live cells/mL.

Plasma phenylalanine levels and urinary hippuric acid (HA) recovery were measured with mass spectrometry. Plasma phenylalanine levels peaked at 2 hours post dose for frozen liquid (0.0771 mM±0.005) and at 1 hour post dose for lyophilized bacteria (0.0690 mM±0.003). There was no significant difference between the 2 groups at any collection timepoint ($p>0.05$). Urinary HA recovery was 49.599 μmol±10.498 for frozen liquid SYNB1618, which was not significantly different from lyophilized SYNB1618, which was 74.770 μmol±12.044 ($p=0.1625$).

Example 9: In Vivo SYNB1618

Beginning at least 4 days prior to the study, non-naïve wildtype female C57B1/6 mice (approx. 14 weeks of age) were placed on phenylalanine-free chow and water that was supplemented with 0.5 grams/L phenylalanine. On Day 1, mice were weighed and randomized into groups based on body weight. Mice were then administered bacteria orally and immediately transferred to metabolic cages. Two additional doses were administered one and two hours post first bacteria dose, respectively. Three hours post first bacteria dose, urine samples were collected and the total volume was recorded. Animals were returned to home cages once study was completed.

To prepare the cells, Batch A (frozen liquid SYNB1618) was thawed at 37 degrees Celsius. Lyophilized solid Batch 1, 2, and 3 were prepared as described herein. Cells were diluted with PBS to 9.43e10 live cells/mL and mixed 9:1 in 1M sodium bicarbonate. Each mouse was gavaged 600 uL in total, which amounted to 5.09e10 live cells/mouse.

Urine samples were collected at 3 hours post first bacteria dose. Urinary hippuric acid (HA) levels were measured using mass spectrometry. See, e.g., WO2017087580. The total amount of hippuric acid measured is illustrated in the right hand bar graph in FIG. 8, and was 5.377 μmol±0.440, 5.353 μmol±0.995, and 5.260 μmol±0.499 for, batch 1, batch 2, and batch 3, respectively. There was no significant difference among treatment groups (p>0.05).

Example 10: Stability of Formulations Comprising Lyophilized Bacteria

Stability studies are performed on SYNB1618 Bulk Drug Product and Drug Product at 5±3° C. and 25±5° C./60±5% RH for 6 months. The study initiation was defined as the date the samples were placed in the appropriate storage conditions.

Bulk Drug Product was stored in polyethylene bags within sealed foil pouches or in sealed HDPE bottles. Both were stored in 5±3° C. and 25±5° C./60±5% RH stability chambers, and removed from storage at 2 weeks, 1 month, 2 months, 3 months and 6 months per the testing schedule. Aliquots were evaluated for Live Cells, Viability (live cells/total cells), Potency, and Solid Appearance. Results from each time point were compared to results observed on the initial time point and predefined specifications. At each time point, 5 grams of bulk drug product and 2 bottles of drug product were used for testing.

Example 11: Live Cell Counting of PKU Bacterial Strains

Bacterial strains and Sytox Green stain were prepared as previously described. Three batches of SYNB1618 (#12, #17 and CTM) were analyzed at different stain concentrations and incubation times. Data was analyzed for three main attributes: total cells/mL, live cells/mL, and % viability.

Figures 12A, 12B, 12C, 12D, 12E, 12F:
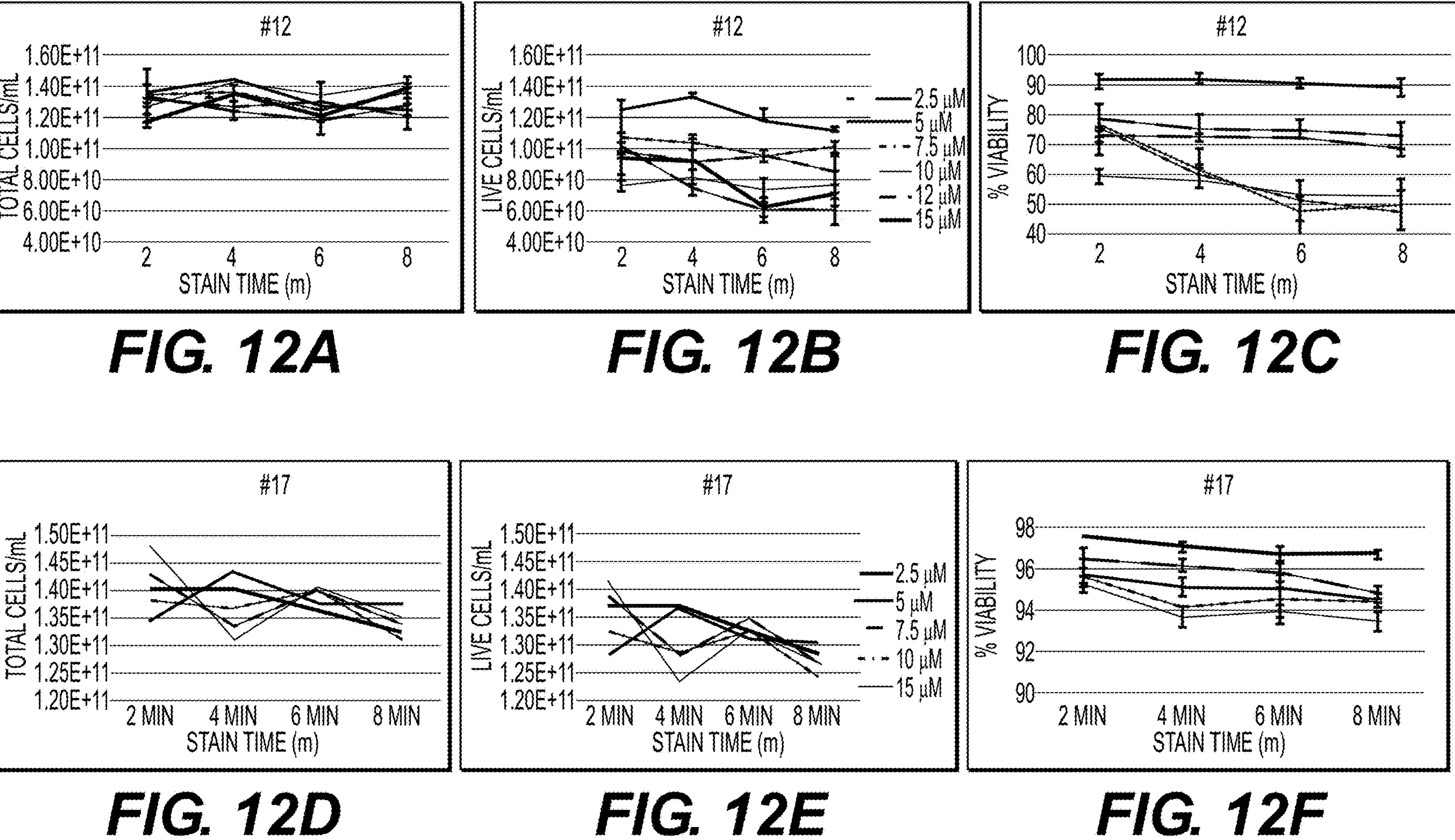
FIGS. 12A-I depicts live cell counting of exemplary genetically engineered bacteria for the treatment of a disease associated with hyperphenylalaninemia, e.g., PKU, across a range of Sytox Green concentrations and incubation times. Total cells/mL, live cells/mL and % viability were calculated.

#12 was incubated in Sytox Green concentrations of 2.5, 5, 7.5, 10, 12, and 15 uM. For each concentration, staining was conducted for 2, 4, 6, and 8 minutes. Total cells/mL was unaffected by SYTOX Green stain concentration and staining time. The average of all total cell counts across all stain concentrations and timepoints was 1.32E11 cells/mL with an SD=7.76E9 cells/mL, with a % CV of =5.88, N=24. Results for stain concentration at 2.5 μM were similar to live cells/mL at 7.5 μM. The 5 μM stain concentration yielded 1.25E11 live cells/mL. (FIG. 12A-12C).

Figures 14A, 14B, 14C:
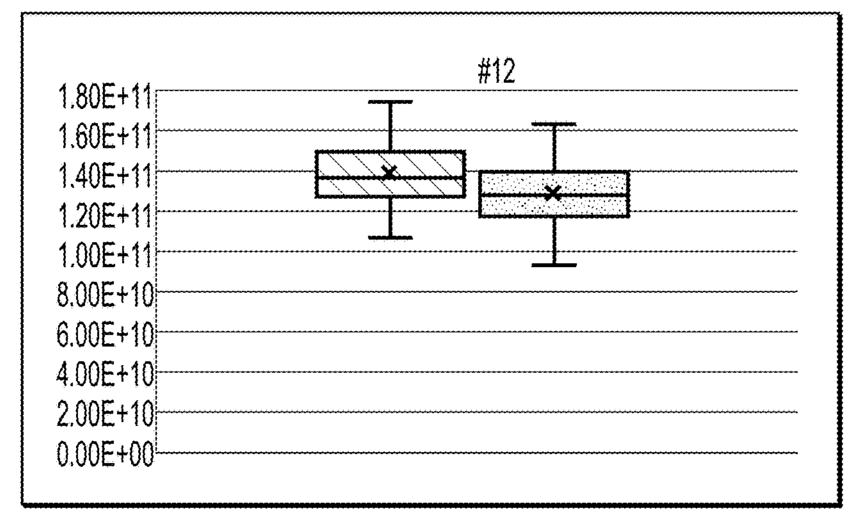
FIGS. 14A-C depicts measurements of exemplary genetically engineered bacteria for treating PKU in frozen liquid form using live cell counting. The average total, dead and live cells/mL were calculated for 33 replicates.

33 replicates of #12 in frozen liquid form were also assayed using the live cell counting method, and average total, dead, and live cells/mL were analyzed. For live cells/mL the % CV was 12.3. (FIG. 14A-14C).

Batch 17 was incubated in Sytox Green concentrations of 2.5, 5, 7.5, 10, and 15 uM. For each concentration, staining was conducted for 2, 4, 6, and 8 minutes. At any stain concentration the CV was <2%. (FIG. 12D-12F)

Figure 12H:
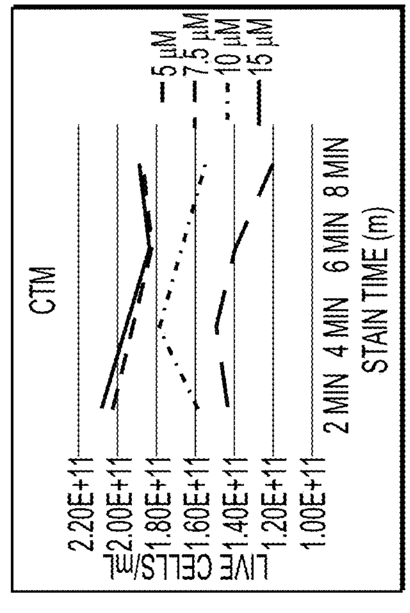
Figure 12I:
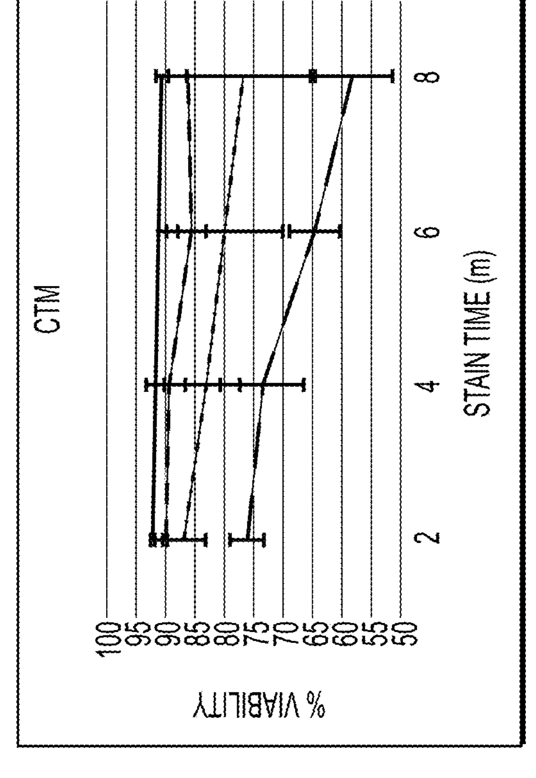
Figure 12G:
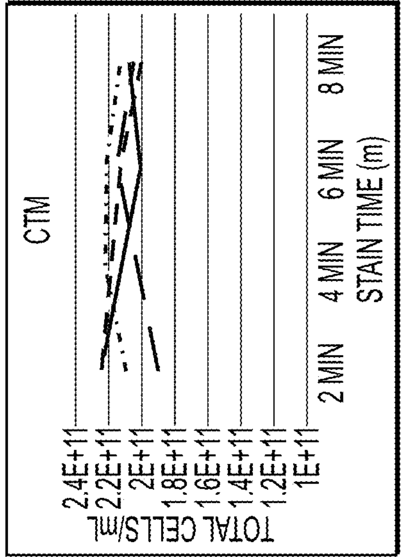

CTM was incubated in Sytox Green concentrations of 5, 7.5, 10, and 15 uM. For each concentration, staining was conducted for 2, 4, 6, and 8 minutes. Total cells/mL did not change with stain concentration and time. (FIG. 12G-12I)

Figures 13A, 13B, 13C, 13D, 13E, 13F:
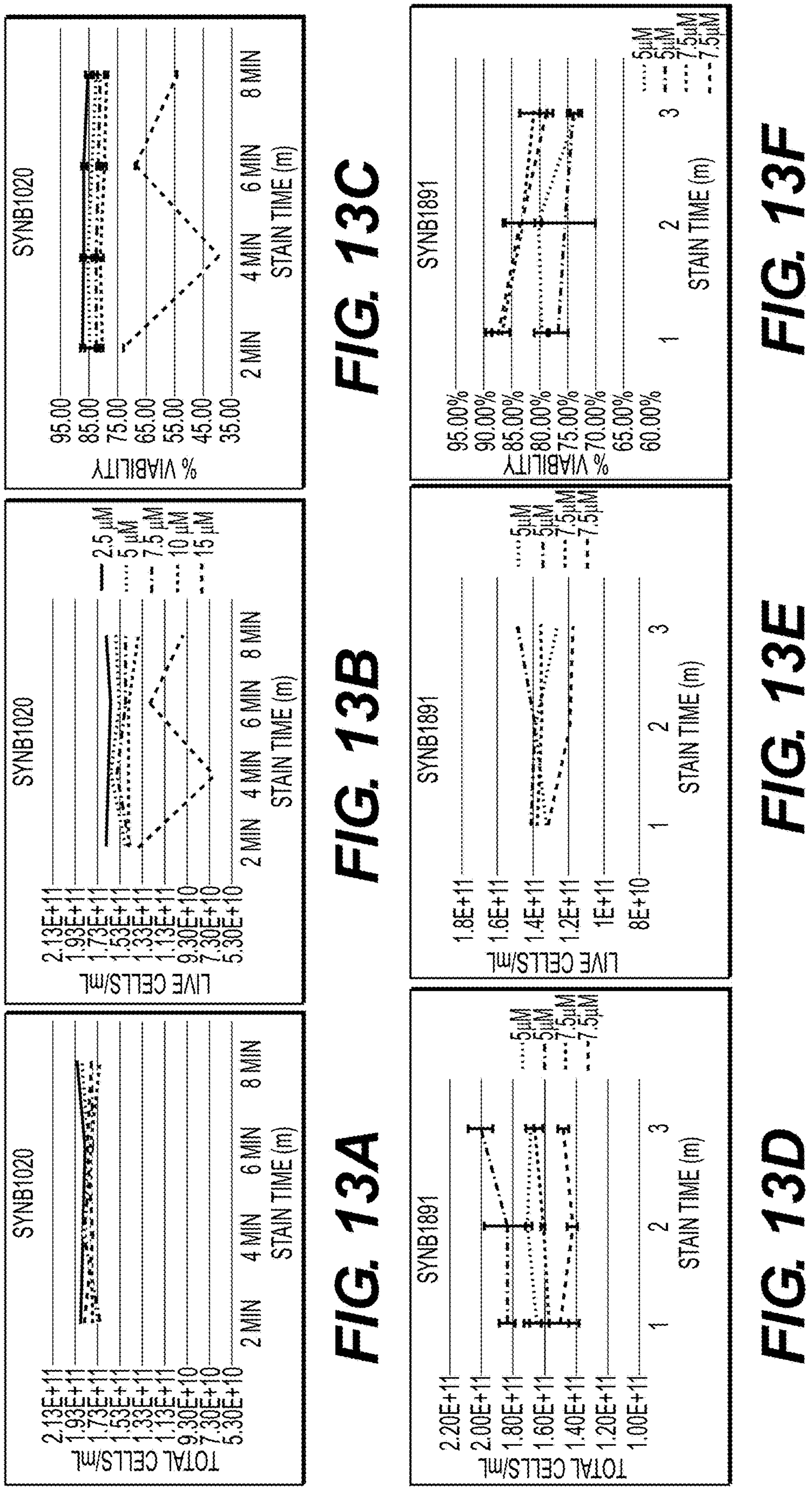
FIGS. 13A-F depicts live cell counting of exemplary genetically engineered bacteria for treating UCD (SYNB1020) and exemplary genetically engineered bacteria comprising dacA for treating cancer (SYNB1891) across a range of Sytox Green concentrations and incubation times. Total cells/mL, live cells/mL and % viability were calculated.

Example 12: Live Cell Counting of UCD and Cancer-Treatment Bacterial Strains SYNB1020 (comprising a feedback-resistant version of the N-acetylglutamate synthase enzyme ArgA, argA$^{fbr}$, and deleted arginine repressor ArgR; see Kurtz et al., An Engineered *E. coli* Nissle Improves Hyperammonemia and Survival in Mice and Shows Dose-dependent Exposure in Healthy Humans, 2019) was incubated in Sytox Green concentrations of 5, 7.5, 10, and 15 uM. For each concentration, staining was conducted for 2, 4, 6, and 8 minutes. Total cells/mL did not change over different stain concentrations or over time. (FIG. 13A-13C)

An exemplary bacterium comprising the dacA gene (SYNB1891) was incubated in Sytox Green concentrations of 5 and 7.5 uM. For each concentration, staining was conducted for 1, 2 and 3 minutes. The two replicates at 5 μM and two at 7.5 μM were very similar for live cells/mL and % viability. (FIG. 13D-13F).

Example 13: Determination of Linear Range of Live Cells/mL

Several dilutions of PKU lyophilized strain SYNB1618 were tested and cell counts obtained and analyzed for linearity. With a range of 861-2547 cells counted, $R^2$=0.84 and CV was 9.85% for back-calculated titers in this range. SYNB1618 with excipients (10% trehalose in 50 mM Tris buffer, pH 7.5) was also tested for linearity of live cells/mL and the same linear range was applicable. (FIG. 15A-15D).

Figures 15A, 15B, 15C, 15D:
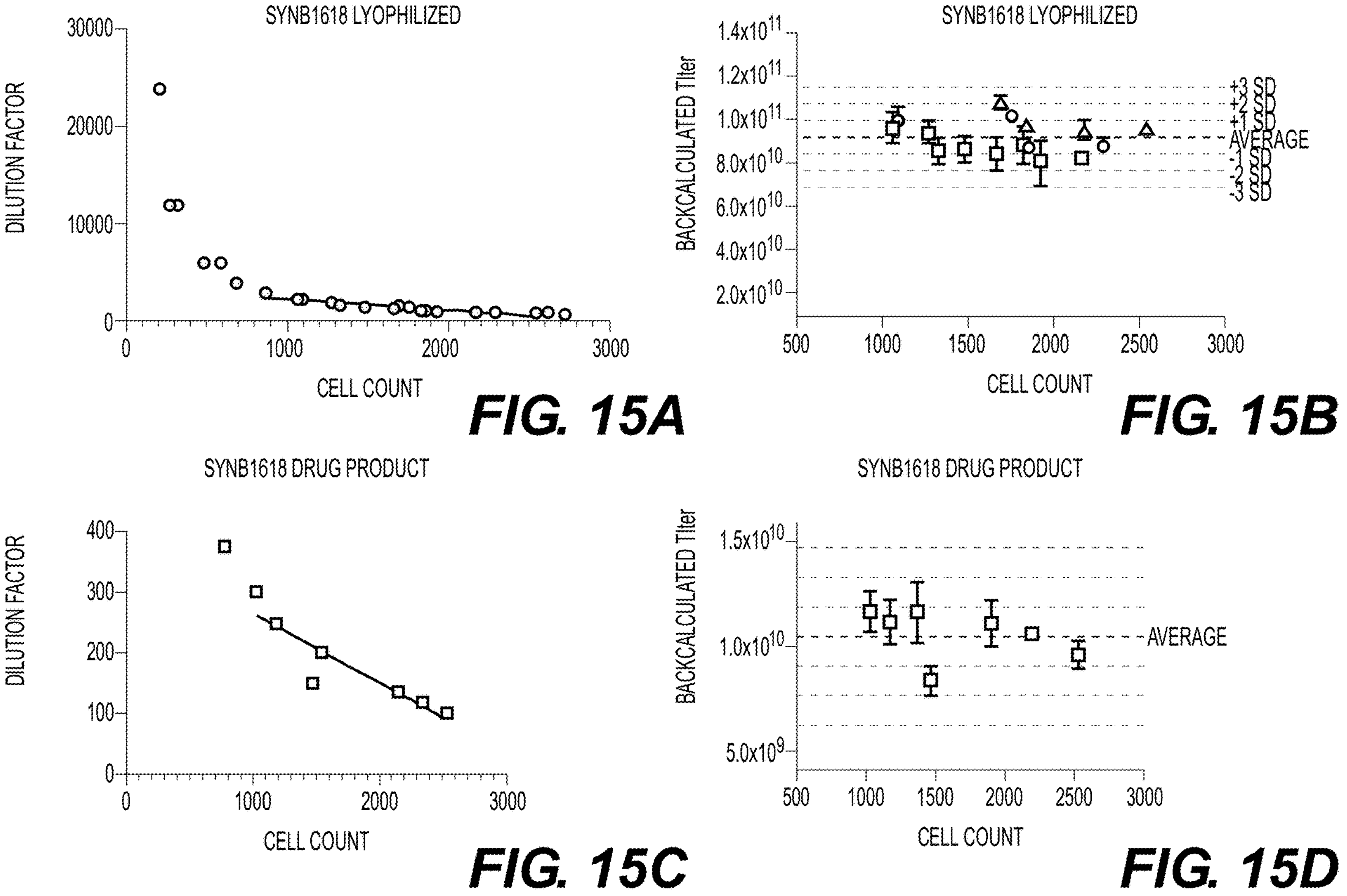
FIGS. 15A-G shows linearity of live cells/mL over a range of dilutions using exemplary genetically engineered bacteria for treating PKU (SYNB1618), as well as for exemplary genetically engineered bacteria comprising dacA for treating cancer (SYNB1891). Linearity of the percent viability measurement was also analyzed via addition of proportional amounts of killed cells to live samples.
Figures 15E, 15F:
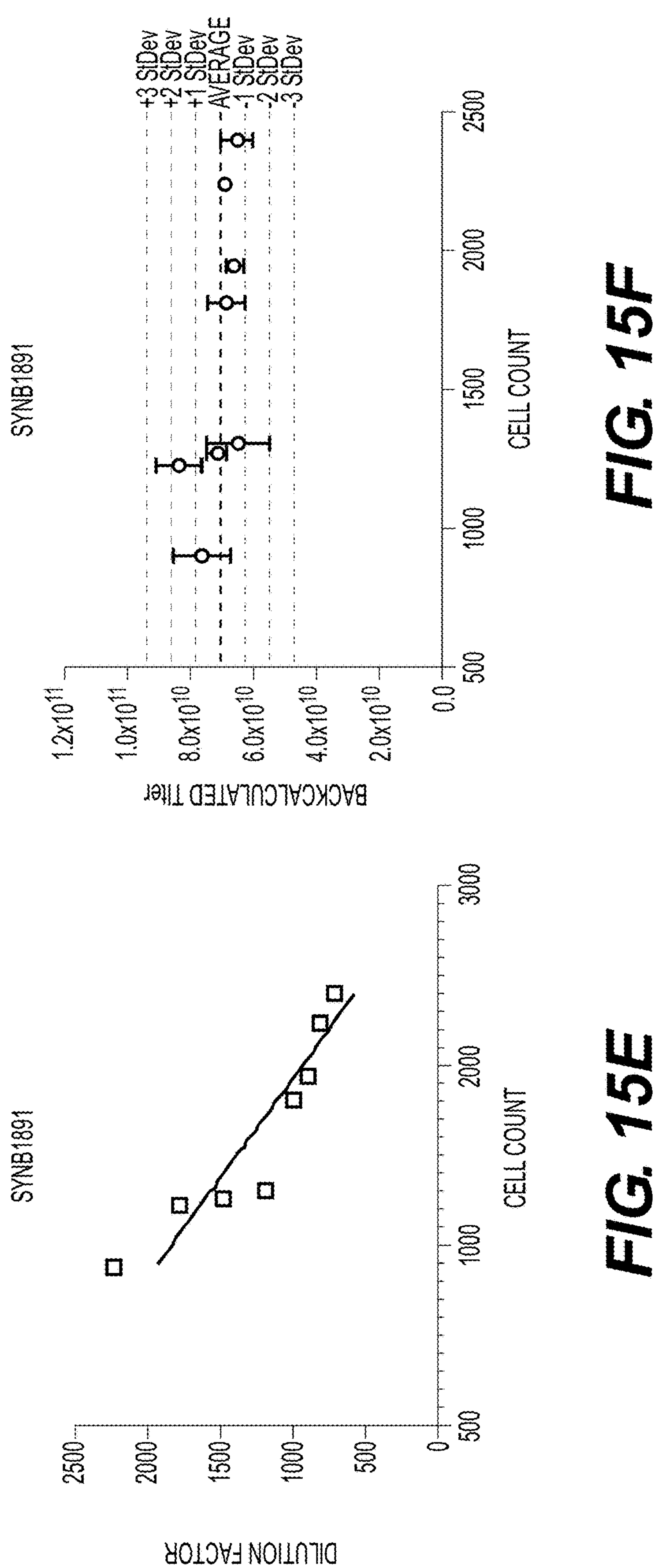

Cellometer linearity was tested for a GMP-level SYNB1891 batch. $R^2$=0.84 for the 900-2400 range. (FIGS. 15E and F)

Figure 15G:
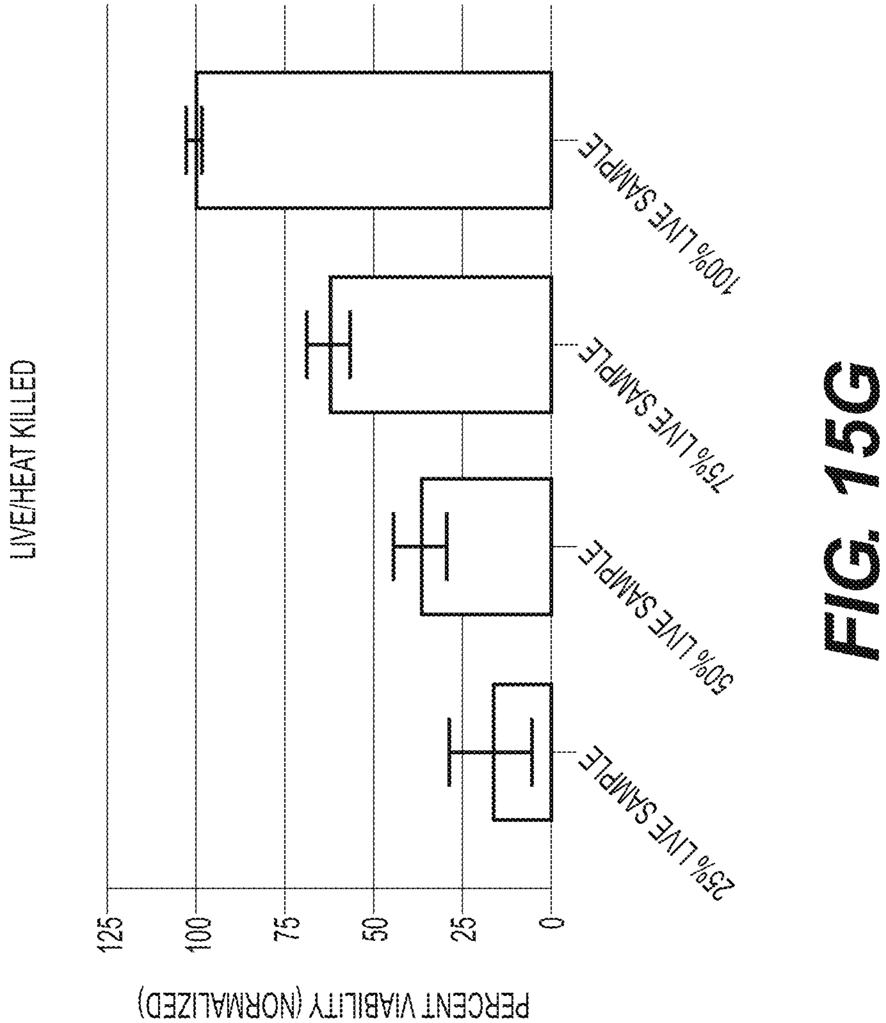

Linearity of the percent viability measurement was tested by killing some cells with heat, which permeabilizes the membrane enough to allow the SYTOX dye to bind to DNA. The killed sample was then added in various proportions to the original live sample to make mixtures of cells that were 25%, 50%, 75%, and 100% live cells. The % viability had an error of about ±7%, and the Cellometer viability measurement was linear above 25% viability, and optimal range was 50-100% viable. (FIG. 15G).

The invention claimed is:

1. A method for selecting a pharmaceutical composition for reducing hyperphenylalaninemia, comprising a genetically engineered bacteria comprising one or more gene(s) for producing a phenylalanine ammonia lyase (PAL), wherein the method comprises:

determining the live cell count of the genetically engineered bacteria in a first composition, wherein the live cell count provides a more accurate measure of therapeutic activity than colony-forming units (CFU) by determining a percent of live cells in the first composition, wherein the percent of live cells is the number of living cells divided by the total number of cells multiplied by 100; wherein when the first composition comprises between $1\times10^8$ to $1\times10^{13}$ live cells as determined by live cell counting, and wherein when the percent live cells in the first composition is at least 60% of the total number of cells, selecting the first composition as a second composition;

determining the activity of the second composition by measuring:

(1) a transcinnamic acid (TCA) production rate of the second composition, and selecting the second composition as the pharmaceutical composition wherein it is capable of producing transcinnamic acid (TCA) at a rate of at least approximately 0.5 μmol/hour/$10^9$ live cells, (2) a phenyl pyruvic acid (PPA) production rate of the second composition, and selecting the second composition as the pharmaceutical composition wherein it is capable of producing PPA at a rate of at least approximately 1.0 μmol/hour/$10^9$ live cells, and/or (3) an increased hippurate (HA) or labeled D5-HA of the second composition relative to a control, wherein the control comprises the unmodified bacterium, and selecting the second composition as the pharmaceutical composition wherein it demonstrates an increased HA or labeled D5-HA level relative to the control; and administering the selected pharmaceutical composition to a subject in need thereof for reducing hyperphenylalaninemia.

2. The method of claim 1, wherein the genetically engineered bacterium comprises one or more non-native gene(s) for the treatment of phenylketonuria in the subject.

3. The method of claim 2, wherein the one or more gene(s) are operably linked to an inducible promoter, wherein the one or more gene(s) are induced:

a) when the selected pharmaceutical composition is administered to the subject; or b) prior to the selected pharmaceutical composition being administered to the subject.

4. The method of claim 1, wherein the genetically engineered bacterium comprises:

a) the gene(s) encoding the PAL operably linked to an inducible promoter that is not associated with the PAL gene in nature, wherein the PAL is from *Anabaena variabilis* (PAL1) or from *Photorhabdus luminescens* (PAL3);

b) one or more gene(s) encoding a phenylalanine transporter, wherein the gene(s) encoding the phenylalanine transporter is operably linked to an inducible promoter that is not associated with the phenylalanine transporter gene in nature; and c) one or more gene(s) encoding an L-amino acid deaminase (LAAD), wherein the gene(s) encoding LAAD is operably linked to an inducible promoter that is not associated with the LAAD gene in nature.

5. The method of claim 4, wherein:

a) the promoter operably linked to the gene(s) encoding a PAL and the promoter operably linked to the gene(s) encoding a phenylalanine transporter are separate copies of the same promoter;

b) the gene(s) encoding a PAL and the gene(s) encoding a phenylalanine transporter are operably linked to a single promoter; or c) the gene(s) encoding a PAL and the gene(s) encoding a phenylalanine transporter are operably linked to different promoters.

6. The method of claim 4, wherein:

a) the gene(s) encoding a LAAD, the gene(s) encoding a PAL, and the gene(s) encoding a phenylalanine transporter are operably linked to separate copies of the same promoter; or b) the gene(s) encoding a LAAD is operably linked to a different promoter from the promoter operably linked to the gene(s) encoding a PAL and the gene(s) encoding a phenylalanine transporter.

7. The method of claim 4, wherein the promoter operably linked to the gene(s) encoding the phenylalanine transporter, the promoter operably linked to the gene(s) encoding the PAL, and/or the promoter operably linked to the gene(s) encoding the LAAD is selected from the group consisting of a promoter that is induced under low-oxygen or anaerobic conditions, a thermoregulated promoter, and a promoter that is induced by arabinose, IPTG, tetracycline, or rhamnose, wherein the promoter that is induced under low-oxygen or anaerobic conditions is selected from the group consisting of a fumarate and nitrate reductase regulator (FNR)-responsive promoter, an arginine deiminase and nitrate reduction (ANR)-responsive promoter, and a dissimilatory nitrate respiration regulator (DNR)-responsive promoter.

8. The method of claim 4, wherein the gene(s) encoding the phenylalanine transporter, the gene(s) encoding the PAL, and/or the gene(s) encoding the LAAD is:

a) located on a chromosome in the genetically engineered bacterium; or b) located on a plasmid in the genetically engineered bacterium.

9. The method of claim 4, wherein the phenylalanine transporter is PheP.

10. The method of claim 1, wherein the genetically engineered bacterium is an auxotroph in diaminopimelic acid or in thymidine.

11. The method of claim 1, wherein the bacterium is selected from the group consisting of *Bacteroides, Bifidobacterium, Clostridium, Escherichia, Lactobacillus*, and *Lactococcus*.

12. The method of claim 11, wherein the bacterium is *Escherichia coli* strain Nissle.

* * * * *